US007252974B2

(12) United States Patent
Rappold-Hoerbrand et al.

(10) Patent No.: US 7,252,974 B2
(45) Date of Patent: Aug. 7, 2007

(54) HUMAN GROWTH GENE AND SHORT STATURE GENE REGION

(75) Inventors: Gudrun Rappold-Hoerbrand, Heidelberg (DE); Ercole Rao, Riedstadt (DE)

(73) Assignee: Gudrun Rappold-Hoerbrand, Heidelberg (DE)

( * ) Notice: Subject to any disclaimer, the term of this patent is extended or adjusted under 35 U.S.C. 154(b) by 0 days.

(21) Appl. No.: 10/158,160

(22) Filed: May 31, 2002

(65) Prior Publication Data

US 2003/0059805 A1    Mar. 27, 2003

Related U.S. Application Data

(63) Continuation of application No. 09/147,699, filed as application No. PCT/EP97/05355 on Sep. 29, 1997, now abandoned.

(60) Provisional application No. 60/027,633, filed on Oct. 1, 1996.

(30) Foreign Application Priority Data

Jan. 16, 1997 (GB) ............................... 97100583.0

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. .................. 435/91.2; 435/6; 435/91.1; 536/23.1; 536/24.3; 536/24.33; 536/25.3

(58) Field of Classification Search .................. 435/6, 435/91.1, 91.2, 183; 436/94; 536/23.1, 536/24.3, 24.33, 25.3, 25.32
See application file for complete search history.

(56) References Cited

U.S. PATENT DOCUMENTS 4,727,061 A * 2/1988 Kramer et al. ................ 514/18
4,983,511 A * 1/1991 Geiger et al. .................. 435/6

OTHER PUBLICATIONS

New England Biolabs Catalog 1986/87 (pp. 60-63). Published by New England Biolabs, 32 Tozer Road, Beverly, MA 01915-9990, USA.*
1996/97 New England Biolabs Catalog (pp. 112-114). Published by New England Biolabs, 32 Tozer Road, Beverly, MA 01915-5599, USA.*
New England Biolabs Catalog 1986/87 (pp. 55 and 60-63). Published by New England Biolabs, 32 Tozer Road, Beverly, MA 01915-9990, USA.*
Ashworth A, Rastan S, Lovell-Badge R, Kay G (1991): X-chromosome inactivation may explain the difference in viability of X0 humans and mice. Nature 351: 406-408, abstract.

Ballabio A, Bardoni A, Carrozzo R, Andria G, Bick D, Campbell L, Hamel B, Ferguson-Smith MA, Gimelli G, Fraccaro M, Maraschio P, Zuffardi O, Guilo S, Camerino G (1989): Contiguous gene syndromes due to deletions in the distal short arm of the human X chromosome. Proc Natl Acad Sci USA 86:10001-10005.
Blagowidow N, Page DC, Huff D, Mennuti MT (1989): Ullrich-Turner syndrome in an XY female fetus with deletion of the sex-determining portion of the Y chromosome. Am. J. med. Genet. 34: 159-162, abstract.
Cantrell MA, Bicknell JN, Pagon RA et al. (1989): Molecular analysis of 46,XY females and regional assignment of a new Y-chromosome-specific probe. Hum. Genet. 83: 88-92, abstract.
Connor JM, Loughlin SAR (1989): Molecular genetics of Turner's syndrome. Acta Pediatr. Scand. (Suppl.) 356: 77-80, abstract.
Disteche CM, Casanova M, Saal H, Friedmen C, Sybert V, Graham J, Thuline H, Page DC, Fellous M (1986): Small deletions of the short arm of the Y-chromosome in 46,XY females. Proc Natl Acad Sci USA 83:7841-7844, abstract.
Ferguson-Smith MA (1965): Karyotype-phenotype correlations in gonadal dysgenesis and their bearing on the pathogenesis of malformations. J. med. Genet. 2: 142-155.
Ferrari D, Kosher RA, Dealy CN (1994): Limp mesenchymal cells inhibited from undergoing cartilage differentiation by a tumor promoting phorbol ester maintain expression of the homeobox-containing gene *MSX1* and fail to exhibit gap junctional communication. Biochemical and Biophysical Research Communications. 205(1): 429-434, abstract.
Fischer M, Bur-Romero P, Brown LG et al. (1990): Homologous ribosomal protein genes in the human X- and Y-chromosomes escape from X-inactivation and possible implementation for Turner syndrome. Cell 63: 1205-1218, abstract.
Freund C, Horsford DJ, McInnes RR (1996): Transcription factor genes and the developing eye: a genetic perspective. Hum Mol Genet 5: 1471-1488, abstract.
Gehring WJ, Qian YQ, Billeter M, Furukubo-Tokunaga K, Schier A F, Resendez-Perez D, Affolter M, Otting G, Wüthrich K (1994): Homeodomain-DNA recognition. Cell 78: 211-223.
Gough NM, Gearing DP, Nicola NA, Baker E, Pritchard M, Callen DF, Sutherland GR (1990). Localization of the human GM-CSF receptor gene to the X-Y pseudoautosomal region. Nature 345: 734-736, abstract.

(Continued)

*Primary Examiner*—Frank Lu
(74) *Attorney, Agent, or Firm*—Rothwell, Figg, Ernst & Manbeck, PC

(57) ABSTRACT

Subject of the present invention is an isolated human nucleic acid molecule encoding polypeptides containing a homeobox domain of sixty amino acids having the amino acid sequence of SEQ ID NO: 1 and having regulating activity on human growth. Three novel genes residing within the about 500 kb short stature critical region on the X and Y chromosome were identified. At least one of these genes is responsible for the short stature phenotype. The cDNA corresponding to this gene may be used in diagnostic tools, and to further characterize the molecular basis for the short stature-phenotype. In addition, the identification of the gene product of the gene provides new means and methods for the development of superior therapies for short stature.

7 Claims, 5 Drawing Sheets

OTHER PUBLICATIONS

Hall JG, Gilchrist DM (1990): Turner syndrome and its variants. Pedriatr. Clin. North Am. 37: 1421-1436, abstract.
Henke A, Wapenaar M, van Ommen G-J, Maraschio P, Camerino O, Rappold GA (1991): Deletions within the pseudoautosomal region help map three new markers and indicate a possible role of this region in linear growth. Am J Hum Genet 49:811-819, abstract.
Hernandez D, Fisher EMC (1996): Down syndrome genetics: unravelling a multifactorial disorder. Hum Mol Genet 5:1411-1416.
Kenyon C (1994): If birds can fly, why can't we? Homeotic genes and evolution. Cell 78: 175-180.
Krumlauf R (1994): *Hox* genes in vertebrate development. Cell 78: 191-201.
Kulharya AS, Roop H, Kukolich MK, Nachtman RG, Belmont JW, Garcia-Heras J (1995): Mild phenotypic effects of a de novo deletion Xpter ® Xp22.3 and duplication 3pter ® 3p23. Am J Med Genet 56:16-21, abstract.
Lawrence PA, Morata G (1994): Homeobox genes: their function in Drosophila segmentation and pattern formation. Cell 78: 181-189.
Levilliers J, Quack B, Weissenbach J, Petit C (1989): Exchange of terminal portions of X- and Y-chromosomal short arms in human XY females. Proc Natl Acad Sci USA 86:2296-2300.
Lippe BM (1991): Turner Syndrome. Endocrinol Metab Clin North Am 20: 121-152, abstract.
Nelson DL, Ballabio A, Cremers F, Monaco AP, Schlessinger D (1995).- Report of the sixth international workshop on the X chromosome mapping. Cytogenet. Cell Genet. 71: 308-342.
Ogata T, Goodfellow P, Petit C, Aya M, Matsuo N (1992): Short stature in a girl with a terminal Xp deletion distal to DXYS15: localization of a growth gene(s) in the pseudoautosomal region. J Med Genet 29:455-459, abstract.
Ogata T, Tyler-Smith C, Purvis-Smith S, Turner G (1993): Chromosomal localisation of a gene(s) for Turner stigmata on Yp. J. Med. Genet. 30: 918-922, abstract.
Ogata T, Yoshizawa. A, Muroya K, Matsuo N, Fukushima Y, Rappold GA, Yokoya S (1995): Short stature in a girl with partial monosomy of the pseudoautosomal region distal to DXYS15: further evidence for the assignment of the critical region for a pseudoautosomal growth gene(s). J Med Genet 32:831-834.
Ogata T, Matsuo N (1995): Turner syndrome and female sex chromosome aberrations: deduction of the principle factors involved in the development of clinical features. Hum. Genet. 95: 607-629.
Orita M, Suzuki Y, Sekiya T and Hayashi K (1989): Rapid and sensitive detection of point mutations and polymorphisms using the polymerase chain reaction. Genomics 5:874-879, abstract.
Pohlschmidt M, Rappold G, Krause M, Ahlert D, Hosenfeld D, Weissenbach J, Gal A (1991): Ring Y chromosome: Molecular characterization by DNA probes. Cytogenet Cell Genet 56:65-68, abstract.
Rao E, Weiss B, Mertz A et al. (1995): Construction of a cosmid contig spanning the short stature candidate region in the pseudoautosomal region PAR 1. in: Turner syndrome in a life span perspective: Research and clinical aspects. Proceedings of the 4th International Symposium on Turner Syndrome, Gothenburg, Sweden, May 18-21, 1995., edited by Albertsson-Wikland K, Ranke MB, pp. 19-24, Elsevier.
Rao E, Weiss B, Fukami M, Rump A, Niesler B, Mertz A, Muroya K, Binder G, Kirsch S, Winkelmann M, Nordsiek G, Heinrich U, Breuning MH, Ranke MB, Rosenthal A, Ogata T, Rappold GA (1997): Pseudoautosomal deletions encompassing a novel homeobox gene cause growth failure in idiopathic short stature and Turner syndrome. Nature Genet 16:54-63, abstract.
Rappold GA (1993): The pseudoautosomal region of the human sex chromosomes. Hum Genet 92:315-324.
Rappold GA, Willson TA, Henke A, Gough NM (1992): Arrangement and localization of the human GM-CSF receptor a chain gene CSF2RA within the X-Y pseudoautosomal region. Genomics 14:455-461, abstract.
Reid K, Mertz A, Nagaraja R, Trusnich M, Riley J, Anand R, Page D, Lehrach H., Elliso J, Rappold GA (1995): Characterization of a yeast artificial chromosome contig spanning the pseudoautosomal region. Genomics 29:787-792, abstract.
Magenis RE, Tochen ML Holahan KP, Carey T, Allen L, Brown MG (1984): Turner syndrome resulting from partial deletion of Y-chromosome short arm: localization of male determinants. J Pediatr 105: 916-919, abstract.
P. Saenger et al., The Journal of Clinical Endocrinology & Metabolism, vol. 86, No. 7, pp. 3061-3069, Recommendations for the Diagnosis and Management of Turner Syndrome, 2001.
Rovescalli AC, Asoh S, Nirenberg M (1996): Cloning and characterization of four murine homeobox genes. Proc Natl Acad Sci USA 93:10691-10696.
Schaefer L, Ferrero GB, Grillo A, Bassi MT, Roth EJ, Wapenaar MC, van Ommen G-JB, Mohandas TK, Rocchi M, Zoghbi HY, Ballabio A (1993): A high resolution deletion map of human chromosome Xp22. Nature genetics 4: 272-279, abstract.
Vimpani GV, Vimpani AF, Lidgard GP, Cameron EHD, Farquhar JW (1977) Prevalence of severe growth hormone deficiency. Br Med J. 2: 427-430, abstract.
Zinn AR, Page DC, Fisher EMC (1993): Turner syndrome: the case of the missing sex chromosome. TIG 9 (3): 90-93, abstract.
M. Marra et al., mi75d03.r1 Soares mouse p3NMF19.5 Mus Musculus cDNA clone 481925 5 similar to TR: . . . , EMBL Database Entry, Sep. 24, 1996, XP002052953.
M. Marra et al., mb68b03.r1 Soares mouse p3NMF19.5 Mus Musculus cDNA clone334541 5' similar to SW: . . . , EMBL Database Entry, May 4, 1996, XP002052954.
E. Rao et al., "Construction of a cosmid contig spanning the short stature candidate region in the pseudoautosomal region PAR 1." May 18-21, 1995, pp. 19-24, XP002052955.
L. Hiller et al., zb81a08.s1 Homosapiens cDNA clone 309974 3' similar to PIR . . . , EMBL Database Entry, HS100314, Apr. 19, 1996, XP002052956.
T. Ogata et al., "short stature in a girl with partial monosomy of the pseudoautosomal region distal to DXYS15 . . . ", Journal of Medical Genetics, vol. 32, No. 10, Oct. 1995, pp. 831-834.
A. Henke et al., "Deletions within the pseudoautosomal region help map three new markers and indicate a possible role of this region in linear growth", American Journal of Human Genetics, vol. 49, No. 4, Oct. 1991, pp. 811-819.
B.W. Schafer et al., "Molecular cloning and characterization of a human PAX-7 cDNA expressed in normal and neoplastic myocytes.", Nucleic Acids Research, vol. 22, No. 22, 1994, pp. 4574-4582.
E. Rao et al., "Pseudoautosomal deletions encompassing a novel homeobox gene cause growth failure in idiopathic short stature and Turner syndrome.", Nature Genetics, vol. 16, No. 1, Apr. 1997, pp. 54-63.
J.W. Ellison et al., "PHOG, a candidate gene for involvement in the short stature of Turner Syndrome.", Human Molecular Genetics, vol. 6, No. 8, Aug. 1997, pp. 1341-1347.
A.C. Rovescalli et al., "Cloning and characterization of four murine homeobox genes", Proceedings of the National Academy of Sciences of USA, vol. 93, Oct. 1, 1996, pp. 10691-10696.
E. Rao et al., "FISH-deletion mapping defines a 270-kb short stature critical interval in the pseudoautosomal region PAR1 on human sex chromosomes", Hum Genet (1997) 100:236-239.
T. Ogata et al., "Chromosomal localisation of a pseudoautosomal growth gene(s)", J. Med. Genet, 1992; 29; pp. 624-628.
Ellison et al., "Rapid evolution of human pseudoautosomal genes and their mouse homologs", Mammalian Genome, 7, (1996), pp. 25-30.
European Patent Disclosure, BIOWORLD Today, vol. 9, iss. 101, May 28, 1998.
Endocrinology 1997 (German), 1998.
Shot, a Shox-related homeobox gen is implicated in craniofacial, brain, heart, and limb development, Institute of Human Genetics, Proc. Nation. Acad. Sci. USA, 1998, 95(5) 2406-2411.
Homeobox gene Prx3 expression in rodent brain and extraneural tissues, Van Schaick et al., Proc. Natl. Acad. Sci. USA (1997) 94(24), 12933-12988.
OI-Prx 3, a member of an additional class of homeobox genes . . . , Proc. Natl. Acad. Sci. USA, (1997), 94(24), 12987-12992.

Mutation and deletion of the pseudoautosomal gene SHOX cause Leri-Weill dyschondrosteosis, Nat. Genet. (1998), 19(1) 70-73.

SHOX mutations in dyschondrosteosis (Leri-Weill syndrome), Nat. Genet. 1998, 19(1), 67-69.

A new human homeobox gene OG12X is a member of the most conserved homeobox gene family and is expressed during heart development in mouse, Hum. Mol. Genet. (1998), 7(3), 415-422.

Homeobox gene Prx3 expression in rodent brain and extraneural tissues, Proc. Natl. Acad. Sci. U.S.A., (1997), 94(24) 12993-12998.

Dorn A., et al., Homeodomaine proteins in development and therapy, Pharmacology & Therapeutics, 61(1-2):155-84, 1994, Citation 47.

Abstract, "The effect of growth hormone treatment in idiopathic short stature with SHOX mutation.", Vuguin et al., Nature Genetics 16:54-63, 1997.

Ellison et al., SHOX/PHOG genes, Hum Mol Genet, Aug. 1997:6(8):1341-1347.

Zinn, "Growing interest in Turner syndrome", News & Views.

News of Lilly, Dec. 11, 1996, "Lilly's Humatrope Recommended for FDA Marketing Clearance for Turner Syndrome".

News of Lilly, Apr. 1, 1997, "Lilly's Humatrope (somatropin[rDNA origin] for injection), Receives FDA Marketing Clearance for Turner Syndrome."

Shears et al., Mutation and deletion of the pseudoautosomal gene SHOX cause Leri-Weill dyschondrosteosis, Nature Genetics, vol. 19, May 1998.

Product label for HUMATROPE.

Belin et al., "SHOX mutations in dyschondrosteosis (Leri-Weill syndrome)" Nature Genetics, vol. 19, May 1998.

Rovescalli et al., GenEmbl Accession No. U67055, Oct. 1996.

Hillier et al., EST Accession No. AA081138, Oct. 1996.

\* cited by examiner

FIGURE 2

SHOXa

```
   1  GTGATCCACCCGCGCGCACGGGCCGTCCTCTCCGCGCGGGGAGACGCGCGCATCCACCAG
  61  CCCCGGCTGCTCGCCAGCCCCGGCCCCAGCCATGGAAGAGCTCACGGCTTTTGTATCCAA
   1                                 M  E  E  L  T  A  F  V  S  K
 121  GTCTTTTGACCAGAAAAGCAAGGACGGTAACGGCGGAGGCGGAGGCGGCGGAGGTAAGAA
  11    S  F  D  Q  K  S  K  D  G  N  G  G  G  G  G  G  G  K  K
 181  CGATTCCATTACGTACCGGGAAGTTTTGGAGAGCGGACTGGCGCGCTCCCGGGAGCTGGG
  31    D  S  I  T  Y  R  E  V  L  E  S  G  L  A  R  S  E  L  G
 241  GACGTCGGATTCCAGCCTCCAGGACATCACGGAGGGCGGCGGCCACTGCCCGGTGCATTT
  51    T  S  D  S  S  L  Q  D  I  T  E  G  G  G  H  C  P  V  H  L
 301  GTTCAAGGACCACGTAGACAATGACAAGGAGAAACTGAAAGAATTCGGCACCGCGAGAGT
  71    F  K  D  H  V  D  N  D  K  E  K  L  K  E  F  G  T  A  R  V
 361  GGCAGAAGGGATTTATGAATGCAAAGAGAAGCGCGAGGACGTGAAGTCGGAGGACGAGGA
  91    A  E  G  I  Y  E  C  K  E  K  R  E  D  V  K  S  E  D  E  D
 421  CGGGCAGACCAAGCTGAAACAGAGGCGCAGCCGCACCAACTTCACGCTGGAGCAGCTGAA
 111    G  -  Q  T  K  L  K  Q  R  R  S  R  T  N  F  T  L  E  Q  L  N
 481  CGAGCTCGAGCGACTTTTTGACGAGACCCATTACCCCGACGCCTTCATGCGCGAGGAGCT
 131    E  L  E  R  L  F  D  E  T  H  Y  P  D  A  F  M  R  E  E  L
 541  CAGCCAGCGCCTGGGGCTTTCCGAGGCGCGCGTGCAGGTTTGGTTCCAGAACCGGAGAGC
 151    S  Q  R  L  G  L  S  E  A  R  V  Q  V  W  F  Q  N  R  R  A
 601  CAAGTGCCGCAAACAAGAGAATCAGATGCATAAAGGCGTCATCTTGGGCACAGCCAACCA
 171    K  C  R  K  Q  E  N  Q  M  H  K  G  V  I  L  G  T  A  N  H
 661  CCTAGACGCCTGCCGAGTGGCACCCTACGTCAACATGGGAGCCTTACGGATGCCTTTCCA
 191    L  D  A  C  R  V  A  P  Y  V  N  M  G  A  L  R  M  P  F  Q
 721  ACAGGTCCAGGCTCAGCTGCAGCTGGAAGGCGTGGCCCACGCGCACCCGCACCTGCACCC
 211    Q  V  Q  A  Q  L  Q  L  E  G  V  A  H  A  H  P  H  L  H  P
 781  GCACCTGGCGGCGCACGCGCCCTACCTGATGTTCCCCCCGCCGCCCTTCGGGCTGCCCAT
 231    H  L  A  A  H  A  P  Y  L  M  F  P  P  P  P  F  G  L  P  I
 841  CGCGTCGCTGGCCGAGTCCGCCTCGGCCGCCGCCGTGGTCGCCGCCGCCGCCAAAAGCAA
 251    A  L  S  A  E  S  A  S  A  A  A  V  V  A  A  A  A  K  S  N
 901  CAGCAAGAATTCCAGCATCGCCGACCTGCGGCTCAAGGCGCGGAAGCACGCGGAGGCCCT
 271    S  K  N  S  S  I  A  D  L  R  L  K  A  R  K  H  A  E  A  L
 961  GGGGCTCTGACCCGCCGCGCAGCCCCCGCGCGCCCGGACTCCCGGGCTCCGCGCACCCC
 291    G  L  *
1021  GCCTGCACCGCGCGTCCTGCACTCAACCCCGCCTGGAGCTCCTTCCGCGGCCACCGTGCT
1081  CCGGGCACCCCGGGAGCTCCTGCAAGAGGCCTGAGGAGGGAGGCTCCCGGGACCGTCCAC
1141  GCACGACCCAGCCAGACCCTCGCGGAGATGGTGCAGAAGGCGGAGCGGGTGAGCGGCCGT
1201  GCGTCCAGCCCGGGCCTCTCCAAGGCTGCCCGTGCGTCCTGGGACCCTGGAGAAGGGTAA
1261  ACCCCCGCCTGGCTGCGTCTTCCTCTGCTATACCCTATGCATGCGGTTAACTACACACGT
1321  TTGGAAGATCCTTAGAGTCTATTGAAACTGCAAAGATCCCGGAGCTGGTCTCCGATGAAA
1381  ATGCCATTTCTTCGTTGCCAACGATTTTCTTTACTACCATGCTCCTTCCTTCATCCCGAG
1441  AGGCTGCGGAACGGGTGTGGATTTGAATGTGGACTTCGGAATCCCAGGAGGCAGGGGCCG
1501  GGCTCTCCTCCACCGCTCCCCGGAGCCTCCAGGCAGCAATAAGGAAATAGTTCTCTGG
1561  CTGAGGCTGAGGACGTGAACCGCGGGCTTTGGAAAGGGAGGGGAGGGAGACCCGAACCTC
1621  CCACGTTGGGACTCCCACGTTCCGGGGACCTGAATGAGGACCGACTTTATAACTTTTCCA
1681  GTGTTTCATTCCCAAATTGGGTCTGGTTTTGTTTTGGATTGGTATTTTTTTTTTTTTTTT
1741  TTTTTGCTGTGTTACAGGATTCAGACGCAAAAGACTTGCATAAGAGACGGACGCGTGGTT
1801  GCAAGGTGTCATACTGATATGCAGCATTAACTTTACTGACATGGAGTGAAGTGCAATATT
1841  ATAAATATTATAGATTAAAAAAAAAATAGC[A]n
```

FIGURE 3

SHOXb

```
   1  GTGATCCACCCGCGCGCACGGGCCGTCCTCTCCGCGCGGGGAGACGCGCGCATCCACCAG
  61  CCCCGGCTGCTCGCCAGCCCCGGCCCCAGCCATGGAAGAGCTCACGGCTTTTGTATCCAA
   1                                  M  E  E  L  T  A  F  V  S  K
 121  GTCTTTTGACCAGAAAAGCAAGGACGGTAACGGCGGAGGCGGAGGCGGCGGAGGTAAGAA
  11   S  F  D  Q  K  S  K  D  G  N  G  G  G  G  G  G  G  K  K
 181  GGATTCCATTACGTACCGGGAAGTTTTGGAGAGCGGACTGGCGCGCTCCCGGGAGCTGGG
  31   D  S  I  T  Y  R  E  V  L  E  S  G  L  A  R  S  R  E  L  G
 241  GACGTCGGATTCCAGCCTCCAGGACATCACGGAGGGCGGCGGCCACTGCCCGGTGCATTT
  51   T  S  D  S  S  L  Q  D  I  T  E  G  G  H  C  P  V  H  L
 301  GTTCAAGGACCACGTAGACAATGACAAGGAGAAACTGAAAGAATTCGGCACCGCGAGAGT
  71   F  K  D  H  V  D  N  D  K  E  K  L  K  E  F  G  T  A  R  V
 361  GGCAGAAGGGATTTATGAATGCAAAGAGAAGCGCGAGGACGTGAAGTCGGAGGACGAGGA
  91   A  E  G  I  Y  E  C  K  E  K  R  E  D  V  K  S  E  D  E  D
 421  CGGGCAGACCAAGCTGAAACAGAGGCGCAGCCGCACCAACTTCACGCTGGAGCAGCTGAA
 111   G  Q  T  K  L  K  Q  R  R  S  R  T  N  F  T  L  E  Q  L  N
 481  CGAGCTCGAGCGACTTTTTGACGAGACCCATTACCCCGACGCCTTCATGCGCGAGGAGCT
 131   E  L  E  R  L  F  D  E  T  H  Y  P  D  A  F  M  R  E  E  L
 541  CAGCCAGCGCCTGGGGCTTTCCGAGGCGCGCGTGCAGGTTTGGTTCCAGAACCGGAGAGC
 151   S  Q  R  L  G  L  S  E  A  R  V  Q  V  W  F  Q  N  R  R  A
 601  CAAGTGCCGCAAACAAGAGAATCAGATGCATAAAGGCGTCATCTTGGGCACAGCCAACCA
 171   K  C  R  K  Q  E  N  Q  M  H  K  G  V  I  L  G  T  A  N  H
 661  CCTAGACGCCTGCCGAGTGGCACCCTACGTCAACATGGGAGCCTTACGGATGCCTTTCCA
 191   L  D  A  C  R  V  A  P  Y  V  N  M  G  A  L  R  M  P  F  Q
 721  ACAGATGGAGTTTTGCTCTTGTCGCCCAGGCTGGAGTATAATGGCATGATCTCGACTCAC
 211   Q  M  E  F  C  S  C  R  P  G  W  S  I  M  A  *
 781  TGCAACCTCCGCCTCCCGAGTTCAAGCGATTCTCCTGCCTCAGCCTCCCGAGTAGCTGGG
 841  ATTACAGGTGCCCACCACCATGTCAAGATAATGTTTGTATTTTCAGTAGAGATGGGGTTT
 901  GACCATGTTGGCCAGGCTGGTCTCGAACTCCTGACCTCAGGTGATCCACCCGCCTTAGCC
 961  TCCCAAAGTGCTGGGATGACAGGCGTGAGCCCCTGCGCCCGGCCTTTGTAACTTTATTTT
1021  TAATTTTTTTTTTTTTTAAGAAAGACAGAGTCTTGCTCTGTCACCCAGGCTGGAGCACA
1081  CTGGTGCGATCATAGCTCACTGCAGCCTCAAACTCCTGGGCTCAAGCAATCCTCCCACCT
1141  CAGCCTCCTGAGTAGCTGGGACTACAGGCACCCACCACCACACCCAGCTAATTTTTTGA
1201  TTTTTACTAGAGACGGGATCTTGCTTTGCTGCTGAGGCTGGTCTTGAGCTCCTGAGCTCC
1261  AAAGATCCTCTCACCTCCACCTCCCAAAGTGTTAGAATTACAAGCATGAACCACTGCCCG
1321  TGGTCTCCAAAAAAAGGACTGTTACGTGG [A]ₙ
```

FIGURE 4

```
GTGTCCCCGGAGCTGAAAGATCGCAAAGAGGATGCGAAAGGGATGGAGGACGAAGGCCAG
                                           M  E  D  E  G  Q

ACCAAAATCAAGCAGAGGCGAAGTCGGACCAATTTCACCCTGGAACAACTCAATGAGCTG
 T  K  I  K  Q  R  R  S  R  T  N  F  T  L  E  Q  L  N  E  L

GAGAGGCTTTTTGACGAGACCCACTATCCCGACGCCTTCATGCGAGAGGAACTGAGCCAG
 E  R  L  F  D  E  T  H  Y  P  D  A  F  M  R  E  E  L  S  Q

CGACTGGGCCTGTCGGAGGCCCGAGTGCAGGTTTGGTTTCAAAATCGAAGAGCTAAATGT
 R  L  G  L  S  E  A  R  V  Q  V  W  F  Q  N  R  R  A  K  C

AGAAAACAAGAAAATCAACTCCATAAAGGTGTTCTCATAGGGGCCGCCAGCCAGTTTGAA
 R  K  Q  E  N  Q  L  H  K  G  V  L  I  G  A  A  S  Q  F  E

GCTTGTAGAGTCGCACCTTATGTCAACGTAGGTGCTTTAAGGATGCCATTTCAGCAGGAT
 A  C  R  V  A  P  Y  V  N  V  G  A  L  R  M  P  F  Q  Q  D

AGTCATTGCAACGTGACGCCCTTGCCCTTTCAGGTTCAGGCGCAGCTGCAGCTGGACAGC
 S  H  C  N  V  T  P  L  P  F  Q  V  Q  A  Q  L  Q  L  D  S

GCTGTGGCGCACGCGCACCACCACCTGCATCCGCACCTGGCCGCGCACGCGCCCTACATG
 A  V  A  H  A  H  H  H  L  H  P  H  L  A  A  H  A  P  Y  M

ATGTTCCCAGCACCGCCCTTCGGACTGCCGCTCGCCACGCTGGCCGCGGATTCGGCTTCC
 M  F  P  A  P  P  F  G  L  P  L  A  T  L  A  A  D  S  A  S

GCCGCCTCGGTAGTGGCGGCCGCAGCAGCCGCCAAGACCACCAGCAAGGACTCCAGCATC
 A  A  S  V  V  A  A  A  A  A  K  T  T  S  K  D  S  S  I

GCCGATCTCAGACTGAAAGCCAAAAAGCACGCCGCAGCCCTGGGTCTGTGACGCCAACGC
 A  D  L  R  L  K  A  K  K  H  A  A  A  L  G  L  *

CAGCACCAATGTCGCGCCTGTCCCGCGGCACTCAGCCTGCACGCCCTCCGCGCCCCGCTG
CTTCTCCGTTACCCCTTTGAGACCTCGGGAGCCGGCCCTCTTCCCGCCTCACTGACCATC
CCTCGTCCCCTATCGCATCTTGGACTCGGAAAGCCAGACTCCACGCAGGACCAGGGATCT
CACGAGGCACGCAGGCTCCGTGGCTCCTGCCCGTTTTCCTACTCGAGGGCCTAGAATTGG
GTTTTGTAGGAGCGGGTTTGGGGGAGTCTGGAGAGAGACTGGACAGGGTAGTGCTGGAAC
CGCGGAGTTTGGCTCACCGCAAAGCTACAACGATGGACTCTTGCATAGAAAAAAAAAATC
TTGTTAACAATGAAAAAATGAGCAAACAAAAAAATCGAAAGACAAACGGGAGAGAAAAAG
AGGAAGGCAACTTATTTCTTAACTGCTATTTGGCAGAAGCTGAAATTGGAGAACCAAGGA
GCAAAAACAAATTTTAAAATTAAAGTATTTTATACATTTAAAAATATGGAAAAACAACCC
AGACGATTCTCGAGAGACTGGGGGGAGTTACCAACTTAAATGTGTGTTTTAAAAAATGCG
CTAAGAAGGCAAAGCAGAAAGAAGAGGTATACTTATTTAAAAAACTAAGATGAAAAAAGT
GCGCAGGTGGGAAGTTCACAGGTTTTGAAACTGACCTTTTTCTGCGAAGTTCACGTTAAT
ACGAGAAATTTGATGAGAGAGGCGGGCCTCCTTTTACGTTGAATCAGATGCTTTGAGTTT
AAACCCACCATGTATGGAAGAGCAAGAAAAGAGAAAATATTAAAACGAGGAGAGAGAAAA
ATAATGGCAAAACTGTCTGGACTGCTGACAGTAAATTCCGGTTTGCATGGAAAAAAAAAA
AAAAAAAAAAAAAAAAA
```

FIGURE 5

Exon/Intron Organization of the human SHOX gene

| Exon | cDNA-a | cDNA-b | genomic DNA | Exon Size | Intron/Exon | Exon/Intron |
|---|---|---|---|---|---|---|
| I | UTR-368 | UTR-368 | 1-368 | 368 | GTGATCCACC | GTGGCAGAAGgtaagttcct |
| II | 369-577 | 369-577 | 3817-4025 | 209 | cccacgcagGGATTTATGA | GCGCGTGCAGgtaggaaccc |
| III | 578-635 | 578-635 | 9851-9908 | 58 | tctccccaagGTTTGGTTCC | ATGCATAAAGgtgggtgtcg |
| IV | 636-724 | 636-724 | 10029-10117 | 89 | ttgacacagGCGTCATCTT | TTTCCAACAGgtagctcact |
| Va | 725-1890 | — | 13364-14529 | 1166 | gctcccgcagGTCCAGGCTC | AAAAATAGC |
| Vb | — | 725-1349 | 27154-27778 | 625 | ttttttttagATGGAGTTTT | TGTTACGTGG |
| polyA | ≥1891 | ≥1350 | | | | |

Sizes of exons are given in basepairs; exon sequences are shown in capital letters; donor and acceptor splice sites are underlined. Genomic and cDNA sequences are available via GenBank accession no xyz

```
                        SEQUENCE LISTING

<160> NUMBER OF SEQ ID NOS: 55

<210> SEQ ID NO 1
<211> LENGTH: 60
<212> TYPE: PRT
<213> ORGANISM: Homo sapiens

<400> SEQUENCE: 1

Gln Arg Arg Ser Arg Thr Asn Phe Thr Leu Glu Gln Leu Asn Glu Leu
 1               5                  10                  15

Glu Arg Leu Phe Asp Glu Thr His Tyr Pro Asp Ala Phe Met Arg Glu
            20                  25                  30

Glu Leu Ser Gln Arg Leu Gly Leu Ser Glu Ala Arg Val Gln Val Trp
        35                  40                  45

Phe Gln Asn Arg Arg Ala Lys Cys Arg Lys Gln Glu
    50                  55                  60

<210> SEQ ID NO 2
<211> LENGTH: 209
<212> TYPE: DNA
<213> ORGANISM: Homo sapiens

<400> SEQUENCE: 2
ggatttatga atgcaaagag aagcgcgagg acgtgaagtc ggaggacgag gacgggcaga      60
ccaagctgaa acagaggcgc agccgcacca acttcacgct ggagcagctg aacgagctcg     120
agcgactctt cgacgagacc cattacccgg acgccttcat gcgcgaggag ctcagccagc     180
```

| | |
|---|---|
| gcctggggct ctccgaggcg cgcgtgcag | 209 |

<210> SEQ ID NO 3
<211> LENGTH: 368
<212> TYPE: DNA
<213> ORGANISM: Homo sapiens

<400> SEQUENCE: 3

| | |
|---|---|
| gtgatccacc cgcgcgcacg ggccgtcctc tccgcgcggg gagacgcgcg catccaccag | 60 |
| ccccggctgc tcgccagccc cggccccagc catggaagag ctcacggctt ttgtatccaa | 120 |
| gtcttttgac cagaaaagca aggacggtaa cggcggaggc ggaggcggcg gaggtaagaa | 180 |
| ggattccatt acgtaccggg aagttttgga gagcggactg gcgcgctccc gggagctggg | 240 |
| gacgtcggat tccagcctcc aggacatcac ggagggcggc ggccactgcc cggtgcattt | 300 |
| gttcaaggac cacgtagaca atgacaagga gaaactgaaa gaattcggca ccgcgagagt | 360 |
| ggcagaag | 368 |

<210> SEQ ID NO 4
<211> LENGTH: 58
<212> TYPE: DNA
<213> ORGANISM: Homo sapiens

<400> SEQUENCE: 4

| | |
|---|---|
| gtttggttcc agaaccggag agccaagtgc cgcaaacaag agaatcagat gcataaag | 58 |

<210> SEQ ID NO 5
<211> LENGTH: 89
<212> TYPE: DNA
<213> ORGANISM: Homo sapiens

<400> SEQUENCE: 5

| | |
|---|---|
| gcgtcatctt gggcacagcc aaccacctag acgcctgccg agtggcaccc tacgtcaaca | 60 |
| tgggagcctt acggatgcct ttccaacag | 89 |

<210> SEQ ID NO 6
<211> LENGTH: 1166
<212> TYPE: DNA
<213> ORGANISM: Homo sapiens

<400> SEQUENCE: 6

| | |
|---|---|
| gtccaggctc agctgcagct ggaaggcgtg gcccacgcgc accgcacct gcacccgcac | 60 |
| ctggcggcgc acgcgcccta cctgatgttc ccccgccgc ccttcgggct gcccatcgcg | 120 |
| tcgctggccg agtccgcctc ggccgccgcc gtggtcgccg ccgccgccaa agcaacagc | 180 |
| aagaattcca gcatcgccga cctgcggctc aaggcgcgga agcacgcgga ggccctgggg | 240 |
| ctctgacccg ccgcgcagcc ccccgcgcgc ccggactccc gggctccgcg caccccgcct | 300 |
| gcaccgcgcg tcctgcactc aaccccgcct ggagctcctt ccgcggccac cgtgctccgg | 360 |
| gcaccccggg agctcctgca agaggcctga ggagggaggc tcccgggacc gtccacgcac | 420 |
| gacccagcca gaccctcgcg gagatggtgc agaaggcgga gcgggtgagc ggccgtgcgt | 480 |
| ccagcccggg cctctccaag gctgcccgtg cgtcctggga ccctggagaa gggtaaaccc | 540 |
| ccgcctggct gcgtcttcct ctgctatacc ctatgcatgc ggttaactac acacgtttgg | 600 |
| aagatcctta gagtctattg aaactgcaaa gatcccggag ctggtctccg atgaaaatgc | 660 |
| catttcttcg ttgccaacga ttttctttac taccatgctc cttccttcat cccgagaggc | 720 |
| tgcggaacgg gtgtggattt gaatgtggac ttcggaatcc caggaggcag ggccgggct | 780 |

```
ctcctccacc gctcccccgg agcctcccag gcagcaataa ggaaatagtt ctctggctga    840
ggctgaggac gtgaaccgcg ggctttggaa agggagggga gggagacccg aacctcccac    900
gttgggactc ccacgttccg gggacctgaa tgaggaccga ctttataact tttccagtgt    960
ttgattccca aattgggtct ggttttgttt tggattggta tttttttttt tttttttttt   1020
tgctgtgtta caggattcag acgcaaaaga cttgcataag agacggacgc gtggttgcaa   1080
ggtgtcatac tgatatgcag cattaacttt actgacatgg agtgaagtgc aatattataa   1140
atattataga ttaaaaaaaa aatagc                                        1166

<210> SEQ ID NO 7
<211> LENGTH: 625
<212> TYPE: DNA
<213> ORGANISM: Homo sapiens

<400> SEQUENCE: 7
atggagtttt gctcttgtcg cccaggctgg agtataatgg catgatctcg actcactgca     60
acctccgcct cccgagttca agcgattctc ctgcctcagc ctcccgagta gctgggatta    120
caggtgccca ccaccatgtc aagataatgt ttgtattttc agtagagatg gggtttgacc    180
atgttggcca ggctggtctc gaactcctga cctcaggtga tccacccgcc ttagcctccc    240
aaagtgctgg gattacaggc gtgagcccct gcgcccggcc tttgtaactt tattttta at    300 tttttttttt ttttaagaaa gacagagtct tgctctgtca cccaggctgg agcacactgg    360
tgcgatcata gctcactgca gcctcaaact cctgggctca agcaatcctc ccacctcagc    420
ctcctgagta gctgggacta caggcaccca ccaccacacc cagctaattt ttttgatttt    480
tactagagac gggatcttgc tttgctgctg aggctggtct tgagctcctg agctccaaag    540
atcctctcac ctccacctcc caaagtgtta gaattacaag catgaaccac tgcccgtggt    600
ctccaaaaaa aggactgtta cgtgg                                          625

<210> SEQ ID NO 8
<211> LENGTH: 15577
<212> TYPE: DNA
<213> ORGANISM: Homo sapiens
<220> FEATURE:
<221> NAME/KEY: misc_feature
<222> LOCATION: (3844)..(4068)
<223> OTHER INFORMATION: pET92 region (first part)
<220> FEATURE:
<221> NAME/KEY: misc_feature
<222> LOCATION: (4326)..(4437)
<223> OTHER INFORMATION: pET92 region (second part)
<220> FEATURE:
<221> NAME/KEY: misc_feature
<222> LOCATION: (4545)..(4619)
<223> OTHER INFORMATION: pET92 region (third region)
<220> FEATURE:
<221> NAME/KEY: misc_feature
<222> LOCATION: (5305)..(5512)
<223> OTHER INFORMATION: part of exon II (ET93)
<220> FEATURE:
<221> NAME/KEY: misc_feature
<222> LOCATION: (1498)..(1807)
<223> OTHER INFORMATION: part of exon I (G310)
<220> FEATURE:
<221> NAME/KEY: misc_feature
<222> LOCATION: (11620)..(11729)
<223> OTHER INFORMATION: part of exon IV (G108)
<220> FEATURE:
<221> NAME/KEY: misc_feature
<222> LOCATION: (2665)
<223> OTHER INFORMATION: a, c, t, g, other or unknown
<220> FEATURE:
```

-continued

```
<221> NAME/KEY: misc_feature
<222> LOCATION: (2880)
<223> OTHER INFORMATION: a, c, t, g, other or unknown
<220> FEATURE:
<221> NAME/KEY: misc_feature
<222> LOCATION: (3508)
<223> OTHER INFORMATION: a, c, t, g, other or unknown
<220> FEATURE:
<221> NAME/KEY: misc_feature
<222> LOCATION: (3529)
<223> OTHER INFORMATION: a, c, t, g, other or unknown
<220> FEATURE:
<221> NAME/KEY: misc_feature
<222> LOCATION: (3555)
<223> OTHER INFORMATION: a, c, t, g, other or unknown
<220> FEATURE:
<221> NAME/KEY: misc_feature
<222> LOCATION: (3578)
<223> OTHER INFORMATION: a, c, t, g, other or unknown
<220> FEATURE:
<221> NAME/KEY: misc_feature
<222> LOCATION: (3580)
<223> OTHER INFORMATION: a, c, t, g, other or unknown
<220> FEATURE:
<221> NAME/KEY: misc_feature
<222> LOCATION: (3592)
<223> OTHER INFORMATION: a, c, t, g, other or unknown
<220> FEATURE:
<221> NAME/KEY: misc_feature
<222> LOCATION: (3600)
<223> OTHER INFORMATION: a, c, t, g, other or unknown
<220> FEATURE:
<221> NAME/KEY: misc_feature
<222> LOCATION: (3606)
<223> OTHER INFORMATION: a, c, t, g, other or unknown
<220> FEATURE:
<221> NAME/KEY: misc_feature
<222> LOCATION: (3609)
<223> OTHER INFORMATION: a, c, t, g, other or unknown
<220> FEATURE:
<221> NAME/KEY: misc_feature
<222> LOCATION: (3619)
<223> OTHER INFORMATION: a, c, t, g, other or unknown
<220> FEATURE:
<221> NAME/KEY: misc_feature
<222> LOCATION: (3621)
<223> OTHER INFORMATION: a, c, t, g, other or unknown
<220> FEATURE:
<221> NAME/KEY: misc_feature
<222> LOCATION: (3643)
<223> OTHER INFORMATION: a, c, t, g, other or unknown
<220> FEATURE:
<221> NAME/KEY: misc_feature
<222> LOCATION: (3652)
<223> OTHER INFORMATION: a, c, t, g, other or unknown
<220> FEATURE:
<221> NAME/KEY: misc_feature
<222> LOCATION: (3681)..(3682)
<223> OTHER INFORMATION: a, c, t, g, other or unknown
<220> FEATURE:
<221> NAME/KEY: misc_feature
<222> LOCATION: (3729)
<223> OTHER INFORMATION: a, c, t, g, other or unknown
<220> FEATURE:
<221> NAME/KEY: misc_feature
<222> LOCATION: (3867)
<223> OTHER INFORMATION: a, c, t, g, other or unknown
<220> FEATURE:
<221> NAME/KEY: misc_feature
<222> LOCATION: (3965)
<223> OTHER INFORMATION: a, c, t, g, other or unknown
<220> FEATURE:
<221> NAME/KEY: misc_feature
<222> LOCATION: (4174)
<223> OTHER INFORMATION: a, c, t, g, other or unknown
<220> FEATURE:
<221> NAME/KEY: misc_feature
<222> LOCATION: (4212)
<223> OTHER INFORMATION: a, c, t, g, other or unknown
```

```
<220> FEATURE:
<221> NAME/KEY: misc_feature
<222> LOCATION: (4376)
<223> OTHER INFORMATION: a, c, t, g, other or unknown
<220> FEATURE:
<221> NAME/KEY: misc_feature
<222> LOCATION: (4389)
<223> OTHER INFORMATION: a, c, t, g, other or unknown
<220> FEATURE:
<221> NAME/KEY: misc_feature
<222> LOCATION: (4400)
<223> OTHER INFORMATION: a, c, t, g, other or unknown
<220> FEATURE:
<221> NAME/KEY: misc_feature
<222> LOCATION: (4403)
<223> OTHER INFORMATION: a, c, t, g, other or unknown
<220> FEATURE:
<221> NAME/KEY: misc_feature
<222> LOCATION: (4411)
<223> OTHER INFORMATION: a, c, t, g, other or unknown
<220> FEATURE:
<221> NAME/KEY: misc_feature
<222> LOCATION: (4417)
<223> OTHER INFORMATION: a, c, t, g, other or unknown
<220> FEATURE:
<221> NAME/KEY: misc_feature
<222> LOCATION: (4424)
<223> OTHER INFORMATION: a, c, t, g, other or unknown
<220> FEATURE:
<221> NAME/KEY: misc_feature
<222> LOCATION: (4444)
<223> OTHER INFORMATION: a, c, t, g, other or unknown
<220> FEATURE:
<221> NAME/KEY: misc_feature
<222> LOCATION: (4455)
<223> OTHER INFORMATION: a, c, t, g, other or unknown
<220> FEATURE:
<221> NAME/KEY: misc_feature
<222> LOCATION: (4460)
<223> OTHER INFORMATION: a, c, t, g, other or unknown
<220> FEATURE:
<221> NAME/KEY: misc_feature
<222> LOCATION: (4465)
<223> OTHER INFORMATION: a, c, t, g, other or unknown
<220> FEATURE:
<221> NAME/KEY: misc_feature
<222> LOCATION: (4469)
<223> OTHER INFORMATION: a, c, t, g, other or unknown
<220> FEATURE:
<221> NAME/KEY: misc_feature
<222> LOCATION: (4478)
<223> OTHER INFORMATION: a, c, t, g, other or unknown
<220> FEATURE:
<221> NAME/KEY: misc_feature
<222> LOCATION: (4490)
<223> OTHER INFORMATION: a, c, t, g, other or unknown
<220> FEATURE:
<221> NAME/KEY: misc_feature
<222> LOCATION: (4500)
<223> OTHER INFORMATION: a, c, t, g, other or unknown
<220> FEATURE:
<221> NAME/KEY: misc_feature
<222> LOCATION: (4509)
<223> OTHER INFORMATION: a, c, t, g, other or unknown
<220> FEATURE:
<221> NAME/KEY: misc_feature
<222> LOCATION: (4578)
<223> OTHER INFORMATION: a, c, t, g, other or unknown
<220> FEATURE:
<221> NAME/KEY: misc_feature
<222> LOCATION: (4586)
<223> OTHER INFORMATION: a, c, t, g, other or unknown
<220> FEATURE:
<221> NAME/KEY: misc_feature
<222> LOCATION: (4616)
<223> OTHER INFORMATION: a, c, t, g, other or unknown
<220> FEATURE:
<221> NAME/KEY: misc_feature
<222> LOCATION: (4687)
```

-continued

```
<223> OTHER INFORMATION: a, c, t, g, other or unknown
<220> FEATURE:
<221> NAME/KEY: misc_feature
<222> LOCATION: (4695)..(4696)
<223> OTHER INFORMATION: a, c, t, g, other or unknown
<220> FEATURE:
<221> NAME/KEY: misc_feature
<222> LOCATION: (4710)
<223> OTHER INFORMATION: a, c, t, g, other or unknown
<220> FEATURE:
<221> NAME/KEY: misc_feature
<222> LOCATION: (4738)
<223> OTHER INFORMATION: a, c, t, g, other or unknown
<220> FEATURE:
<221> NAME/KEY: misc_feature
<222> LOCATION: (4743)
<223> OTHER INFORMATION: a, c, t, g, other or unknown
<220> FEATURE:
<221> NAME/KEY: misc_feature
<222> LOCATION: (4750)
<223> OTHER INFORMATION: a, c, t, g, other or unknown
<220> FEATURE:
<221> NAME/KEY: misc_feature
<222> LOCATION: (4754)
<223> OTHER INFORMATION: a, c, t, g, other or unknown
<220> FEATURE:
<221> NAME/KEY: misc_feature
<222> LOCATION: (6252)
<223> OTHER INFORMATION: a, c, t, g, other or unknown
<220> FEATURE:
<221> NAME/KEY: misc_feature
<222> LOCATION: (6415)
<223> OTHER INFORMATION: a, c, t, g, other or unknown
<220> FEATURE:
<221> NAME/KEY: misc_feature
<222> LOCATION: (7768)
<223> OTHER INFORMATION: a, c, t, g, other or unknown
<220> FEATURE:
<221> NAME/KEY: misc_feature
<222> LOCATION: (7836)
<223> OTHER INFORMATION: a, c, t, g, other or unknown
<220> FEATURE:
<221> NAME/KEY: misc_feature
<222> LOCATION: (7847)
<223> OTHER INFORMATION: a, c, t, g, other or unknown
<220> FEATURE:
<221> NAME/KEY: misc_feature
<222> LOCATION: (7854)
<223> OTHER INFORMATION: a, c, t, g, other or unknown
<220> FEATURE:
<221> NAME/KEY: misc_feature
<222> LOCATION: (7870)..(7871)
<223> OTHER INFORMATION: a, c, t, g, other or unknown
<220> FEATURE:
<221> NAME/KEY: misc_feature
<222> LOCATION: (7882)..(7884)
<223> OTHER INFORMATION: a, c, t, g, other or unknown
<220> FEATURE:
<221> NAME/KEY: misc_feature
<222> LOCATION: (7893)
<223> OTHER INFORMATION: a, c, t, g, other or unknown
<220> FEATURE:
<221> NAME/KEY: misc_feature
<222> LOCATION: (7903)..(7904)
<223> OTHER INFORMATION: a, c, t, g, other or unknown
<220> FEATURE:
<221> NAME/KEY: misc_feature
<222> LOCATION: (7910)
<223> OTHER INFORMATION: a, c, t, g, other or unknown
<220> FEATURE:
<221> NAME/KEY: misc_feature
<222> LOCATION: (7918)..(7919)
<223> OTHER INFORMATION: a, c, t, g, other or unknown
<220> FEATURE:
<221> NAME/KEY: misc_feature
<222> LOCATION: (7927)
<223> OTHER INFORMATION: a, c, t, g, other or unknown
<220> FEATURE:
<221> NAME/KEY: misc_feature
```

```
<222> LOCATION: (7932)..(7934)
<223> OTHER INFORMATION: a, c, t, g, other or unknown
<220> FEATURE:
<221> NAME/KEY: misc_feature
<222> LOCATION: (7944)
<223> OTHER INFORMATION: a, c, t, g, other or unknown
<220> FEATURE:
<221> NAME/KEY: misc_feature
<222> LOCATION: (7951)..(7952)
<223> OTHER INFORMATION: a, c, t, g, other or unknown
<220> FEATURE:
<221> NAME/KEY: misc_feature
<222> LOCATION: (7955)
<223> OTHER INFORMATION: a, c, t, g, other or unknown
<220> FEATURE:
<221> NAME/KEY: misc_feature
<222> LOCATION: (7961)
<223> OTHER INFORMATION: a, c, t, g, other or unknown
<220> FEATURE:
<221> NAME/KEY: misc_feature
<222> LOCATION: (7966)
<223> OTHER INFORMATION: a, c, t, g, other or unknown
<220> FEATURE:
<221> NAME/KEY: misc_feature
<222> LOCATION: (7971)
<223> OTHER INFORMATION: a, c, t, g, other or unknown
<220> FEATURE:
<221> NAME/KEY: misc_feature
<222> LOCATION: (7980)
<223> OTHER INFORMATION: a, c, t, g, other or unknown
<220> FEATURE:
<221> NAME/KEY: misc_feature
<222> LOCATION: (7983)
<223> OTHER INFORMATION: a, c, t, g, other or unknown
<220> FEATURE:
<221> NAME/KEY: misc_feature
<222> LOCATION: (7990)
<223> OTHER INFORMATION: a, c, t, g, other or unknown
<220> FEATURE:
<221> NAME/KEY: misc_feature
<222> LOCATION: (7996)
<223> OTHER INFORMATION: a, c, t, g, other or unknown
<220> FEATURE:
<221> NAME/KEY: misc_feature
<222> LOCATION: (8031)
<223> OTHER INFORMATION: a, c, t, g, other or unknown
<220> FEATURE:
<221> NAME/KEY: misc_feature
<222> LOCATION: (8035)
<223> OTHER INFORMATION: a, c, t, g, other or unknown
<220> FEATURE:
<221> NAME/KEY: misc_feature
<222> LOCATION: (8043)..(8044)
<223> OTHER INFORMATION: a, c, t, g, other or unknown
<220> FEATURE:
<221> NAME/KEY: misc_feature
<222> LOCATION: (8051)
<223> OTHER INFORMATION: a, c, t, g, other or unknown
<220> FEATURE:
<221> NAME/KEY: misc_feature
<222> LOCATION: (8061)
<223> OTHER INFORMATION: a, c, t, g, other or unknown
<220> FEATURE:
<221> NAME/KEY: misc_feature
<222> LOCATION: (8064)
<223> OTHER INFORMATION: a, c, t, g, other or unknown
<220> FEATURE:
<221> NAME/KEY: misc_feature
<222> LOCATION: (8074)
<223> OTHER INFORMATION: a, c, t, g, other or unknown
<220> FEATURE:
<221> NAME/KEY: misc_feature
<222> LOCATION: (8077)
<223> OTHER INFORMATION: a, c, t, g, other or unknown
<220> FEATURE:
<221> NAME/KEY: misc_feature
<222> LOCATION: (8089)..(8090)
<223> OTHER INFORMATION: a, c, t, g, other or unknown
<220> FEATURE:
```

-continued

```
<221> NAME/KEY: misc_feature
<222> LOCATION: (8096)..(8097)
<223> OTHER INFORMATION: a, c, t, g, other or unknown
<220> FEATURE:
<221> NAME/KEY: misc_feature
<222> LOCATION: (8106)
<223> OTHER INFORMATION: a, c, t, g, other or unknown
<220> FEATURE:
<221> NAME/KEY: misc_feature
<222> LOCATION: (8115)
<223> OTHER INFORMATION: a, c, t, g, other or unknown
<220> FEATURE:
<221> NAME/KEY: misc_feature
<222> LOCATION: (8143)..(8144)
<223> OTHER INFORMATION: a, c, t, g, other or unknown
<220> FEATURE:
<221> NAME/KEY: misc_feature
<222> LOCATION: (8159)
<223> OTHER INFORMATION: a, c, t, g, other or unknown
<220> FEATURE:
<221> NAME/KEY: misc_feature
<222> LOCATION: (8181)..(8182)
<223> OTHER INFORMATION: a, c, t, g, other or unknown
<220> FEATURE:
<221> NAME/KEY: misc_feature
<222> LOCATION: (8623)
<223> OTHER INFORMATION: a, c, t, g, other or unknown
<220> FEATURE:
<221> NAME/KEY: misc_feature
<222> LOCATION: (8629)
<223> OTHER INFORMATION: a, c, t, g, other or unknown
<220> FEATURE:
<221> NAME/KEY: misc_feature
<222> LOCATION: (8639)..(8640)
<223> OTHER INFORMATION: a, c, t, g, other or unknown
<220> FEATURE:
<221> NAME/KEY: misc_feature
<222> LOCATION: (8651)
<223> OTHER INFORMATION: a, c, t, g, other or unknown
<220> FEATURE:
<221> NAME/KEY: misc_feature
<222> LOCATION: (8658)
<223> OTHER INFORMATION: a, c, t, g, other or unknown
<220> FEATURE:
<221> NAME/KEY: misc_feature
<222> LOCATION: (8667)..(8668)
<223> OTHER INFORMATION: a, c, t, g, other or unknown
<220> FEATURE:
<221> NAME/KEY: misc_feature
<222> LOCATION: (8672)
<223> OTHER INFORMATION: a, c, t, g, other or unknown
<220> FEATURE:
<221> NAME/KEY: misc_feature
<222> LOCATION: (8683)
<223> OTHER INFORMATION: a, c, t, g, other or unknown
<220> FEATURE:
<221> NAME/KEY: misc_feature
<222> LOCATION: (8697)
<223> OTHER INFORMATION: a, c, t, g, other or unknown
<220> FEATURE:
<221> NAME/KEY: misc_feature
<222> LOCATION: (8701)..(8702)
<223> OTHER INFORMATION: a, c, t, g, other or unknown
<220> FEATURE:
<221> NAME/KEY: misc_feature
<222> LOCATION: (8750)
<223> OTHER INFORMATION: a, c, t, g, other or unknown
<220> FEATURE:
<221> NAME/KEY: misc_feature
<222> LOCATION: (8756)
<223> OTHER INFORMATION: a, c, t, g, other or unknown
<220> FEATURE:
<221> NAME/KEY: misc_feature
<222> LOCATION: (8765)..(8766)
<223> OTHER INFORMATION: a, c, t, g, other or unknown
<220> FEATURE:
<221> NAME/KEY: misc_feature
<222> LOCATION: (8775)..(8776)
<223> OTHER INFORMATION: a, c, t, g, other or unknown
```

-continued

```
<220> FEATURE:
<221> NAME/KEY: misc_feature
<222> LOCATION: (8787)
<223> OTHER INFORMATION: a, c, t, g, other or unknown
<220> FEATURE:
<221> NAME/KEY: misc_feature
<222> LOCATION: (8794)
<223> OTHER INFORMATION: a, c, t, g, other or unknown
<220> FEATURE:
<221> NAME/KEY: misc_feature
<222> LOCATION: (8804)
<223> OTHER INFORMATION: a, c, t, g, other or unknown
<220> FEATURE:
<221> NAME/KEY: misc_feature
<222> LOCATION: (8815)
<223> OTHER INFORMATION: a, c, t, g, other or unknown
<220> FEATURE:
<221> NAME/KEY: misc_feature
<222> LOCATION: (8820)..(8821)
<223> OTHER INFORMATION: a, c, t, g, other or unknown
<220> FEATURE:
<221> NAME/KEY: misc_feature
<222> LOCATION: (8825)
<223> OTHER INFORMATION: a, c, t, g, other or unknown
<220> FEATURE:
<221> NAME/KEY: misc_feature
<222> LOCATION: (8835)
<223> OTHER INFORMATION: a, c, t, g, other or unknown
<220> FEATURE:
<221> NAME/KEY: misc_feature
<222> LOCATION: (8840)..(8841)
<223> OTHER INFORMATION: a, c, t, g, other or unknown
<220> FEATURE:
<221> NAME/KEY: misc_feature
<222> LOCATION: (8854)..(8857)
<223> OTHER INFORMATION: a, c, t, g, other or unknown
<220> FEATURE:
<221> NAME/KEY: misc_feature
<222> LOCATION: (8876)..(8877)
<223> OTHER INFORMATION: a, c, t, g, other or unknown
<220> FEATURE:
<221> NAME/KEY: misc_feature
<222> LOCATION: (8886)..(8887)
<223> OTHER INFORMATION: a, c, t, g, other or unknown
<220> FEATURE:
<221> NAME/KEY: misc_feature
<222> LOCATION: (8996)
<223> OTHER INFORMATION: a, c, t, g, other or unknown
<220> FEATURE:
<221> NAME/KEY: misc_feature
<222> LOCATION: (9007)
<223> OTHER INFORMATION: a, c, t, g, other or unknown
<220> FEATURE:
<221> NAME/KEY: misc_feature
<222> LOCATION: (9124)
<223> OTHER INFORMATION: a, c, t, g, other or unknown
<220> FEATURE:
<221> NAME/KEY: misc_feature
<222> LOCATION: (9155)
<223> OTHER INFORMATION: a, c, t, g, other or unknown
<220> FEATURE:
<221> NAME/KEY: misc_feature
<222> LOCATION: (9162)
<223> OTHER INFORMATION: a, c, t, g, other or unknown
<220> FEATURE:
<221> NAME/KEY: misc_feature
<222> LOCATION: (9176)..(9177)
<223> OTHER INFORMATION: a, c, t, g, other or unknown
<220> FEATURE:
<221> NAME/KEY: misc_feature
<222> LOCATION: (9243)
<223> OTHER INFORMATION: a, c, t, g, other or unknown
<220> FEATURE:
<221> NAME/KEY: misc_feature
<222> LOCATION: (9607)
<223> OTHER INFORMATION: a, c, t, g, other or unknown
<220> FEATURE:
<221> NAME/KEY: misc_feature
<222> LOCATION: (9612)
```

-continued

```
<223> OTHER INFORMATION: a, c, t, g, other or unknown
<220> FEATURE:
<221> NAME/KEY: misc_feature
<222> LOCATION: (11335)
<223> OTHER INFORMATION: a, c, t, g, other or unknown
<220> FEATURE:
<221> NAME/KEY: misc_feature
<222> LOCATION: (11431)
<223> OTHER INFORMATION: a, c, t, g, other or unknown
<220> FEATURE:
<221> NAME/KEY: misc_feature
<222> LOCATION: (11447)
<223> OTHER INFORMATION: a, c, t, g, other or unknown
<220> FEATURE:
<221> NAME/KEY: misc_feature
<222> LOCATION: (11472)
<223> OTHER INFORMATION: a, c, t, g, other or unknown
<220> FEATURE:
<221> NAME/KEY: misc_feature
<222> LOCATION: (11658)
<223> OTHER INFORMATION: a, c, t, g, other or unknown
<220> FEATURE:
<221> NAME/KEY: misc_feature
<222> LOCATION: (11732)
<223> OTHER INFORMATION: a, c, t, g, other or unknown
<220> FEATURE:
<221> NAME/KEY: misc_feature
<222> LOCATION: (12690)
<223> OTHER INFORMATION: a, c, t, g, other or unknown
<220> FEATURE:
<221> NAME/KEY: misc_feature
<222> LOCATION: (12697)
<223> OTHER INFORMATION: a, c, t, g, other or unknown
<220> FEATURE:
<221> NAME/KEY: misc_feature
<222> LOCATION: (12701)
<223> OTHER INFORMATION: a, c, t, g, other or unknown
<220> FEATURE:
<221> NAME/KEY: misc_feature
<222> LOCATION: (12716)
<223> OTHER INFORMATION: a, c, t, g, other or unknown
<220> FEATURE:
<221> NAME/KEY: misc_feature
<222> LOCATION: (12778)
<223> OTHER INFORMATION: a, c, t, g, other or unknown
<220> FEATURE:
<221> NAME/KEY: misc_feature
<222> LOCATION: (12785)
<223> OTHER INFORMATION: a, c, t, g, other or unknown
<220> FEATURE:
<221> NAME/KEY: misc_feature
<222> LOCATION: (12795)
<223> OTHER INFORMATION: a, c, t, g, other or unknown
<220> FEATURE:
<221> NAME/KEY: misc_feature
<222> LOCATION: (12803)
<223> OTHER INFORMATION: a, c, t, g, other or unknown
<220> FEATURE:
<221> NAME/KEY: misc_feature
<222> LOCATION: (12816)
<223> OTHER INFORMATION: a, c, t, g, other or unknown
<220> FEATURE:
<221> NAME/KEY: misc_feature
<222> LOCATION: (12848)
<223> OTHER INFORMATION: a, c, t, g, other or unknown
<220> FEATURE:
<221> NAME/KEY: misc_feature
<222> LOCATION: (12857)
<223> OTHER INFORMATION: a, c, t, g, other or unknown
<220> FEATURE:
<221> NAME/KEY: misc_feature
<222> LOCATION: (13192)
<223> OTHER INFORMATION: a, c, t, g, other or unknown
<220> FEATURE:
<221> NAME/KEY: misc_feature
<222> LOCATION: (13867)
<223> OTHER INFORMATION: a, c, t, g, other or unknown
<220> FEATURE:
<221> NAME/KEY: misc_feature
```

```
<222> LOCATION: (13872)
<223> OTHER INFORMATION: a, c, t, g, other or unknown
<220> FEATURE:
<221> NAME/KEY: misc_feature
<222> LOCATION: (13876)
<223> OTHER INFORMATION: a, c, t, g, other or unknown
<220> FEATURE:
<221> NAME/KEY: misc_feature
<222> LOCATION: (13881)
<223> OTHER INFORMATION: a, c, t, g, other or unknown
<220> FEATURE:
<221> NAME/KEY: misc_feature
<222> LOCATION: (13926)..(13927)
<223> OTHER INFORMATION: a, c, t, g, other or unknown
<220> FEATURE:
<221> NAME/KEY: misc_feature
<222> LOCATION: (13990)
<223> OTHER INFORMATION: a, c, t, g, other or unknown
<220> FEATURE:
<221> NAME/KEY: misc_feature
<222> LOCATION: (13998)
<223> OTHER INFORMATION: a, c, t, g, other or unknown
<220> FEATURE:
<221> NAME/KEY: misc_feature
<222> LOCATION: (14106)
<223> OTHER INFORMATION: a, c, t, g, other or unknown
<220> FEATURE:
<221> NAME/KEY: misc_feature
<222> LOCATION: (14193)
<223> OTHER INFORMATION: a, c, t, g, other or unknown
<220> FEATURE:
<221> NAME/KEY: misc_feature
<222> LOCATION: (14234)
<223> OTHER INFORMATION: a, c, t, g, other or unknown
<220> FEATURE:
<221> NAME/KEY: misc_feature
<222> LOCATION: (14269)
<223> OTHER INFORMATION: a, c, t, g, other or unknown
<220> FEATURE:
<221> NAME/KEY: misc_feature
<222> LOCATION: (14296)
<223> OTHER INFORMATION: a, c, t, g, other or unknown
<220> FEATURE:
<221> NAME/KEY: misc_feature
<222> LOCATION: (14538)
<223> OTHER INFORMATION: a, c, t, g, other or unknown
<220> FEATURE:
<221> NAME/KEY: misc_feature
<222> LOCATION: (14967)
<223> OTHER INFORMATION: a, c, t, g, other or unknown
<220> FEATURE:
<221> NAME/KEY: misc_feature
<222> LOCATION: (15027)
<223> OTHER INFORMATION: a, c, t, g, other or unknown
<220> FEATURE:
<221> NAME/KEY: misc_feature
<222> LOCATION: (15031)
<223> OTHER INFORMATION: a, c, t, g, other or unknown
<220> FEATURE:
<221> NAME/KEY: misc_feature
<222> LOCATION: (15064)
<223> OTHER INFORMATION: a, c, t, g, other or unknown
<220> FEATURE:
<221> NAME/KEY: misc_feature
<222> LOCATION: (15078)
<223> OTHER INFORMATION: a, c, t, g, other or unknown

<400> SEQUENCE: 8
ctctccctgt tgtgtctctc tttctctctc tccatctctc tccgtctttc ccctctgtc      60 tctttctctg tctccatccc tctgtctctc cctttctctc tgtctttcct tgtctctctc     120
tttctctctc tctctccatc tctctctctc ccggtctctc tctctccatc tccccgtctc     180
tccgtttctc tctctgcctc tccctgtctg tctctctctt tgtgtgtgtt acacacaccc     240
caacccaccg tcactcatgt cccccccactg ctgtgccatc tcacacaagt tcacagctca    300
```

```
gctgtcatcc tgggtcccca ggccccgccg gggaggaaga tgcgccgtgg ggttacggga    360
ggaaggggac tccgggcctc ctggtgcccc actttatttg cagaaggtcc ttggcaggaa    420
ccgtgacgcg tttggtttcc aggacttgga aaacgaattt caggtcgcga tggcgagcac    480
cggcttcccc tgaagcacat tcaatagcga gaggcgggag ggagcgagca ggagcatccc    540
accatgaaaa ccaaaaacac aagtattttt ttcacccggt aaatacccca gacgccaggg    600
tgacagcgcg gcgctaaggg aggaggcctc gcgccgggtt ccgccgggat ctggcgcggg    660
cggaaagaat atagatcttt acgaaccgga tctcccgggg acctgggctt ctttctgcgg    720
gcgctggaaa cccgggaggc ggccccgggg atcctcggcc tccgccgccg ccgcctccca    780 agccgcccgcg tcccggtttg gggacacccg gccccttctt ctcactttcg gggattctcc    840
agccgcgttc catctcacca actctccatc aagggcgcg ccgccaccaa cttgagctc     900 atcttctccc aaaatcgtgc gtccccgggg cgcccgggtc ccccccctcg ccatctcaac    960 cccgcgcga cccgggcgct tcctggaaag atccaggcgc cgggctctgc gctcctcccg   1020
ggagcgaggg cggccggaca actgggaccc tcctctctcc agccgtgaac tccttgtctc   1080
tctgtctctc tctgcaggaa aactggagtt tgcttttcct ccggccacgg aaagaacgcg   1140
ggtaacctgt gtgggggct cgggcgcctg cgccccctc ctgcgcgcgc gctctccctt   1200
ccaaaaatgg gatctttccc ccttcgcacc aaggtgtacg gacgccaaac agtgatgaaa   1260
tgagaagaaa gccaattgcc ggcctggggg gtggggggaga cacagcgtct ctgcgtgcgt   1320
ccgccgcgga gcccggagac cagtaattgc accagacagg cagcgcatgg ggggctgggc   1380
gaggtcgccg cgtataaata gtgagatttc caatggaaag gcgtaaataa cagcgctggt   1440
gatccacccg cgcgcacggg ccgtcctctc cgcgcgggga gacgcgcgca tccaccagcc   1500
ccggctgctc gccagccccg gccccagcca tggaagagct cacggctttt gtatccaagt   1560
cttttgacca gaaaagcaag gacggtaacg cgcgaggcgg aggcggcgga ggtaagaagg   1620
attccattac gtaccgggaa gttttggaga gcggactggc gcgctcccgg gagctgggga   1680
cgtcggattc cagcctccag gacatcacgg agggcggcgg ccactgcccg gtgcatttgt   1740
tcaaggacca cgtagacaat gacaaggaga aactgaaaga attcggcacc gcgagagtgg   1800
cagaaggtaa gttcctttgc gcgccggctc caggggggcc ctcctggggt tcggcgcctc   1860
ctcgccacgg agtcggcccc gcgcgcccct cgctgtgcac atttgcagct cccgtctcgc   1920
cagggtaagg cccgggccgt caggctttgc ctaagaaagg aaggaaggca ggagtggacc   1980
cgaccggaga cgcgggtggt gggtagcggg gtgcggggggg acccagggag ggtcgcagcg   2040
ggggccgcgc gcgtgggcac cgacacggga aggtcccggg ctggggtgga tccgggtggc   2100
tgtgcctgaa gccgtagggc ctgagatgtc ttttcattt tctttttctt tcctttcctt   2160
tttttgtttg tttgtttgtt tgtttgagac agagtctcgc tctgtccccc aggctggagt   2220
gcagtggtgc gatctcggct cactgcaacc tccgcctcct gggttcaagc gattctcctg   2280
cctcagcctc cccagtagct gggattacag gcatgcacca ccacgcctgg ctaattttg   2340 tgcttttagt aaagacgggg attcaccatg ttggccaggc tggtctcgaa ctcctgacct   2400
caggtgatcc acccgcctcg gcctcccaaa gtgctggat gacaggcgtg aggcaccgcg   2460
cccggcctgg gtcctgacgg cttaggatgt gtgtttctgt ctctgcctgt ctgccttgta   2520
tttacggtca cccagacgca cagaggagcc gtctccacgc gccttcccag cgctcagcgc   2580
ctgccgggcc cccggagatc acgggaagac tcgaggctgc gtggtaggag acggaaggc    2640 cccgggtcag ctcggttctg tttcnctta aggaacccctt cattattatt tcattgtttt   2700
```

```
cctttgaacg tcgaggcttg atcttggcga aagctgttgg gtccataaaa accactcccg    2760
tgagcggagg tggccgggat ctggatgggg cgcgaggggc cccggggaag ctggcggctt    2820
cgcgggcgcg tcctaagtca aggttgtcag agcgcagccg gttgtgcgcg gcccgggggn    2880
agctcccctc tggcccttcc tcctgagacc tcagtggtgg gtcgtcccgt ggtggaaatc    2940
ggggagtaag aggctcagag agaggggctg gccccgggga tctctgtgca cacacgacaa    3000
ctgggcggca tacatcttaa gaataaaatg ggctggctgt gtcgggcac agctggagac    3060
ggctatggac gcctgttatg ttttcattac aaagacgcag agaatctagc ctcggctttt    3120
gctgattcgc aaagttgagg tgcgaggggtg aatgccccaa aggtaattct tcctaagact    3180
ctggggctac ctgctctccg ggccctgca tttggggtgt ggagtggccc cgggaaatag    3240
cccttgtatt cgtaggaggc accaggcagc ttcccaaggc cctgactttg tcgaagcaga    3300
aagctgtggc tacggtttac aaagcagtcc ccggtttctg accgtctaag aggcaggagc    3360
ccagcctgcc tttgacagtg agaggagttc ctccctacac actgctgcgg gcacccggca    3420
ctgtaattca tacacagaga gttggccttc ctggacgcaa ggctgggagc cgcttgaggg    3480
cctgcgtgta atttaagagg gttcgcangc gcccggcggc cgcttctgnt ggggttgctt    3540
tttggttgtc cttcngcaaa caccgttttg ctccctctngn aactctctct tnctcccccn    3600
tggccngtng gacccgggna ngagcaaagt gtcctccaga ccnttttgaa angtgagagg    3660
aaaataaaga ccaggccaaa nngacccagg gccacaggag aggagacaga gagtccccgt    3720
tacattttnc cccttggctg ggtgcagaaa gaccccgggg ccaggactgc cacccaggct    3780
actatttatt catcagatcc aagttaaatc gaggttggag ggcaggggag agtctgaggt    3840
taccgtggaa gcctggagtt tttgggnaac agcgtgtccc cgccgagcct gggagcccgt    3900
gggttctgca aagcctgcgg gtgtttgagg actttgaaga ccagtttgtc agttgggctc    3960
aattncctgg ggttcagact tagagaaatg aaggaggggag agctgggtc gtctccagga    4020
aacgattcac ttgggggggaa ggaatggagt gttcttgcag gcacatgtct gttaggaggt    4080
gaaacagaat gtgaaatcca cgttggagta agcgtccagc gctgaatgta gctcggggtg    4140
gggtgggagg gccctggtgt ggatcgtgga aggnaagaaa gacagaacag ggtgctagta    4200
tttacccccgt tnccctgtag acaccctgga tttgtcagct ttgcaagctt cttggttgca    4260
gcggccttgc ctgtgcccct ttgagactgt ttccagacta aacttccaaa tgtcagcccc    4320
ttacccttga cagcaaggga catctcatta gggcatcgcg tgcttctcat ctgtgnctca    4380
gcaggcccng agataggaan cangaggggc ngttggnaga tgcncacttc caccagccct    4440
gggnttgaag gggangcgan gggangacna ccttttanct taaacccctn gagcttggtn    4500
cagagaggnc tgaatgtcta aaatgaggaa gaaaaggttt ttcacctgga aacgcttgag    4560
ggctgagtct tctgcccntt ctgacntccc ccagcaaata cagacaggtc accaanctac    4620
tggagatgag aaagtgccat ttttggcaca ctctggtggg gtaggtgccc gaccgcgtgt    4680
gaaaaangtg ggaanggag agatttctgn cgcacgcgt tcagcccccca ggcgcggntg    4740
gcngcattcn aggntactca gacgcggttc tgctgttctg ctgagaaaca ggcttcgggt    4800
aggggctcct agctccgcca gatcgcggag ggaccccag ccctcctgcg ctgcagcggt    4860
ggggatagcg tctctccgta ggcctagaat ctgcaacccg ccccgggtcc tccccgtgtc    4920
cttcccgggc gtcccgccgg ggatcccaca gttggcagct cttcctcaaa ttctttccct    4980
taaaaatagg atttgacacc ccactctcct taaaaaaaaa aaataagaaa aaaggttag    5040
```

```
gttatgtcaa cagaggtgaa gtggataatt gaggaaacga ttctgagatg aggccaagaa      5100
aacaacgctc gtgcaaagcc caggttttg ggaaagcagc gagtatcctc ctcggctttt       5160
gcgttatgga ccccacgcag tttttgcgtc aaagcgcatt ggttttcgag ggccccttt       5220 ccaccgcggg atgcacgaag gggttcgcca cgttgcgcaa aacctcccg gcctcagccc       5280 tgtgccctcc gctccccacg cagggattta tgaatgcaaa gagaagcgcg aggacgtgaa      5340
gtcggaggac gaggacgggc agaccaagct gaaacagagg cgcagccgca ccaacttcac      5400
gctggagcag ctgaacgagc tcgagcgact ttttgacgag acccattacc ccgacgcctt     5460
catgcgcgag gagctcagcc agcgcctggg gctttccgag gcgcgcgtgc aggtaggaac      5520 ccggggcgg gggcggggg cccggagcca tcgcctggtc ctcgggagcg cacagcacgc       5580
gtacagccac ctgcgcccgg gccgccgccg tccccttccc ggagcgcggg gaggttgggt     5640
gagggacggg ctggggttcc tggacttttg gagacgcctg aggcctgtag gatgggttca     5700
ttgcgtttgt ttttcaccaa cagcaaacaa atatatatac atatatatta tacaaataac     5760
aaataaatat atatgttata cagatgggta tattgtatat attatagata tttgttcgtc     5820
cttggtgcaa agacacccgg tgaacccata tattggctcc tgactgcctt cggttcccct     5880
gggattggtt ataggggcaa cacatgcaaa caaaactttc cctggattat acttaggaga     5940
cgaagctaca gatgcgtttg atccagagtg ttttacaaga ttttttcattt aaaaaaaat     6000 gtgtcttttg gccctgatt cccctccgtc ttcccgtgtg gctgcattga aaaggtttcc      6060
ttaggatgaa aggagagggg tgtcctctgt ccctaggtgg agagaaacag ggtcttctct     6120
ttcctccgtt ttttcaccta ccgtttctat ctccctcctc ccctctccag ccctgtcctc    6180
tgctacaaac caccccctcc tccctccggc tgtggggagc gcaggagcac gttgggcatc     6240
tggatgagcg gnagactatt agcggggcac gggggctccc cgaggagcgc gcgaattcac     6300
gctgccccat gagaccaggc accgggggc ggaggggcct tgggtgtccg cagagggacg     6360
ggcgggcaga gccttcctcc gcattctaaa cattcactta aaggtatgag tttantttca    6420
ggggtgctgc tgggagagcc tccaaatggc ttcttccagc ccctgcctga cagttcagct    6480
cccctggaag gtcaactcct ctagtccttt ctcctggttc tgggcaggac agaagtgggg     6540
ggagggagag agagagagag agagagagag acggtcagga tccccggacc ctggggaacc    6600
cgtcaaaaat aaatgaaatt aagattgccg accagagaga gaaccgtgac aaagcaaacg    6660
gcgttcaaag caaagagacg aactgaaagc ccgttcccgt aggactggtt atgaggtcaa    6720
cacattcaaa cacagcttgc tctggatttt gctgagcaga ggaagataca gatgcatttg    6780
atccaaagtg tgttacatct ttcattatat gtgtgtctat atatataaac atatataaat    6840
atataaacat acataaatgt atgtaaatat atataatcta tatacatata taaatatata    6900
aacacatata taatatataa atctataaac atatataata tataaacata aatatataaa    6960
catatataat atataaatat attaacatat ataaaatatg tataaatata tataaacata    7020
taaacatata taaatatata aacatataaa tatataaaca tataaaata tatacaaaca    7080 tattgtatat atataaatat atataaaaac atatatatac atataaaaat atatataaac    7140
atatatacat ataagaaat atatataaac atatatacat ataaatatac atatataaac    7200
atatatacat atataaataata tataaacata tacatata aaaatatata tatattaaca    7260
tatatataca tataaaaata tatatattaa catatatata catataaaaa tatatatata    7320 ttttggccc ctgattccct tcggttcctg tgggatgggt gattgagtca acacattcaa     7380
acacaacttt tccatcgatg ttgcttagga gatgaggata cagatgcgtt tgatggagag    7440
```

```
ggttttacaa gctctttcat ttaaatatat atatatatat atatatattt tttggctcct   7500
gattctcttc cgtcttccca tgtggctgca ttttaaaagg cttccctaag atcgttacga   7560
ttaaatcaac cctccccagg catctttacc gagggctgtg gtcccaaag cgatacagcc    7620
caggagggag agaggctttg gtgacttgga ggaaggactg tgtccctcct tagggcgtct   7680
gtggcctcag tgagggaagg aagctgcatc agacaggggt ttcctcgctg tccacccctc   7740
tggcagaaga tggattgggc tgccccgnta taaattaatg aaaagattaa agtttcgcta   7800
aaggggacat cgagtttatg tgtcatctcc tggtgntctg tgtgccntgg gatnctgcaa   7860
tatatcccan ngcccttgat gnnntactgt ttnctataaa aanntaaatn tacttgtnna   7920
atttaanttc cnnnacacta tttncttttcc nngtnagtct nattanccga ncgagagcan  7980
cgnttagttn cagctngcgg aaaattggtt gtggggtgtg tgcggacccc ngagnaacgc   8040
ccnntaaaat naaagacaaa ntcgggggac aagnctnggg ggttatcgnn attgcnnagg   8100
ggtcgncatg aaaantttaa cgacggtaaa taataataaa aanncaaaca tgggaatgnc   8160
aataaaagac ataattctcc nnatcgccgc gggggaaag gatcctatag taaaggcgag    8220
tgcgctttga ggggtcataa aaatcaatta gttccaacac ccacgtcccg cgttgagggg   8280
acggggacga gcaggacag aaaaagaaac catatttgaa tcccatctct ctgtgaattc     8340
ttgggtcaca tgcgtctcag tacagcccgt cccgtgctgt gaccggatag agtttcaatt   8400
tactgtggaa atttgctgta aataaattga gcatccgata gaagctgttg ctgattaacc   8460
ttttatttt agcgtggccc tgcaaagtcg tatcacccag ctgtcaggct tctaatcgaa    8520
agttatgaga ccacggtgag gggcaggcgg taatttaatt acaacaaata tctttgggtt   8580
tatggcgcag agctaaatta aatgtcatta ttcactgtct gtnaatggna aatcaaaann   8640
ggaaatcgca nttacggnca tttgggnnaa angaaagcgg ggnagtgctc tttaatngaa   8700
nngaaataac tgtcttaagc agtgtcacac acttcactta ccatattcgn ggcctnaatt   8760
ggaanntgga tcgtnngaat cactccnaag actngattta ttangcgctt cacgncagcn   8820
nggcntaatt catcnacttn ngtattcttc atcnnnnatt tttttttttc ctctcnngcc   8880
gtgttnngaa gggagagtga atgaggcttt ccacgtttca ggaggatttt cttttttgaa   8940
aaatgccctt ccagaggctt ttgggtggct ggcttgcttt ctgggccctg gaggangaca   9000
ggcggangag tccaggtggg catggagagg cacagtggca ggtcacctgg atggtcagtg   9060
gaggtggagg tctgaaggcg ccagctttgg aaattattgg tgaatttcga tgtcagcacc   9120
aggncagggg cctttttggc ggggtgtga gggangatg nctttgctg ggaanncag       9180
gatcaggttc tccaggcgca ctgcagcccg gtaggaccca ctttggaaat gaaaagccag   9240
ttnccgaaag ctgggctgga agcttccgtg ttgggttcaa gagcaagttc acgttgcgct   9300
gtgtagactc ctggctgctc ccaaactctg agggttttct gaggttccct tcataggggc   9360
accggccctg ggccatgcac agtgcgtaag ggtggctgtg ggccgaggga cccagcacgt   9420
gttttgccca caacagccgg agtgactggt tcactcaccg ccttggcgga ggacgccctgt  9480
tctctggacg aatcatttct cttgggtggt gactgccttg tgggtcaagg tgcaggtttt   9540
ctgccacaga aaacctgtta ggaggaatta agcgactaag actgtcaggg aggtggtggt   9600
ggggangag gnaggggtg gtgtccagat taccaggcat aggctaaact gcctgcactc      9660
tccagctggt ctgtctgtgg aggaggggat tgtcaatact gggagagcag aggaggctcg   9720
taggaggtga gaggggtgg aatttgcatg caaatcttca catgaggcct gtgtgaattt    9780
```

```
ctccagcctc ctgagggtcc cctgcgctat tgcactcaac ttcttgatag tttaccccaa    9840
gactcagaag tccttagagg ggcagaatgc ccccaccaca aagcctgcta tccttgggcg    9900
tcctcaggac ccttggtcat gaatgggacc ctttcatgta tggggaccct tggtaatatg    9960
aatgggacgc cttcagctcc ccagggcttc cgaggaggcc gagaagggca aagacacttc   10020
cgaggaggcc gagaagggca aagacatttt ctgggcttgg tgtgtcaaga gctagattgg   10080 agaagggct ggatttggaa ctctttagcc atcagctcac cctctccgtt tgtggctaaa    10140
gtctgaaggt ggaaacttcg gttctcctac agggtctaca ggagttgggg ggcgggggcgc  10200 ccacacagaa cgctggaaag ttcgacagtc cacttccact ggctcggaac tcactttttc   10260
accttaagtt catcagcggt aacgcatagg tctcacttag gcagggcacg gatgatttaa   10320
caatttctac ttctaggtca ggtgcggtgg ctcacacctc taatcccagc actttgggag   10380
gcccaggagg gtggatcgct tgaggtcagg agtttgagac cagcctggcc aacatggtga   10440
aaccccgtct ctactaaaat acgaaaatta gccaggcatg gtggtgagca cctgtaattc   10500
cagctactcg ggaggctgag gcaggagaat cgcttgaacc tgggaggtgg acgttgcagt   10560
gaggtgagat cacaccactg cactccagcc tggatgagag agcaagactc tgtctcaaaa   10620
acaaaataaa acaaaaacaa aacaaaaatc aaaaagaaa acccaatttc cagttctagg    10680
ccaggtgcag tggctcacgc ctgtcatccc agcactttgg gaggcccagg agggtggatc   10740
gcttgaggtc aggagttcga ccagcctg ccaacatgg tgaaacccca tctttactaa      10800
aaatacaaac gttagctggg tgtggtggtg tgcgcctgta atcccagcta ctcgggaagc   10860
tgaggctgga gaattgcttg aatctgggag gtggaggttg cagggaggcg agatagtgcc   10920
actgcagtcc agcctggacc agagagcaag actccgtctc aaaaacaaaa gaaagcaaaa   10980
acaaaaaaca agagaccagc ctggccaaca tggtgaaacc gcgtctttac taaaatacaa   11040
aattagccgg gcatggtggt gggcacctgt agtcccagct actcgggagg ctgaggcagg   11100
agaatggctt gaacctggga ggtggagctt gcagtgagcc gagatagtgc cactgcactc   11160
cagcctgggc gacagagcga gacttgattt cagaaccacc accaccaaa caaaacaaaa    11220 caaaaaatcc aaaaaaaccc caatttccag tactaggtag tcagtgatgc agggctggag   11280 acagagggc ggtaagtgtc tgggcgccca ccatcagtca cctcccagct cccangaggt    11340
gcaaagtgct tggttcagcc tcatgggaag gatgctccct ggggaggctg ggctgggttc   11400
acagggctct tcacatctct ctctgcttct nccccaaggt ttggttncca gaaccggaga   11460
gccaagtgcc gncaaacaag agaatcagat gcataaaggt gggtgtcggg actgggggga   11520
cctgaagctg ggggatcctg ctccaggagg gatgggtcg acaaggtgct ggctacaccc    11580
aggaccacca cactgacacc tgctcccttt ggacacaggg gtcatcttgg gcacagccaa   11640
ccacctagac gcctgccnga gtggcaccct acgtcaacat gggagcctta cggatgcctt   11700
tccaacaggt agctcacttt ttcttcctct gnaagatccc tagggacctg ctgctcccctt   11760 cccctttccc ctatttgctg ccgcatcctg acactcctag tccctcctg cccctgcaga    11820 cttctcagct ggcccttaga aaaaagcct ctttccgag gaggcattta caggcaccctt    11880 ggcacctatg aaatcaggct gggccaggcg gggtggctca cctgtcat ccagcactt     11940 tgggaggcca aggttaggag tttgagacca gcctggacaa catagcaaaa gcctgtctct   12000
actaaaaata caaaaaaaaa ttaacaggga gtggtggtgg gcacctgtaa tcccagctac   12060
ttgggaggct gaggcaggag aatcacttga acccggagg ccgaggttgc ggtgagccga    12120
gatcgtgcca ttgcactcca ggctgggcga cagagtgaga ctctgtctca aaaataaat    12180
```

```
aataaaataa atgtaaaaaa ataaaaatag gtcgggcacg gtggctcacg tctgtaatcc    12240
cagcactttg gaaggccgag gtgggtggat gacagggtca agagattgag accatcctgg    12300
ccaacatggc aaaatgccgt ctctactaaa aatacaaaa attaggcggg cgtggtggcg     12360
ggtgcctgta atcccagcta ctcgggaggc tgaggcagga gaatcggttg aacccgggat    12420
gcggaggttg cagtgagcgg agatcacatc actgcactcc aggctgggca acaagagcga    12480
aactgcgtct tacaataaat aaatagataa ataaataaac aaataaactt tactttagaa    12540
acaaatccct gtccgtgttt gtcttttcac ctgtcctgca gggaaaacaa aacataaaat    12600
gtcaaggcaa atagtagtga tttcattccg ggaaaaagaa agtggatgtt tgccttcacc    12660
ctttctcgtc cttcctctgg tgctcctcan ggcccanggg nagagggtgg aaagtncaga    12720
ggaagaaaga cggggctggg gggggggggtc cgtggggacc caggcaggca tgttcccnat   12780
ttccntgtct tcacnttcaa agnagggggcc cctcgnctct ggaatgaggc ctacggtttc   12840
cttttcccnga agagttnccc ctttgtgagc ttacggcttc ggagtgaacc tcggtgcaac   12900
ctgttattaa aacacacaga ggctaatgcc agcaaaaaca cgccccccgc tcctggtttc    12960
agagggaaga aaaaaattca taagcacggc catgctttc taataaaaat tcattaaata    13020
atcgttataa gggatgaagc cgggagggga gaggagagga acacaatcaa gagactttct    13080
ttgaactttt tctccctgct tcaaatacaa agcaatcttc tgtgggcctg ggcctggggg    13140
gtttccccct ttctctgcag cccattggga ggaagaaaat gcttccctga angttgctgc    13200
aaaattgttt ctgttttct tttctttttc ttttttttt tttttgaga cggagtctcg      13260
ctctgtcacc aggctggagt gcaatggtat gatctcagct cactgcaacc tccacgttcc    13320
tgtttcaagt cattctcctg cctcagcctc ctgagtagct gggactacag gcgcccgcca    13380
ccacgcccgg ctagtgtttg tattttaga aagacaggg tttcccctag ttggccaggc     13440
tggtcttgaa ctcctgtcct caagtgatct gcctgcctcg gcctcccaaa gtgctgtgtt    13500
tctgttttc tttccccgct tcttaggag gccatcggga agaataaaat gctttccttg     13560
aagttgatgc aaaaattgttt ctgtttttct tttctctttt ctttcttttt gagatggagt    13620
ctcgctcttt cacccaggct ggagggcagt ggcgcgacct cggctcactg caacctccgc    13680
ctcccgggtt caagcgattc tcctgcctca gcctccggag tagctgggat tacaggcacc    13740
tgccactatg cctggctaat tttattattt ttagtagaga cggggtttca ccatgttggc    13800
caggctggtc tcaaactcct gacctcaggt gatccgcccg cctcgcctcc caaagtgatg    13860
ggatgancag gncatngagc ncaccgtgcc cggccctcta actctttacc agacataaag    13920
tctccnnttc cccttctaa atgtatatat tgtgttttta aaagttaaca gcagggatcc     13980
cacctcattn ccccgctnct ctccccaaga cctgtcctgc acgttgcaca cagcaggtgt    14040
gccctggaca tatcccaaac ccacgctgaa agaaagaggg tctcactaca cgtatgatat    14100
ctgtgnatcc tttaaacatc tccgtggctt ccaggcaaca cagccataaa taggaatctc    14160
atgtctgaca tgataccggg accatgtatg ggnaaattct gggtgtgaag ttccagctac    14220
cccgcagag gcanccattg catacccctcc agaaactccc ctgccgttnc aagccaaaga   14280
cacaacacaa acagcntccg agagaggggtg tcattgaaaa tcaataccat cataagcagca   14340
cacagcaccg tctttctctt ctgcccgttg atacacaatt atgagcaatt tgctaacact    14400
gacaactcgt ggcaagaaca ggtcgtgttg atacggttgc ctcgtgagga cccatctgtc    14460
ttctgggtc ttgcctggaa cggagatcgg agttcagggt ggctaataga atcattactc    14520
```

```
acctagggac acagaatnat gagggttacc cccagttaag tgcatacagt caaacgacg    14580 gctgctctgg aagtacagt gacgtgaaca gcttttatga aatgcctaga tctggacctt    14640
ccatacctga gccaccgttc caaagcactg ggcgtttttc agatactttc atgagaaatg    14700
ttgtcaacac cgcaagtttg cagtacacag tctgaaagat attcttgtat atgtagatgt    14760
ctgtagatgc cctgaaggtg tgtagacttt agacacccag aaggtgtgta gatgtctgta    14820
gacaccttct atgtgtgtag atgtctgtag acgccctgca ggtgtgtaga tatatctaga    14880
tggtctgcct gtgtatgata caggctaaaa agacatttgt ggtggacact agttgattat    14940
ttaggactat gagatgggaa aggaagnagc aaccagcagt gaaaggcatg tggtgggtgg    15000
ggggttggca ttgcagtggg gtcctcntga ngcaggtgac acccactata gggctgccct    15060
tggnatggac gctttgtnga agctgtttga tttcaccaca ccaagcctgg aggcacggac    15120
attccaggat ggtgaggagt ctgcaaagga ggagattgga ggaggtgcaa tatccctaga    15180
gtacgagaga tgagatagga gagctgtata aatagcacta ccagccggat gcggtggctc    15240
acgcctgtca tcccagcact ttaggaggct gaggcaggcg gatcacctga ggtcaggagt    15300
tccagaacag cctggccaac acaatgaaac cccatcttta ctaaaaatac aagattagct    15360
gggcacggtg tctcacgcct gtcatccctg cactttggga ggtcgaggtg cgcagatcat    15420
gaggtcagtt tggccaacgc ggcgaaaccc cgtctctact aaaaatacaa aaaagtagcc    15480
gggcgtggtg gtgggcacct gtagtcccag ctactaggga ggctgaggca ggagaatcgc    15540
ttgaacccgg atgcggacat tgcagtgagc cgagatc                            15577

<210> SEQ ID NO 9
<211> LENGTH: 753
<212> TYPE: DNA
<213> ORGANISM: Homo sapiens

<400> SEQUENCE: 9
cgtggaagcc tggagttttt gggaacagcg tgtccccgcc gagcctggga gcccgtgggt     60
tctgcaaagc ctgcgggtgt ttgaggactt tgaagaccag tttgtcagtt gggctcaatt    120
cctggggttc agacttagag aaatgaagga gggagagctg gggtcgtctc caggaaacga    180
ttcacttggg gggaaggaat ggagtgttct tgcaggcaca tgtctgttag gaggtgaaac    240
agaatgtgaa atccacgttg gagtaagcgt ccagcgctga atgtagctcg gggtggggtg    300
ggagggccct ggtgtggatc gtggaaggaa gaaagacaga acagggtgct agtatttacc    360
ccgttccctg tagacaccct ggatttgtca gctttgcaag cttcttggtt gcagcggcct    420
tgcctgtgcc cctttgagac tgtttccaga ctaaacttcc aaatgtcagc cccttaccct    480
tgacagcaag ggacatctca ttagggcatc gcgtgcttct catctgtgct cagcaggccc    540
gagataggaa cagaggggcg ttggagatgc cacttccacc agccctgggt tgaaggggag    600
cgagggagac acctttact aaaccctg agcttggtca gagaggctga atgtctaaaa    660
tgaggaagaa aaggtttttc acctggaaac gcttgagggc tgagtcttct gcccttctga    720
ctcccccagc aaatacagac aggtcaccaa cta                                 753

<210> SEQ ID NO 10
<211> LENGTH: 1895
<212> TYPE: DNA
<213> ORGANISM: Homo sapiens
<220> FEATURE:
<221> NAME/KEY: CDS
<222> LOCATION: (91)..(966)
```

<400> SEQUENCE: 10

```
gtgatccacc cgccgcacgg gccgtcctct ccgcgcgggg agacgcgcgc atccaccagc     60
cccggctgct cgccagcccc ggccccagcc atg gaa gag ctc acg gct ttt gta    114
                                 Met Glu Glu Leu Thr Ala Phe Val
                                  1               5 tcc aag tct ttt gac cag aaa agc aag gac ggt aac ggc gga ggc gga    162
Ser Lys Ser Phe Asp Gln Lys Ser Lys Asp Gly Asn Gly Gly Gly Gly
         10                  15                  20 ggc ggc gga ggt aag aag gat tcc att acg tac cgg gaa gtt ttg gag    210
Gly Gly Gly Gly Lys Lys Asp Ser Ile Thr Tyr Arg Glu Val Leu Glu
 25                  30                  35                  40 agc gga ctg gcg cgc tcc cgg gag ctg ggg acg tcg gat tcc agc ctc    258
Ser Gly Leu Ala Arg Ser Arg Glu Leu Gly Thr Ser Asp Ser Ser Leu
                 45                  50                  55 cag gac atc acg gag ggc ggc ggc cac tgc ccg gtg cat ttg ttc aag    306
Gln Asp Ile Thr Glu Gly Gly Gly His Cys Pro Val His Leu Phe Lys
             60                  65                  70 gac cac gta gac aat gac aag gag aaa ctg aaa gaa ttc ggc acc gcg    354
Asp His Val Asp Asn Asp Lys Glu Lys Leu Lys Glu Phe Gly Thr Ala
         75                  80                  85 aga gtg gca gaa ggg att tat gaa tgc aaa gag aag cgc gag gac gtg    402
Arg Val Ala Glu Gly Ile Tyr Glu Cys Lys Glu Lys Arg Glu Asp Val
 90                  95                 100 aag tcg gag gac gag gac ggg cag acc aag ctg aaa cag agg cgc agc    450
Lys Ser Glu Asp Glu Asp Gly Gln Thr Lys Leu Lys Gln Arg Arg Ser
105                 110                 115                 120 cgc acc aac ttc acg ctg gag cag ctg aac gag ctc gag cga ctc ttc    498
Arg Thr Asn Phe Thr Leu Glu Gln Leu Asn Glu Leu Glu Arg Leu Phe
                125                 130                 135 gac gag acc cat tac ccc gac gcc ttc atg cgc gag gag ctc agc cag    546
Asp Glu Thr His Tyr Pro Asp Ala Phe Met Arg Glu Glu Leu Ser Gln
            140                 145                 150 cgc ctg ggg ctc tcc gag gcg cgc gtg cag gtt tgg ttc cag aac cgg    594
Arg Leu Gly Leu Ser Glu Ala Arg Val Gln Val Trp Phe Gln Asn Arg
        155                 160                 165 aga gcc aag tgc cgc aaa caa gag aat cag atg cat aaa ggc gtc atc    642
Arg Ala Lys Cys Arg Lys Gln Glu Asn Gln Met His Lys Gly Val Ile
170                 175                 180 ttg ggc aca gcc aac cac cta gac gcc tgc cga gtg gca ccc tac gtc    690
Leu Gly Thr Ala Asn His Leu Asp Ala Cys Arg Val Ala Pro Tyr Val
185                 190                 195                 200 aac atg gga gcc tta cgg atg cct ttc caa cag gtc cag gct cag ctg    738
Asn Met Gly Ala Leu Arg Met Pro Phe Gln Gln Val Gln Ala Gln Leu
                205                 210                 215 cag ctg gaa ggc gtg gcc cac gcg cac ccg cac ctg cac ccg cac ctg    786
Gln Leu Glu Gly Val Ala His Ala His Pro His Leu His Pro His Leu
            220                 225                 230 gcg gcg cac gcg ccc tac ctg atg ttc ccc ccg ccc ttc ggg ctg        834
Ala Ala His Ala Pro Tyr Leu Met Phe Pro Pro Pro Phe Gly Leu
        235                 240                 245 ccc atc gcg tcg ctg gcc gag tcc gcc tcg gcc gcc gcc gtg gtc gcc    882
Pro Ile Ala Ser Leu Ala Glu Ser Ala Ser Ala Ala Ala Val Val Ala
250                 255                 260 gcc gcc gcc aaa agc aac agc aag aat tcc agc atc gcc gac ctg cgg    930
Ala Ala Ala Lys Ser Asn Ser Lys Asn Ser Ser Ile Ala Asp Leu Arg
265                 270                 275                 280 ctc aag gcg cgg aag cac gcg gag gcc ctg ggg ctc tgacccgccg         976
Leu Lys Ala Arg Lys His Ala Glu Ala Leu Gly Leu
                285                 290
```

```
cgcagccccc cgcgcgcccg gactcccggg ctccgcgcac ccgcctgca ccgcgcgtcc    1036
tgcactcaac cccgcctgga gctccttccg cggccaccgt gctccgggca ccccgggagc    1096
tcctgcaaga ggcctgagga gggaggctcc cgggaccgtc cacgcacgac ccagccagac    1156
cctcgcggag atggtgcaga aggcggagcg ggtgagcggc cgtgcgtcca gcccgggcct    1216
ctccaaggct gccgtgcgt cctgggaccc tggagaaggg taaaccccg cctggctgcg    1276
tcttcctctg ctatacccta tgcatgcggt taactacaca cgtttggaag atccttagag    1336
tctattgaaa ctgcaaagat cccggagctg gtctccgatg aaaatgccat ttcttcgttg    1396
ccaacgattt tctttactac catgctcctt ccttcatccc gagaggctgc ggaacgggtg    1456
tggatttgaa tgtggacttc ggaatcccag gaggcagggg ccgggctctc ctccaccgct    1516
cccccggagc ctcccaggca gcaataagga aatagttctc tggctgaggc tgaggacgtg    1576
aaccgcgggc tttggaaagg gaggggaggg agacccgaac ctcccacgtt gggactccca    1636
cgttccgggg acctgaatga ggaccgactt tataactttt ccagtgtttg attcccaaat    1696
tgggtctggt tttgttttgg attggtattt tttttttttt ttttttttgc tgtgttacag    1756
gattcagacg caaaagactt gcataagaga cggacgcgtg gttgcaaggt gtcatactga    1816
tatgcagcat taactttact gacatggagt gaagtgcaat attataaata ttatagatta    1876
aaaaaaaaat agcaaaaaa                                                 1895
```

<210> SEQ ID NO 11
<211> LENGTH: 292
<212> TYPE: PRT
<213> ORGANISM: Homo sapiens

<400> SEQUENCE: 11

```
Met Glu Glu Leu Thr Ala Phe Val Ser Lys Ser Phe Asp Gln Lys Ser
 1               5                  10                  15

Lys Asp Gly Asn Gly Gly Gly Gly Gly Gly Lys Lys Asp Ser
            20                  25                  30

Ile Thr Tyr Arg Glu Val Leu Glu Ser Gly Leu Ala Arg Ser Arg Glu
        35                  40                  45

Leu Gly Thr Ser Asp Ser Ser Leu Gln Asp Ile Thr Glu Gly Gly Gly
    50                  55                  60

His Cys Pro Val His Leu Phe Lys Asp His Val Asp Asn Asp Lys Glu
65                  70                  75                  80

Lys Leu Lys Glu Phe Gly Thr Ala Arg Val Ala Glu Gly Ile Tyr Glu
                85                  90                  95

Cys Lys Glu Lys Arg Glu Asp Val Lys Ser Glu Asp Glu Asp Gly Gln
            100                 105                 110

Thr Lys Leu Lys Gln Arg Arg Ser Arg Thr Asn Phe Thr Leu Glu Gln
        115                 120                 125

Leu Asn Glu Leu Glu Arg Leu Phe Asp Glu Thr His Tyr Pro Asp Ala
    130                 135                 140

Phe Met Arg Glu Glu Leu Ser Gln Arg Leu Gly Leu Ser Glu Ala Arg
145                 150                 155                 160

Val Gln Val Trp Phe Gln Asn Arg Arg Ala Lys Cys Arg Lys Gln Glu
                165                 170                 175

Asn Gln Met His Lys Gly Val Ile Leu Gly Thr Ala Asn His Leu Asp
            180                 185                 190

Ala Cys Arg Val Ala Pro Tyr Val Asn Met Gly Ala Leu Arg Met Pro
        195                 200                 205
```

```
Phe Gln Gln Val Gln Ala Gln Leu Gln Leu Glu Gly Val Ala His Ala
    210                 215                 220

His Pro His Leu His Pro His Leu Ala Ala His Ala Pro Tyr Leu Met
225                 230                 235                 240

Phe Pro Pro Pro Phe Gly Leu Pro Ile Ala Ser Leu Ala Glu Ser
                245                 250                 255

Ala Ser Ala Ala Ala Val Val Ala Ala Ala Lys Ser Asn Ser Lys
            260                 265                 270

Asn Ser Ser Ile Ala Asp Leu Arg Leu Lys Ala Arg Lys His Ala Glu
        275                 280                 285

Ala Leu Gly Leu
    290

<210> SEQ ID NO 12
<211> LENGTH: 1354
<212> TYPE: DNA
<213> ORGANISM: Homo sapiens
<220> FEATURE:
<221> NAME/KEY: CDS
<222> LOCATION: (91)..(765)

<400> SEQUENCE: 12
```

| | |
|---|---|
| gtgatccacc cgccgcacgg gccgtcctct ccgcgcgggg agacgcgcgc atccaccagc | 60 |
| cccggctgct cgccagcccc ggccccagcc atg gaa gag ctc acg gct ttt gta<br>                                                        Met Glu Glu Leu Thr Ala Phe Val<br>                                                         1               5 | 114 |
| tcc aag tct ttt gac cag aaa agc aag gac ggt aac ggc gga ggc gga<br>Ser Lys Ser Phe Asp Gln Lys Ser Lys Asp Gly Asn Gly Gly Gly Gly<br>    10                15                20 | 162 |
| ggc ggc gga ggt aag aag gat tcc att acg tac cgg gaa gtt ttg gag<br>Gly Gly Gly Gly Lys Lys Asp Ser Ile Thr Tyr Arg Glu Val Leu Glu<br>25                30                35                40 | 210 |
| agc gga ctg gcg cgc tcc cgg gag ctg ggg acg tcg gat tcc agc ctc<br>Ser Gly Leu Ala Arg Ser Arg Glu Leu Gly Thr Ser Asp Ser Ser Leu<br>             45                50                55 | 258 |
| cag gac atc acg gag ggc ggc ggc cac tgc ccg gtg cat ttg ttc aag<br>Gln Asp Ile Thr Glu Gly Gly Gly His Cys Pro Val His Leu Phe Lys<br>        60                65                70 | 306 |
| gac cac gta gac aat gac aag gag aaa ctg aaa gaa ttc ggc acc gcg<br>Asp His Val Asp Asn Asp Lys Glu Lys Leu Lys Glu Phe Gly Thr Ala<br>    75                80                85 | 354 |
| aga gtg gca gaa ggg att tat gaa tgc aaa gag aag cgc gag gac gtg<br>Arg Val Ala Glu Gly Ile Tyr Glu Cys Lys Glu Lys Arg Glu Asp Val<br>90                95                100 | 402 |
| aag tcg gag gac gag gac ggg cag acc aag ctg aaa cag agg cgc agc<br>Lys Ser Glu Asp Glu Asp Gly Gln Thr Lys Leu Lys Gln Arg Arg Ser<br>105                110                115                120 | 450 |
| cgc acc aac ttc acg ctg gag cag ctg aac gag ctc gag cga ctc ttc<br>Arg Thr Asn Phe Thr Leu Glu Gln Leu Asn Glu Leu Glu Arg Leu Phe<br>             125                130                135 | 498 |
| gac gag acc cat tac ccc gac gcc ttc atg cgc gag gag ctc agc cag<br>Asp Glu Thr His Tyr Pro Asp Ala Phe Met Arg Glu Glu Leu Ser Gln<br>        140                145                150 | 546 |
| cgc ctg ggg ctc tcc gag gcg cgc gtg cag gtt tgg ttc cag aac cgg<br>Arg Leu Gly Leu Ser Glu Ala Arg Val Gln Val Trp Phe Gln Asn Arg<br>    155                160                165 | 594 |
| aga gcc aag tgc cgc aaa caa gag aat cag atg cat aaa ggc gtc atc<br>Arg Ala Lys Cys Arg Lys Gln Glu Asn Gln Met His Lys Gly Val Ile<br>170                175                180 | 642 |

-continued

```
ttg ggc aca gcc aac cac cta gac gcc tgc cga gtg gca ccc tac gtc      690
Leu Gly Thr Ala Asn His Leu Asp Ala Cys Arg Val Ala Pro Tyr Val
185                 190                 195                 200 aac atg gga gcc tta cgg atg cct ttc caa cag atg gag ttt tgc tct      738
Asn Met Gly Ala Leu Arg Met Pro Phe Gln Gln Met Glu Phe Cys Ser
            205                 210                 215 tgt cgc cca ggc tgg agt ata atg gca tgatctcgac tcactgcaac            785
Cys Arg Pro Gly Trp Ser Ile Met Ala
        220                 225 ctccgcctcc cgagttcaag cgattctcct gcctcagcct cccgagtagc tgggattaca    845
ggtgcccacc accatgtcaa gataatgttt gtattttcag tagagatggg gtttgaccat    905
gttggccagg ctggtctcga actcctgacc tcaggtgatc cacccgcctt agcctcccaa    965
agtgctggga tgacaggcgt gagcccctgc gcccggcctt tgtaacttta tttttaattt   1025 ttttttttt taagaaaga cagagtcttg ctctgtcacc caggctggag cacactggtg     1085
cgatcatagc tcactgcagc ctcaaactcc tgggctcaag caatcctccc acctcagcct   1145
cctgagtagc tgggactaca ggcacccacc accacaccca gctaattttt ttgattttta   1205
ctagagacgg gatcttgctt tgctgctgag gctggtcttg agctcctgag ctccaaagat   1265
cctctcacct ccacctccca aagtgttaga attacaagca tgaaccactg cccgtggtct   1325
ccaaaaaaag gactgttacg tggaaaaaa                                     1354
```

<210> SEQ ID NO 13
<211> LENGTH: 225
<212> TYPE: PRT
<213> ORGANISM: Homo sapiens

<400> SEQUENCE: 13

```
Met Glu Glu Leu Thr Ala Phe Val Ser Lys Ser Phe Asp Gln Lys Ser
1               5                   10                  15

Lys Asp Gly Asn Gly Gly Gly Gly Gly Gly Lys Lys Asp Ser
            20                  25                  30

Ile Thr Tyr Arg Glu Val Leu Glu Ser Gly Leu Ala Arg Ser Arg Glu
        35                  40                  45

Leu Gly Thr Ser Asp Ser Ser Leu Gln Asp Ile Thr Glu Gly Gly Gly
    50                  55                  60

His Cys Pro Val His Leu Phe Lys Asp His Val Asp Asn Asp Lys Glu
65                  70                  75                  80

Lys Leu Lys Glu Phe Gly Thr Ala Arg Val Ala Glu Gly Ile Tyr Glu
                85                  90                  95

Cys Lys Glu Lys Arg Glu Asp Val Lys Ser Glu Asp Glu Asp Gly Gln
            100                 105                 110

Thr Lys Leu Lys Gln Arg Arg Ser Arg Thr Asn Phe Thr Leu Glu Gln
        115                 120                 125

Leu Asn Glu Leu Glu Arg Leu Phe Asp Glu Thr His Tyr Pro Asp Ala
    130                 135                 140

Phe Met Arg Glu Glu Leu Ser Gln Arg Leu Gly Leu Ser Glu Ala Arg
145                 150                 155                 160

Val Gln Val Trp Phe Gln Asn Arg Arg Ala Lys Cys Arg Lys Gln Glu
                165                 170                 175

Asn Gln Met His Lys Gly Val Ile Leu Gly Thr Ala Asn His Leu Asp
            180                 185                 190

Ala Cys Arg Val Ala Pro Tyr Val Asn Met Gly Ala Leu Arg Met Pro
        195                 200                 205
```

Phe Gln Gln Met Glu Phe Cys Ser Cys Arg Pro Gly Trp Ser Ile Met
    210                 215                 220
Ala
225

<210> SEQ ID NO 14
<211> LENGTH: 32367
<212> TYPE: DNA
<213> ORGANISM: Homo sapiens

<400> SEQUENCE: 14

| | | | | | |
|---|---|---|---|---|---|
| tttctctgtc | tccatccctc | tgtctctccc | tttctctctg | tctttccttg | tctctctctt | 60 |
| tctctctctc | tctccatctc | tctctctccc | tgtctctctc | tctccatctc | cccgtctctc | 120 |
| cgtttctctc | tctgcctctc | cctgtctgtc | tctctctttc | tgtgtcttac | acacacccca | 180 |
| acccaccgtc | actcatgtcc | cccactgct | gtgccatctc | acacaagttc | acagctcagc | 240 |
| tgtcatcctg | ggtccccagg | cccgccggg | gaggaagatg | cgccgtgggg | ttacgggagg | 300 |
| aagggggactc | cgggcctcct | ggtgccccac | tttatttgca | gaaggtcctt | ggcaggaacc | 360 |
| gtgacgcgtt | tggtttccag | gacttggaaa | acgaatttca | ggtcgcgatg | gcgagcaccg | 420 |
| gcttccctg | aagcacattc | aatagcgaga | ggcgggaggg | agcgagcagg | agcatcccac | 480 |
| catgaaaacc | aaaaacacaa | gtattttttt | cacccggtaa | ataccccaga | cgccagggtg | 540 |
| acagcgcggc | gctaagggag | gaggcctcgc | gccgggtcc | gccgggatct | ggcgcgggcg | 600 |
| gaaagaatat | agatctttac | gaaccggatc | tcccggggac | ctgggcttct | ttctgcgggc | 660 |
| gctggagacc | cggaggcgg | ccccggggat | cctcggcctc | cgccgccgcc | gcctcccaag | 720 |
| cgcccgcgtc | ccggtttggg | gacacccggc | cccttcttct | cactttcggg | gattctccag | 780 |
| ccgcgttcca | tctcaccaac | tctccatcca | agggcgcgcc | gccaccaact | tggagctcat | 840 |
| cttctcccaa | gatcgtgcgt | ccccggggcg | cccgggtccc | cccctcgcc | atctcaaccc | 900 |
| cggcgcgacc | cgggcgcttc | ctggaaagat | ccaggcgccg | ggctctgcgc | tcctcccggg | 960 |
| agcgagggcg | gccggacgac | tgggacccctc | ctctctccag | ccgtgaactc | cttgtctctc | 1020 |
| tgtctctctc | tgcaggaaaa | ctggagtttg | cttttcctcc | ggccacggag | agaacgcggg | 1080 |
| taacctgtgt | gggggggctcg | ggcgcctgcg | cccccctcct | gcgcgcgcgc | tctcccttcc | 1140 |
| aaaaatggga | tctttccccc | ttcgcaccaa | ggtgtacgga | cgccaaacag | tgatgaaatg | 1200 |
| agaagaaagc | caattgccgg | cctgggggt | ggggagaca | cagcgtctct | gcgtgcgtcc | 1260 |
| gccgcggagc | ccggagacca | gtaattgcac | cagacaggca | gcgcatgggg | ggctgggcga | 1320 |
| ggtcgccgcg | tataaatagt | gagatttcca | atggaaaggc | gtaaataaca | gcgctggtga | 1380 |
| tccacccgcg | cgcacgggcc | gtcctctccg | cgcggggaga | cgcgcgcatc | caccagcccc | 1440 |
| ggctgctcgc | cagccccggc | cccagccatg | aagagctca | cggcttttgt | atccaagtct | 1500 |
| tttgaccaga | aaagcaagga | cggtaacggc | ggaggcggag | gcggcggagg | taagaaggat | 1560 |
| tccattacgt | accgggaagt | tttggagagc | ggactggcgc | gctcccggga | gctggggacg | 1620 |
| tcggattcca | gcctccagga | catcacggag | ggcggcggcc | actgcccggt | gcatttgttc | 1680 |
| aaggaccacg | tagacaatga | caaggagaaa | ctgaaagaat | tcggcaccgc | gagagtggca | 1740 |
| gaaggtaagt | tcctttgcgc | gccggctcca | ggggggcct | cctgggttc | ggcgcctcct | 1800 |
| cgccacggag | tcggccccgc | gcgccccctcg | ctgtgcacat | ttgcagctcc | cgtctcgcca | 1860 |
| gggtaaggcc | cgggccgtca | ggctttgcct | aagaaaggaa | ggaaggcagg | agtggacccg | 1920 |

-continued

```
accggagacg cgggtggtgg gtagcgggt gcgggggggac ccagggaggg tcgcagcggg    1980
ggccgcgcgc gtgggcaccg acacgggaag gtcccgggct ggggtggatc cggtggctg     2040 tgcctgaagc cgtagggcct gagatgtctt tttcattttc ttttctttc ctttcctttt    2100 tttgtttgtt tgtttgtttg tttgagacag agtctcgctc tgtccccag gctggagtgc    2160 agtggtgcga tctcggctca ctgcaacctc cgcctcctgg gttcaagcga ttctcctgcc    2220
tcagcctccc cagtagctgg gattacaggc atgcaccacc acgcctggct aattttttgtg   2280 cttttagtaa agacgggat tcaccatgtt ggccaggctg gtctcgaact cctgacctca    2340
ggtgatccac ccgcctcggc ctcccaaagt gctgggatga caggcgtgag gcaccgcgcc    2400
cggcctgggt cctgacggct taggatgtgt gtttctgtct ctgcctgtct gccttgtatt    2460
tacggtcacc cagacgcaca gaggagccgt ctccacgcgc cttcccagcg ctcagcgcct    2520
gccgggcccc cggagatcac gggaagactc gaggctgcgt ggtaggagac gggaaggccc    2580
cgggtcagct cggttctgtt tcctttaagg aacccttcat tattatttca ttgttttcct    2640
ttgaacgtcg aggcttgatc ttggcgaaag ctgttgggtc cataaaaacc actcccgtga    2700
gcggaggtgg ccgggatctg gatggggcgc gaggggcccc ggggaagctg gcggcttcgc    2760
gggcgcgtcc taagtcaagg ttgtcagagc gcagccggtt gtgcgcggcc cggggagct    2820 cccctctggc ccttcctcct gagacctcag tggtgggtcg tcccgtggtg gaaatcgggg    2880
agtaagaggc tcagagagag gggctggccc cggggatctc tgtgcacaca cgacaactgg    2940
gcggcataca tcttaagaat aaaatgggct ggctgtgtcg gggcacagct ggagacggct    3000
atggacgcct gttatgtttt cattacaaag acgcagagaa tctagcctcg gcttttgctg    3060
attcgcagag ttgaggtgcg agggtgaatg ccccaaaggt aattcttcct aagactctgg    3120
ggctacctgc tctccggggc cctgcatttg gggtgtggag tggcccccggg aaatagccct    3180 tgtattcgta ggaggcacca ggcagcttcc caaggccctg actttgtcga agcagaaagc    3240
tgtggctacg gtttacaaag cagtccccgg tttctgaccg tctaagaggc aggagcccag    3300
cctgcctttg acagtgagag gagttcctcc ctacacactg ctgcgggcac ccggcactgt    3360
aattcataca cagagagttg gccttcctgg acgcaaggct gggagccgct tgagggcctg    3420
cgtgtaattt aagagggttc gcagcgcccg gcggccgctt ctgtgggtt gcttttggt     3480 tgtccttcgc agacaccgtt ttgctcctct gaactctctc ttctcccct ggccgtggac    3540 ccggagagc aaagtgtcct ccagaccttt tgaaagtgag aggaaaataa agaccaggcc    3600
aaagacccag ggccacagga gaggagacag agagtccccg ttacattttc cccttggctg    3660
ggtgcagaaa gaccccgggg ccaggactgc cacccaggct actatttatt catcagatcc    3720
aagttaaatc gaggttggag ggcaggggag agtctgaggt taccgtggaa gcctggagtt    3780
tttgggaaca gcgtgtcccc gccgagcctg ggagcccgtg ggttctgcaa agcctgcggg    3840
tgtttgagga ctttgaagac cagtttgtca gttgggctca attcctgggg ttcagactta    3900
gagaaatgaa ggagggagag ctgggtcgt ctccaggaaa cgattcactt gggggaagg     3960 aatggagtgt tcttgcaggc acatgtctgt taggaggtgaa aacagaatgt gaaatccacg   4020
ttggagtaag cgtccagcgc tgaatgtagc tcgggtggg gtgggagggc cctggtgtgg    4080
atcgtggaag gaagaaagac agaacagggt gctagtattt accccgttcc ctgtagacac    4140
cctggatttg tcagctttgc aagcttcttg gttgcagcgg ccttgcctgt gccccttga    4200 gactgttccc agactaaact tccaaatgtc agccccttac ccttgacagc aagggacatc    4260
tcattagggc atcgcgtgct tctcatctgt gctcagcagg cccgagatag gaacagaggg   4320
```

```
gcgttggaga tgccacttcc accagccctg ggttgaaggg gagcgaggga gacaccttt    4380 acttaaaccc ctgagcttgg tcagagaggc tgaatgtcta aaatgaggaa gaaaaggttt    4440
ttcacctgga aacgcttgag ggctgagtct tctgcccttc tgactccccc agcaaataca    4500
gacaggtcac caactactgg agatgagaaa gtgccatttt tggcacactc tggtggggta    4560
ggtgcccgac cgcgtgtgaa aaagtgggaa ggagagattt ctgcgcacgc ggttcagccc    4620 ccagcgcgg tggcgcattc aggtactcag acgcggttct gctgttctgc tgagaaacag    4680
gcttcgggta ggggctccta gctccgccag atcgcggagg gaccccagc cctcctgcgc     4740 tgcagcggtg gggatagcgt ctctccgtag gcctagaatc tgcaacccgc cccgggtcct    4800
ccccgtgtcc ttcccgggcg tcccgccggg gatcccacag ttggcagctc ttcctcaaat    4860 tctttcccctt aaaaatagga tttgacaccc cactctcctt aaaaaaaaaa aataagaaaa    4920
aaaggttagg ttatgtcaac agaggtgaag tggataattg aggaaacgat tctgagatga    4980
ggccaagaaa acaacgctcg tgcaaagccc aggttttgg gaaagcagcg agtatcctcc     5040
tcggcttttg cgttatggac cccacgcagt ttttgcgtca agcgcattg gttttcgagg     5100 gccccctttc caccgcggga tgcacgaagg ggttcgccac gttgcgcaaa acctccccgg    5160
cctcagccct gtgccctccg ctccccacgc agggatttat gaatgcaaag agaagcgcga    5220
ggacgtgaag tcggaggacg aggacgggca gaccaagctg aaacagaggc gcagccgcac    5280
caacttcacg ctggagcagc tgaacgagct cgagcgactc ttcgacgaga cccattaccc    5340
cgacgccttc atgcgcgagg agctcagcca gcgcctgggg ctctccgagg cgcgcgtgca    5400
ggtaggaacc cggggcggg ggcggggggc ccggagccat cgcctggtcc tcgggagcgc     5460
acagcacgcg tacagccacc tgcgcccggg ccgccgccgt ccccttcccg gagcgcgggg    5520
aggttgggtg agggacgggc tggggttcct ggacttttgg agacgcctga ggcctgtagg    5580
atgggttcat tgcgtttgtt tttcaccaac agcaaacaaa tatatataca tatatattat    5640
acaaataaca aataaatata tatgttatac agatgggtat attgtatata ttatagatat    5700
ttgttcgtcc ttggtgcaaa gacacccggt gaacccatat attggctcct gactgccttc    5760
ggttcccctg ggattggtta tagggcaac acatgcaaac aaaactttcc ctggattata      5820
cttaggagac gaagctacag atgcgtttga tccagagtgt tttacaagat ttttcattta    5880
aaaaaaaatg tgtcttttgg cccctgattc ccctccgtct tcccgtgtgg ctgcattgaa     5940
aaggtttcct taggatgaaa ggagaggggt gtcctctgtc cctaggtgga gagaaacagg    6000
gtcttctctt tcctccgttt tttcacctac cgtttctatc tccctcctcc cctctccagc    6060
cctgtcctct gctacaaacc ccccctcct ccctccggct gtggggagcg caggagcacg     6120
ttgggcatct ggatgagcgg agactattag cggggcacgg gggctccccg aggagcgcgc    6180
gaattcacgc tgccccatga ccaggcac cggggggcgg aggggccttg ggtgtccgca      6240
gagggacggg cgggcagagc cttcctccgc attctaaaca ttcacttaaa ggtatgagtt    6300
tatttcaggt gtgctgctgg gagagcctcc aaatggcttc ttccagcccc tgcctgacag    6360
ttcagctccc ctggaaggtc aactcctcta gtcctttctc ctggttctgg gcaggacaga    6420
agtgggggga gggagagaga gagagagaga gagagagacg tcaggatcc ccggaccctg     6480 gggaacccgt caaaaataaa tgaaattaag attgccgacc agagagagaa ccgtgacaaa    6540
gcaaacggcg ttcaaagcaa agagacgaac tgaaagcccg ttcccgtagg actggttatg    6600
aggtcaacac attcaaacac agcttgctct ggattttgct gagcagagga agatacagat    6660
```

-continued

```
gcatttgatc caaagtgtgt tacatctttc attatatgtg tgtctatata tataaacata    6720
tataaatata taaacataca taaatgtatg taaatatata taatctatat acatatataa    6780
atatataaac acatatataa tatataaatc tataaacata tataatatat aaacataaat    6840
atataaacat atataatata taaatatatt aacatatata aaatatgtat aaatatatat    6900
aaacatataa acatatataa atatataaac atataaatat ataaacatat ataaatatat    6960
acaaacatat tgtatatata taaatatata taaaacata tatatacata taaaaatata    7020
tataaacata tatacatata aagaaatata taaaacata tatacatata aatatacata    7080
tataaacata tatatacata aaatatatat aaacatatat acatataaaa atatatatat    7140
attaacatat atatacatat aaaaatatat atattaacat atatatacat ataaaaatat    7200
atatatattt ttggcccctg attcccttcg gttcctgtgg gatgggtgat tgagtcaaca    7260
cattcaaaca caacttttcc atcgatgttg cttaggagat gaggatacag atgcgtttga    7320
tggagagggt tttacaagct ctttcattta aatatatata tatatatata tatattttt    7380
ggctcctgat tctcttccgt cttcccatgt ggctgcattt taaaaggctt ccctaagatc    7440
gttacgatta aatcaaccct ccccaggcat ctttaccgag ggctgtggtc cccaaagcga    7500
tacagcccag gagggagaga ggctttggtg acttggagga aggactgtgt ccctccttag    7560
ggcgtctgtg gcctcagtga gggaaggaag ctgcatcaga caggggtttc ctcgctgtcc    7620
accctctgg cagaagatgg attgggctgc cccgtataaa ttaatgaaaa gattaaagtt    7680
tcgctaaagg ggacatcgag tttatgtgtc atctcctggt gtctgtgtgc ctgggatctg    7740
caatatatcc cagcccttga tgtactgttt ctataaaat aaattacttg taatttaatt    7800
ccacactatt tctttccgta gtctattacc gacgagagca cgttagttca gctgcggaaa    7860
attggttgtg gggtgtgtgc ggaccccgag aacgccctaa aataaagaca aatcggggac    7920
aagctggggg ttatcgattg caggggtcgc atgaaaattt aacgacggta aataataata    7980
aaaacaaaca tgggaatgca ataaaagaca taattctcca tcgccgcggg gggaaaggat    8040
cctatagtaa aggcgagtgc gctttgaggg gtcataaaaa tcaattagtt ccaacaccca    8100
cgtcccgcgt tgaggggacg gggacgagca gggacagaaa aagaaaccat atttgaatcc    8160
catctctctg tgaattcttg ggtcacatgc gtctcagtac agcccgtccc gtgctgtgac    8220
cggatagagt ttcaatttac tgtggaaatt tgctgtaaat aaattgagca tccgatagaa    8280
gctgttgctg attaaccttt tatttttagc gtggccctgc aaagtcgtat cacccagctg    8340
tcaggcttct aatcgaaagt tatgagacca cggtgagggg caggcggtaa tttaattaca    8400
acaaatatct ttgggtttat ggcgcagagc taaattaaat gtcattattc actgtctgta    8460
atggaaatca aaaggaaatc gcattacggc atttgggaaa gaaagcgggg agtgctcttt    8520
aatgaagaaa taactgtctt aagcagtgtc acacacttca cttaccatat tcgggcctaa    8580
ttggaatgga tcgtgaatca ctccaagact gatttattag cgcttcacgc agcggctaat    8640
tcatcacttg tattcttcat cattttttt tttcctctcg ccgtgttgaa gggagagtga    8700
atgaggcttt ccacgtttca ggaggatttt cttttttgaa aaatgccctt ccagaggctt    8760
ttgggtggct ggcttgcttt ctggccctg gaggagacag gcggagagtc caggtgggca    8820
tggagaggca cagtggcagg tcacctggat ggtcagtgga ggtggaggtc tgaaggcgcc    8880
agctttggaa attattggtg aatttcgatg tcagcaccag gcagggcct ttttggcggg    8940
ggtgtgaggg aggatgactt tgctgggaaa caggatcagg ttctccaggc gcactgcagc    9000
ccggtaggac ccactttgga aatgaaaagc cagttccgaa agctgggctg gaagcttccg    9060
```

```
tgttgggttc aagagcaagt tcacgttgcg ctgtgtagac tcctggctgc tcccaaactc    9120
tgagggtttt ctgaggttcc cttcataggg gcaccggccc tgggccatgc acagtgcgta    9180
agggtggctg tgggccgagg gacccagcac gtgttttgcc cacaacagcc ggagtgactg    9240
gttcactcac cgccttggcg gaggacgcct gttctctgga cgaatcattt ctcttgggtg    9300
gtgactgcct tgtgggtcaa ggtgcaggtt ttctgccaca gaaaacctgt taggaggaat    9360
taagcgacta agactgtcag ggaggtggtg gtgggggaga ggaggggggtg gtgtccagat    9420 taccaggcat aggctaaact gcctgcactc tccagctggt ctgtctgtgg aggaggggat    9480
tgtcaatact gggagagcag aggaggctcg taggaggtga gaggggggtgg aatttgcatg    9540 caaatcttca catgaggcct gtgtgaattt ctccagcctc ctgagggtcc cctgcgctat    9600
tgcactcaac ttcttgatag tttaccccaa gactcagaag tccttagagg ggcagaatgc    9660
ccccaccaca aagcctgcta tccttgggcg tcctcaggac ccttggtcat gaatgggacc    9720 cttttcatgta tggggaccct tggtaatatg aatgggacgc cttcagctcc ccagggcttc    9780
cgaggaggcc gagaagggca aagacacttc cgaggaggcc gagaagggca aagacatttt    9840
ctgggcttgg tgtgtcaaga gctagattgg agaagggct ggatttggaa ctctttagcc    9900
atcagctcac cctctccgtt tgtggctaaa gtctgaaggt ggaaacttcg gttctcctac    9960
agggtctaca ggagttgggg ggcggggcgc ccacacagaa cgctggaaag ttcgacagtc    10020
cacttccact ggctcggaac tcactttttc accttaagtt catcagcggt aacgcatagg    10080
tctcacttag gcagggcacg gatgatttaa caatttctac ttctaggtca ggtgcggtgg    10140
ctcacacctc taatcccagc actttgggag gcccaggagg gtggatcgct tgaggtcagg    10200
agtttgagac cagcctggcc aacatggtga accccgtctc tactaaaat acgaaaatta    10260 gccaggcatg gtggtgagca cctgtaattc cagctactcg ggaggctgag gcaggagaat    10320
cgcttgaacc tgggaggtgg acgttgcagt gaggtgagat cacaccactg cactccagcc    10380
tggatgagag agcaagactc tgtctcaaaa acaaaataaa acaaaaacaa aacaaaaatc    10440 aaaaagaaa acccaatttc cagttctagg ccaggtgcag tggctcacgc ctgtcatccc    10500
agcactttgg gaggcccagg agggtggatc gcttgaggtc aggagttcga gaccagcctg    10560
gccaacatgg tgaaacccca tctctactaa aaatacaaac gttagctggg tgtggtggtg    10620
tgcgcctgta atcccagcta ctcgggaagc tgaggctgga gaattgcttg aatctgggag    10680
gtggaggttg cagggaggcg agatagtgcc actgcagtcc agcctggacc agagagcaag    10740
actccgtctc aaaaacaaaa gaaagcaaaa acaaaaaaca agagaccagc ctggccaaca    10800
tggtgaaacc gcgtctctac taaaatacaa aattagccgg gcatggtggt gggcaccttgt    10860 agtcccagct actcgggagg ctgaggcagg agaatggctt gaacctggga ggtggagctt    10920
gcagtgagcc gagatagtgc cactgcactc cagcctgggc gacagagcga gcttgatttt    10980
cagaaccacc accaccacaa caaaacaaaa caaaaaatcc aaaaaaaccc caatttccag    11040
tactaggtag tcagtgatgc agggctggag acagagggc ggtaagtgtc tgggcgccca    11100
ccatcagtca cctcccagct cccagaggtg caaagtgctt ggttcagcct catgggaagg    11160
atgctccctg gggaggctgg gctgggttca cagggctctt cacatctctc tctgcttctc    11220
cccaaggttt ggttccagaa ccggagagcc aagtgccgca acaagagaa tcagatgcat    11280 aaaggtgggt gtcggactg gggggaccctg aagctggggg atcctgctcc aggagggatg    11340
gggtcgacga ggtgctggct acacccagga ccaccacact gacacctgct ccctttggac    11400
```

```
acaggcgtca tcttgggcac agccaaccac ctagacgcct gccgagtggc accctacgtc    11460
aacatgggag ccttacggat gccttttccaa caggtagctc acttttttctt cctctgaaga   11520 tccctaggga cctgctgctc ccttcccctt tcccctattt gctgccgcat cctgacactc    11580
ctagtccctc cctgcccctg cagacttctc agctggccct tagaaaaaaa gcctcttttc    11640
cgaggaggca tttacaggca ccttggcacc tatgaaatca ggctgggcca ggcggggtgg    11700
ctcacacctg tcatcccagc actttgggag gctgaggagg gtgcatcacc tgagatcagg    11760
agttcaagac cagcctggcc aacttaacga aaccccgtct attaaaaata caaaatgggt    11820
gtggtggctc acgcctgtca tcccagcact ttgggaggcc gaggcaggtg gatcacctga    11880
ggtcaggaat tcgagaccag cctgaccaac atgctgaaac cccgtctcta ctgaaaacac    11940
aaagcttagc cgggcgtggt ggtgcacacc tgtgatccca ggtacttggg agggagaatc    12000
acttgaacct gggaggtgga ggttgccgtg agccaatatc gcgccactgc actccactct    12060
gggtgacaga gtgagactcc aagactccat ctcaaaaaaa aaaaaaaaaa tcaggctgta    12120
aaaatccact tttgggaagg tgaacacaca caagcccaaa cagaaatctg acaaaaacca    12180 gagggtgaa aagtccacac agtcaggcac ccccacctgg cttgctgcct ggttaagaag     12240
ggcgcagatg cctgtgcctg ataccagag atgggacaga cacccattcc cttttcatca     12300
ccacccccga gtcccgagg gcctgggggcg tctgcctggc ccctggcccc tggcttgggc    12360
tctgcacctc tgaactggag acaccctact cagctcccca cttactttgg agtgagcagc    12420
gcttgggtgc ccagcgtgga tttgggcctt ccagggagtc ggggttcggt cgcggagccc    12480
aagcttccca agggcgcccc cgccctgccc tggcttagtg gtgggatgg gatgggggga    12540 aacgggagc tgcgtggaag gaggtgaagg gtcacaggag gagagagcgc agcgcccacg    12600
tgcgccctgc ctgaacgcgc agcgcagcgc ccggctgcgg tgcccttgc ccttcggtc     12660 cctaattttgg ggatcgggag tgcatgcgcg ggcggaacgg gcttgggggg ggggctctgg  12720
cagggcggac gcgtggcctc ccttcttcac cgttttattc caaggggaca ggctggggat    12780 tgtattttggg cgcgtgtttg gctgagggtg cagggacttg gggggtggcg gtggggagcg   12840
cggaaggtat aaacgtataa atcataagta aacaactcag aaatggaccc cgagcgctgg    12900
tcgccgctag ctctccagct ctccctggcc caggcccgaa ggagaggggt ccgcatccct    12960
ccgcggttct cctctcctgg gtacctggcc ttgaggtggg ggaacgagcc tacttcttgt    13020
accgtctttt gccgacggcg ggacccagtg aaattaggcc gttggagccc gcaggcctgc    13080
ctggctttgc gcaccggagt cttggggacc tggtgtcccc gggaaaaact tggggacctg    13140
gtatccccgg gagaggcttg gggacctggt gtcccgggag aggcttgggt acctggtttc    13200 tctgaagag gcttggacac ctggtgtcct ggagggcct ttgggacctg gtgtcctggg     13260
agaggcttgg agatctgttg tcctgggaga ggcttgggga cctggtgtcc ctggagaggc    13320
ttggggacct ggtgaccttg gagaggcttg gagacctggt gttctgggag aggcttgggg   13380
acctggtgtt ctgggagagg cttgggggacc tggtgtctct ggaagaggct tggacacctg   13440
gtgacccggg agggccttgg ggatctggtg tcccgggaga gccttgggga cctggtgtcc    13500
tgggagaggc ttggggacct ggtgaccttg gagaggcttg gggacctggt gtcctgagag    13560
agccttgggg atctggtgtc ccaggagagg cttgggggacc tggtgtctct ggaagaggct  13620
tggacacctg gtgtcctggg gagaggcttg gggacctggt gtcctgggag aggcttgggg    13680
acctggtgtc ctgggagagg cttggagatc tggtgagccg ggagaggctt ggggacctgg   13740
tgtcccggga gaggcttggg gacttggtgt cccgggagag gcttgaacac ctggtgtccc    13800
```

```
aggagaggct tggggacctg gtgaccttgg agaggcctgg ggacctggtg acccgggaga   13860
gccttgggga cctggtgtcc tggggagagc cttggggacc tggtgacctt ggagaggctt   13920
ggggacctgg tgtctcggga gtgccttggg gacctagtga cccgggagag cttggggac   13980 ctggtgtccc gggagaggct tggggacctg gtgtcctggg agagccttgg ggatctggtg   14040
tcctggggag aggctggggg acctggtgtc tcgggagaga gccttgggga cctggtgacc   14100
cgggagaggc ttggacacct ggtgtcccgg gagaggcttg ggacctggt gacccgggag    14160 agccttgggg acctggtgtc ctggggagag gctgggggac ctggtgtctc gggagagagc   14220
cttggggacc tggtgacccg ggagaggctt ggacacctgg tgtcccggga gaggcttggg   14280
agcctggtgt cccgggagag ccttggggac caggtgacct tggagaggct tggggacctg   14340
gtgatcttgg agaggcttgg ggacctggtg tctcgggaga ggttacgggg gctggttggg   14400
ggagagaacg ttgtgagcca aagtccctga atccctgcga aaagagcgca tcggagctc    14460 cccctgaggg cgttccattt gtggacccc ctcccatgcg ctttgcaggg agctgttcgg    14520
attcccctgg cccggctccc gcggatgcat ccagtggcag cgccaattct gggccagggg   14580
gaaggaggaa aggcgggtgt ggggtggtct ccacggctgg agaaggggcg acgctcccta   14640
ggggagaaga ggcacgttgg gggtttccgg gggcgcgggg cggagcaggc cccccagtcc   14700
ccatcctgcg ccctcacccc gccgggtccg ctcccgcagg tccaggctca gctgcagctg   14760
gaaggcgtgg cccacgcgca cccgcacctg cacccgcacc tggcggcgca cgcgccctac   14820
ctgatgttcc ccccgccgcc cttcgggctg cccatcgcgt cgctggccga gtccgcctcg   14880
gccgccgccg tggtcgccgc cgccgccaaa agcaacagca agaattccag catcgccgac   14940
ctgcggctca aggcgcggaa gcacgcggag gccctgggcc tctgacccgc cgcgcagccc   15000
cccgcgcgcc cggactcccg ggctccgcgc accccgcctg caccgcgcgt cctgcactca   15060
accccgcctg gagctccttc cgcggccacc gtgctccggg caccccggga gctcctgcaa   15120
gaggcctgag gagggaggct cccgggaccg tccacgcacg acccagccag accctcgcgg   15180
agatggtgca gaaggcggag cgggtgagcg gccgtgcgtc cagcccgggc ctctccaagg   15240
ctgcccgtgc gtcctgggac cctggagaag ggtaaacccc cgcctggctg cgtcttcctc   15300
tgctataccc tatgcatgcg gttaactaca cacgtttgga agatccttag agtctattga   15360
aactgcaaag atcccggagc tggtctccga tgaaaatgcc atttcttcgt tgccaacgat   15420
tttctttact accatgctcc ttccttcatc ccgagaggct gcggaacggg tgtggatttg   15480
aatgtggact tcggaatccc aggaggcagg ggccgggctc tcctccaccg ctcccccgga   15540
gcctcccagg cagcaataag gaaatagttc tctggctgag gctgaggacg tgaaccgcgg   15600
gctttggaaa gggaggggag ggagacccga acctcccacg ttgggactcc cacgttccgg   15660
ggacctgaat gaggaccgac tttataactt ttccagtgtt tgattcccaa attgggtctg   15720
gttttgtttt ggattggtat tttttttttt tttttttttt gctgtgttac aggattcaga   15780
cgcaaaagac ttgcataaga gacgacgcg tggttcaag gtgtcatact gatatgcagc     15840 attaactta ctgacatgga gtgaagtgca atattataaa tattatagat taaaaaaaaa    15900
atagccgtgc actcttgacc ccgtcaacgt ccaacgtgga aaaggcgtta cctcttctcc   15960
cagcgctggc cgcctggcca ctgagggccc tttgcaaaaa tcacgggtgt agagatggcc   16020
ctgggcgcgc tgggagtgtg gttgtgtttc tgaaggggat aaaagagggc acggtggtgc   16080
caagatatca gtttggtacc tgagctgttt ctggttggga agcgtaaaag ccaggagag    16140
```

-continued

```
atccagagag ttttcaagtt tttgcagatg taggtggttc cagcttttct ttctcccta    16200 ctccatcttc tgcgttcccc cagttctttt atttctttgt tttttatttt tgagacagag    16260
acttgctttg tcgcccaggc tggagtgcag tggcgcaatg tcagctcact gccacctcca    16320
cctcccgggt tcaagcgatg ctcctgcctc agcctcccga gtagctggga ctacaggcac    16380
ctgccaccac ccccggctaa ttttttgtat ttatagtaga cacggggttt caccgtgttg    16440
gccaggctcg tctcgaactc ctgacctcag gtgatctgcc cgcctcggcc tccaacgtg    16500 cccccagttt tataaacagc agatagcaac ttgtcgtcac agctggcatg ggctggacag    16560
ttgcttgaaa tgacctaacc aaaaacattc aagggttctg cccccagatt tcgggagatc    16620
cacgttccat gttctgattg gttttctggg aacacagcaa ggggtttggt gacctccgag    16680
aagatccatc tgcatgattg gcattagtta ccacagcctg cccagagaga aactatcttc    16740
tcccaacatt tactaacatc cactggtcaa ctctcttatt tccataacac atttgcatct    16800
ttctggattc aagcttggtg gttttctttc ctaacttctg atttagatac ttctccctga    16860
ggtggggata aagaaaaaa aaaaacaac ttctttttt cttccgcata acactttcta    16920
tcttgtcact gagctgaact gtagatccat ttggacccgt ctcatttgta tcttctgata    16980
ttctttatac aaaccaaaag tcccttcaa cattttttat gtcaaaatgt tacaaccgct    17040
gtaaaatgac ggagagagag agaaagaatc ccagacatta acggtattag agagtttgcc    17100
tcattcatcc atttttctta aaagctggaa attaaaaaaa aaaagagag agagaggctt    17160 taatagttaa gctgaaattt ttatcgaaaa gaagaattgc attttgaatc tttgggaagt    17220
aggttcattc atcagagtat gtaacccttt ggaaaagtgg ttggtaagat atgtacagcc    17280
ctagattttt tttttttaa ccaaaaaggc tgagtaattt tgaaaaatcg aaacataaca    17340
gtgtgtcatc atttcctccc aagaaaaagc tcactccacg tgagtagaaa gacatctacc    17400
tggtccctgt agaatctgaa cgtttctctt tagagacgga atttcaatct tgttgcccag    17460
gctggagtgc agtggcacaa tctcggctca ccgcaacctc cgcctccgg gttcaagcca    17520 ttctcctgcc tcagtctccc gagtagctgg gattacaggc acctgccacc aggcctgggt    17580
aactttctgg tatttttagt agagacaggg tttcagcctc ccgagtagct gggattacag    17640
gcacctgcca ccaggcctgg gtaactttct ggtattttta gtagagacag ggtttcagcc    17700
tcccgagtag ctgggattac aggcacctgc caccaggcct gggtaacttt ctggtagttt    17760
tagtagagac agggtttcgg cctcccgagt agctgggatt acaggcacct gccaccaggc    17820
ctgggtaact ttctggtatt tttagtagag acagggtttc ggcctcccga gtagctggga    17880
ttacaggcac ctgccaccag gcctgggtaa cttctggta ttttagtac agacagggtt    17940 tcggcctcct gagtagctgg gattacaggc acctgccacc aggcctggt aactttctgg    18000 tagttttagt agagacaggg tttcagcctc ccgagtagct gggattacag gcacctgcca    18060
ccaggcctgg gtaattttt tgcattttg gtagagacag gttttgccg tgttggcccg    18120 gctggtctca aactcctgac ctcaggttga cctgcccgct tgtccctcg caaagtgctg    18180 ggattacagg cgtgagccac cacacctggc ctgaatctga actttaaaa gggagttact    18240 gactctcaac tgtgcgggga cggtttcact ttgatttaat atggaaagag ggccaagtgt    18300
catcctcaca aatgggtccc cgaagcagat caaacgcaga gaactgtgag ggtgggacac    18360
gagtgtctgt ggacactggc tgcctttggc ttttctcctg cgagagaagt tgggtgactt    18420
tctgtaggtg gatgagtgat ccctgaatga gtgtggggta cgtgtatgct agctgcttct    18480
ttctccctga aactctcgga tggaaggaag taagaaattc agcttgggct gtgaccagtt    18540
```

```
ctcaccacca acgccctctt ctctctccct tctccttcct tccttccttc cttcctttct    18600
ttcttttct ttcttctct cttctttct tttctttctt tctgtttctt tccttttat        18660
ctttctctct ttttctttct cttttccttt tttgtttctt tctttctttt tctttctttc    18720
tttttctttc ttcttcttt cttcgatgaa gtctcactct gtcacccagg ctggagtgca    18780
gtggtgcaat cccagctcac tgcatcctct acctcctggc ttcaagaaat tctcctgcct    18840
cagcctccca gtagctggg atgacaggca cccaccacca ttcccggata attttgtat      18900
ttttagtag agactgggtt tcgccatgtt ggccaggctg tcttgaact cctgacctca      18960
catgatccac ccgcctcagc ctcccagagt gctgggatta cggggtgagg caccgcgccc    19020
ggcctcctct ctcttttct gagatgtta ggaaggactg ggctgatggg gaccctctgt      19080
atgtgatgtg cgtgggtttg gtttcccgga aggccctcca gagacacgtt tgcgtgaaca    19140
ttcagcatgg aaacaacata cgtctctcca caggaggtga gaaattgaat ttatggggtg    19200
ggtgtacgct ggcgattctt ggtgcttttt gctcaaaaca aggttctttt gaaagtcacg    19260
ttcctgcttt ccctgtggct tcccggtgag ctcgctcgca gagcaaggaa taccacccag    19320
agagcaacgt gggctgtgtt ccgttgtaac gccgttgcag agagaggatt tggtgtgtga    19380
gatccgtacc agctccagca cactgatagg aacacgttgc tggccgaact gaacgatgct    19440
gggttgggtc ctgattgata cgtatttct tccctcctct ccccaaaact tggccaaata    19500
gtccgtggag ggtgtcagt cgccgcagtt gagcaaaaaa cacttcttcc tttgagtggc    19560
tgttctggtg aaatctgttt ctgacatatc cactttctc tctcttttct ctctctctga    19620
ctgcgaagca cccacaggga gaaggaattg gatgtatcgg atgttggtat tagattttct    19680
ttctccgttc gagtctctga ctggtgcata ctttgcaaag gtgtgttcct ggcaattgcc    19740
aagagttaga aaatgcacc ttctctggtg gccgttgggg tgttgtttca caggcagtgg    19800
tgacagggcc ccttggctgt ggctgtcttc tccagcgccg tggataaaga gacgggacag    19860
attctgtgcc tctgtacgat ttagagcgta actgaccgcg tccaacaccc gttttccac    19920
ttacaaagct ggtggtgcga cgggcttggt gtctcccgta cgggaaggag gcctttgggc    19980
cgctccaaag acgccctgtc gtaggaatgg cctctccatc ccgccaaagt ccagccaggc    20040
ccccgaaatg gtcccatttc cttggaagcc tgagtttctg ttctggtctt gctgctgtcc    20100
ttggccacgt cagcacgtgg gagcatctgt ggataccgca gagtctgggg acagctgggc    20160
gtttaaccga aatgaagccg agacgggttt caggttttgg tgccaagctc tggtcaggat    20220
gaaagggaaa taccagagtc ctctgtcctc gcctctgggt ttcatgctga cctttctaac    20280
atttgttttc ccctaagaac aagcagaagc ctccagctcc cttagctcc acagttttcc    20340
cggggacata gcgaggatgg cacacggcag ccactcccac gacacacatt tcggaggcac    20400
tttgctggaa gccgcttgtc tcctccagct tgggaggtc tggggaggag agaggctttc    20460
ggtggacacg tttgacatta aaaaaaaaa aaaaaaaa aaaaaactg gtgcctaatt        20520
tattaaagag aattagctta gcgagtatat gctgatattc ttcgacacac gtgggtaagt    20580
tgatgccatt tataaatgtt ttattgaaat ttgatattta atgagaagcc ggttaaggaa    20640
tgtagacaat atcccgtttc aaagctatga aatgtgctat ttattgaaag gggatgtggc    20700
ttcacgagtt cagcccattg tacgtgcagg tcccgtggga aggaggcaaa agcccctgct    20760
tcttactttg tgatgtatgt gcatttgtta tttatttttt ttccttggt cggacgttca    20820
taaatatgta ctatttaat tatgtcgagt gtaaatttga catcgcgttg catttatttt    20880
```

```
tatatttctg aaaactgttg cttttctttt ttccctcccc cattgacgac atagcggccc   20940
ccgcgtccgg gttacaaata catctacaga tattttcagg gattgcttca gatgaaaaca   21000
aatcacacac cgtttcccaa accaacagtc ttcacatttc tatccctctg ttattgtcgg   21060
caggcggtga ggggtagaaa aaaacaaac aaacaaacag aaaaaaaaac caaaaaaaac    21120 cacccctgagt ttctctggtg acgccctcat tctcctaacg ttcaataatc tcaatgttga   21180
gttgcagcaa cagactgtat ttttgtgacg ccccgtagta tgaatgtaca tcttgtaaaa   21240
ctgagatata aataaactta taaatatttg tattcaagtg ttaaaaaaaa aaaaattctc   21300
aacctctccc ctgaggacag gcttattgga aaaaaaaaaa aaaaaaaaaa atcctgagtc   21360
ggccgtggct gaacacagag tgttgttctg ctccgtgcat ttccagggtg ggtacccagt   21420 gttgccccc agccttagat cgggaggtac cattgacttt tgcttgtatc ccatcccctt    21480
cctttactga aacctacctc cccgcttctc agccaacgtc cccccagaag gtggcaaaaa   21540
aaacagagga aaaagccctg atttgaatca agtcagagct gctaattctc cactttcttt   21600
aattaattaa tttatttttt tttttgagac tgagtctcgc tctgtcgccc aggccggagg   21660
agtgcagggg cgcgatctcg gctcaccgcg acctccgcct cccggttca agcgactctc     21720 ctgcctcagc ctcccgagta gctgggatga cagtcacctg caccaccgcg cccggctcat   21780
ttttgtattt ttagtagcaa tggggtttca ccgtgttggt caggctggtc tcgaactcct   21840
gacctcgtga tccacccgcg tctgggcccg gccggtgatg tgtgtgcttt taacttttat   21900
tttgttccag tttttcgacag tggcacggat tttccagcac ggtcttgcaa ggatgattga   21960
gtcatttttg agacaaaaaa tataataata ataaatgaaa aagaaatcg acttttaaaa    22020 atgacaaatt tttttttttt tttttttgcat agattttttct ctctttatgt aaaggaaagt  22080
tcatgattgg atttggccgg cctgactgct tcccggctgt gataaaaaac acatgtgagc   22140
tgggagggaa gtgggggagg gacacagctg cccacacagg gttccaccg cggttacagg    22200 gtgggcagtg ctgggggagc tttctctgtg gggggctcag agcctgagga caggtgagcc   22260
tctccgacac ctccccagtt gcctggagtc taaaccgtcc gttgtctgta ccgtccgttc   22320
ttcctgctga ctcctggtag ttcctgaaag cttctcttgg ccagagaagg ggtttcagag   22380
gccgtgtgtc caggccattc tgcaaagtgc aacttgaccg ttccttttcct tttctggcct  22440 gcgtggtctg aagctcagag ccctctcttc acccagcctg tgtgtgtctt gccggacaga   22500
agaaaaatgg tgctttttgc gtgttagcag aggtgctttt catggctgac ctcaacgcgt   22560
ccatctccag ccttgaccaa gctgtttttt aggggcaaac gcaggcaagt tctgaatgca   22620
cacagttatt tcatggttaa actattcagc tttggccggg cgcagtgtgg ctctcacgcc   22680
tgtcatccca gcactttggg aggccgaggc gggtggatca cctgaggtca ggagttcgag   22740
accagcctgg ccaacacggt gaaactctat ctctactaaa aatacaaaaa ttagccgggc   22800
gtggtggtgt gtatctgtaa tcccagctac tcaggaagct gaggcaggag aatcgcttgg   22860
acccaggagg cggaggttgc actgagccga gatcgcgcca ttgcactcca gcctgggcga   22920
cagagccaga cgctgtctca aaaaatgaa taataaaata aaataacagg aactaaataa    22980
aataaaacgt tcagctttgt tctgcaaatc cactcctatt gttttacgtg gtttgagaga   23040
ctctgtccct tagaaatagaa tgtttgttgc caattgtaat gaatctgttt caaaaatgaa   23100
cagaatattc aaatggtttg agagatcttt tcccttagaa atagcttgtt gccaatcaca   23160
aagaatgttt tcaaaaatg aatggaatct tcctggatat cgcttccaga tcttcatttt    23220
ttttgcatag ttcaacctga aaagtaagtg tctcagccct gaatttcttt ctgatttttc   23280
```

```
catgggttgt cttgcagact tctctggact tgaccacatt taaaaaaaaa aaaattaact    23340
ttttcacacg gacacggttt caataggaat gagatctttg agttttatg taacagattc    23400 ttaccatcag ttctcagatt cccaaattac acacaaaaag ccacggactt cgcctcctgc    23460
taacatgtcc ttctgtttct gaggcttctg ttggtgttag actttcatgt ttaatagcag    23520
acaatgtagg gatttaaaga aaaatgcaga gaaagcaaaa acactgacca aacacacgga    23580
gataagcttt ctaaagcctt tgttcttgga gttgtcgtta aaaaaaaaa gttgttttaa    23640 actttgcaag catgcctata ttgaactcat aagcaagaga gccaagaaaa atagtgtcgg    23700
tcgtctactc tacacgtttt cccaaaacag acgtatttta atttcttttg tttgaactca    23760
cagatgctga gagttaaaag ttaaattttt gtcatgaaca atagtggcca aaaccacagt    23820
tacttttgca ctatagcata ataagaaaaa tacaggctgg gctcggtggc tcacacctgt    23880
aatcaaagca cttttggagg cgaaacagcc agatcccttg agcccaggag attgagacca    23940
gcctgggcaa catagcgaga ccctcatctc tacaaaaaag gtttgttaca tatgtaacaa    24000
acctgcacat tgtgcacatg taccctaaaa cttaaagtat aataataaaa aaattaaaaa    24060
aaaattcacc aatcaactgc ctgctggtgc cttcaagaga ctcacctaac ataaggac    24120 ttgcataaac ttataaaaca attcaatgga agaatccttg aaagtattct gagaagacag    24180
tataataaac tgatttctaa aaaggctata aaaaattgaa taaatcattg ttgggcatcc    24240
tgtgctgaaa tataatgcag ccaataaaaa ttacaaaatg aataaacatt ttataacaat    24300
aaaaaaaagt caaataatta ggcaggcatg gtggtgctct cctacggttg aagctattca    24360
gcaggcaaga ggatactttg ttttttgtttt ttaatttttt ttgagacaga gtctcgctct    24420
gttgccaggc tggagtgcag tggcgtgatc tcagctcact gtaatttctg cctcccgggt    24480
tcaagcgatt ttcctgcccc agcctcccga gtagctggga ttacaggtgc ccgccaccac    24540
acctggctaa tttcttttgt attttagta gagacgaggt ttccccatgt tggccaggct    24600
ggttttgagc tcccgacctc gggtgatcca cccgcctcag cctcccaaag tgctgggatg    24660
acaggcgtga gccaccgcgc ctggcccagg aggattattt gatcccagga ggtggaggct    24720
gcaggaagcc atgattgcac cactgcactc cagcctggct gacagagtga gaccacatct    24780
ctaaataaat gaataaatac aggcagaaac tttttttgtt ttgttttgat ggagtcttgc    24840
tctgtcacca ggcaggagtg cagtggtgcc atctcagctc actgcaacct ccacctcctg    24900
ggttcaagca atcctcctgc ctcagcctcc cgagtagctg ggattacagg tgcccgccac    24960
cacgcccggc taattttttg tatgtttagt agagacggga tttcaccgtg ttagccagga    25020
tggtcttgat ctcttgactt tgtgatctgc ctgcctcagc ctcccaaagt gctgggatta    25080
caggcatgag cccaggagtt caagaccagc ctcagcaaca aagtgagacc ttttctctcc    25140
aaaaaatcaa aaatttagcc agctgtggtg gctcctgccc gtgatcccag tactgtggga    25200
ggctgaggca gaattgcttg agcccaggag ttcgagacca acctcagcaa aaaggactct    25260
ctctctctct ctctctctct ctctctctct ctctctatat atatatatat atatatatat    25320
gagtttcaaa aattgctggg tgaccagctc atctactggt tttccccttg ggaaagtgaa    25380
attgtcatgt attgaagatt tccaaggaag ttgtattgaa tgagaaacaa actcaatctg    25440
ttcgtgttta aagagctgca gtgcgtttgc tgtgtttccc ataaaactgc acttccaaaa    25500
gacacgctga gaaggagac caggatttgt aattcagaaa ttggaaagca agttaggctg    25560
gacgtggtag ctcatgcttg ttgtaatctc agcactctgg gaggctgagg caggaggatc    25620
```

```
acttgagccc aggagttcaa gaccagcccg tgccacatgg tgaaaccctg tctctccaaa   25680
aaataaaaca tttagccaga tgtggtgact catgcctgta atcccggtat tctgggaggc   25740
tgaggcagag ttgcttgagc ccaggagttc aagaccagcc tcggcaacaa agtgagaccc   25800
tgtctctcca aaaataaaa catttagcca gctgtggtga ctcatgcctg taatctcagt   25860
actctgggag gctggggcag aatggcttga gcccaggagt tcgagaccaa cctcagcaac   25920
aaagtgagat cttgtttctc caaaaaatca aaaatttagc cagctgtgct ggctcatgcc   25980
tgtaatcccg gtactctggg aggctgaggc agaatcgttt gagcccagga gttcgagacc   26040
aacctcagca acaaagtgag atcttgtttc tccaaaaaaa tcaaaaattt agccagctgt   26100
gctggctggt gcctgtaatc ccggtactct gggaggctga ggcggaattg cttgagccca   26160
ggagttcaag accagcctca gcaacaaagt gagatcttgt ttctccaaaa aataaaacat   26220
ttagtcagct gtggtggctc aagcctgtga tcccagcatt tgggaggcc gaggcgggcg   26280 gatcacgagg tcatgagatc gagaccatcc tggctaacac ggtgaaaccc cgtctctact   26340
aaaaatacaa agaaaattag ccgggcgtgg tggcgggcgc ctgtagtccc agctactcag   26400
gaggctgagg caggagaatg ccgtgagcct gggaggcgga ccatgcagtg agtcaagatc   26460
gcgccactgc cctccagcct gggccacaga gcaagactcc gtctcaaaaa aaaaaaaaa   26520 aaaactgctg cccaacctgt gtttgcacca ctgccctcca gcctgggcaa cagagcaaga   26580
ctccgtctca aaaaaaaaa aatgctgccc aagctgtgtt tgcaccactg ccctccagcc   26640
tgggcaacag agcaagactc cgtctcaaaa aaaaaaaaa aaaatgctgc caagctgtg   26700 tttgcaccac tgccctccag cctgggcaac agagcaagac tctgtctcaa aaaaaaaaa   26760 aatgctgccc aagctgtgtt tgcaccactg ccctccggcc tgggcaacag agcaagactc   26820
cgtctcaaaa aaaaaaaaa aatgctgccc aagctgtgtt tgcaccactg ccctccagcc   26880
tgggcaacaa agcaagcctc agctttctgc catctccaca accaagaaag caattcacac   26940
agaaatcagt gcatcgtgca gtgacctctt cagaaaacca atgagttttc cacctgagga   27000 actgttctg agccccattc agaaaaacac atccctgtaa ctgcagggca gatttactca   27060
ctgtatgcct gtttaaataa agcttccagc ctctgcatgg ggtctgtctg gaagctcctg   27120
tatctgtccc acattcttgg aatcacaatg caccctaggg aggaagatat gtatttaaag   27180
ggagtggatg ttatggtgag aaaatgctgc ccatccttct agaagacaaa agccacacaa   27240
aatacatcac aagaaccagt ttttttcaga gaagaacctg cacaaagaac ctgctccccc   27300 cacacccca cacacaggtg aattaacagg atgtatgttt tatcataaaa gcacaggttt   27360
gtttcctatg cactctctga ggatttggcc atatgcaaag atgtacaaaa accttctctt   27420
tccccaggga accgtaaccc gtctgaaaag atgcccttct cagaagcgag ttgaacgatt   27480
gttggaaaag ataaaatacg acgtgcacac acacagtaga gaaatgtcac ccatgcaaat   27540
tatgtgtttg aatggaacac attcaggaag ctaaatgggg tatgaccaca catttgggtt   27600
gatttatttg acgagtggaa ggggcagatg gaaatgaata ctgctgtttt cctttggaag   27660
gccatatatg ggaataccaa gaggattact ttggaagttt agcttctcca ggtggtctct   27720
ctctctctct cttttttga gacagagtct cactctgtca cccaggctgc agtgcaatgg   27780
cgtgctctcg gctcactgca acctcagcct cccaggtaca agcgattctc ctgcctcagc   27840
ctcccgagta gctgggatca caggtgtgca ccaccacgcc tggctaatgt ttgtattttc   27900
agtagagatg aggttttacc atgttggcca ggctggtctt gaactcctga cctcaggtga   27960
tccgcctgcc tcggcctccc aaagtgctgg gatgacagac atgagctagc acgcccggcc   28020
```

```
ccaggtggtc tttttagcgg gtattaaagc agctttctct ctgagcctta aaccatgaag    28080
atagacagac tcagtgtatg ggttttagag ttgtaatttt ataaaaataa gaaaaagtcg    28140
acctatcatt gatggttagt atttttttgta gcagttgcat gcaatattag gataaggcat   28200
gttctcaaaa agaactcttt tttttttttt tttgagacgg agtctcgctc tgtcacccag    28260
gctggagtgc agtggcacga tctccgctca ctgcaagctc ctcttcccgg gttcacgcca    28320
ttctcctgcc tcagcctccc cagtagctgg gactacaggc gcccgccacc acgcccggct    28380
aattttttgt attttttagta gagacggggt ttcaccatgt tagccaggaa ggtctcgatc   28440
tcctgacctc atgatccgtc cgcctcagcc tcccaaagtg ctgggactac aggcgtgagc    28500
cactgcactt ggcctttttt ttttttttaga tggagtttttg ctcttgtcgc ccaggctgga  28560
gtataatggc atgatctcga ctcactgcaa cctccgcctc ccgagttcaa gcgattctcc    28620
tgcctcagcc tcccgagtag ctgggattac aggtgcccac caccatgtca agataatgtt    28680
tgtattttca gtagagatgg ggtttgacca tgttggccag gctggtctcg aactcctgac    28740
ctcaggtgat ccacccgcct tagcctccca aagtgctggg atgacaggcg tgagcccctg    28800
cgcccggcct ttgtaacttt atttttaatt tttttttttt tttaagaaag acagagtctt    28860
gctctgtcac ccaggctgga gcacactggt gcgatcatag ctcactgcag cctcaaactc    28920
ctgggctcaa gcaatcctcc cacctcagcc tcctgagtag ctgggactac aggcacccac    28980
caccacaccc agctaatttt tttgattttt actagagacg ggatcttgct ttgctgctga    29040
ggctggtctt gagctcctga gctccaaaga tcctctcacc tccacctccc aaagtgttag    29100
aattacaagc atgaaccact gcccgtggtc tccaaaaaaa ggactgttac gtggatgttc    29160
tagcttcctg ttctcgtctt ttctttgtta attgtacagt ttgagggtgt gtgtgcgtgt    29220
gcgcacgtgt gtgtgtgcag tctcctgatt tcatgtatttt aattgttatt accaccacct   29280
ccatctctca ttccttctta ccctcactgt gtaaagatac atgttgtttt taaattttat    29340
gtatttatat ttatttattt gtatttctga gacagagtct cactctgttg cccaggctag    29400
tggcatgatc tcagctcaca gcaaccttttg cctcctgggt tcaagcgatt ctcctgcctc   29460
agcctcccga gtagctgaga ttacaggcac acaccaccac acccggctag ttttgttttg    29520
agacggagtc tcgctctgtt gcaggctgca gtgcagtggc gtgatcctgg ctcactgcaa    29580
cctctgcctc ctggattcaa gcgattctcc tgcctcagcc tcccaagtag ctgggattac    29640
aggcgcccac cgccacacct ggctaatttt ttattggtag tagagacggg gtttctccat    29700
gttgaccaga ctggtcttga actcccaacc tcgggtgatc cacccacctg gcctcccaa     29760 agtgctggga tgacaggcga gggccaccgc gtccagcctt cttcttcttc ttctttttt    29820 tttttttaag atggagtttc actctgttgc ccaggctgga gtgcagtggt gcaatctcgg    29880
ctccctgcaa cctccacctc ccaggttcaa gaaattcttt tgcctcagcc tcccgagtag    29940
ctgggactac aggtgcccgc caccacaccc acctaatgtt tgtatttttt tggtagagac    30000
ggggcttcac cacattggcc aggctggtct tgaactcctg acttcagatg atcctcctgc    30060
ctcagcctcc cagagtgttg ggattacagg cgtgagccac ggtgcccggc cagacgtcat    30120
gtcttaggaa atcagaaagt gggtagtttc cgcactctga ggagaaaaag agacgtccgg    30180
cgaagagaaa ggagagtgaa aggatgtctc ctcttgtctg tagcctgttc tcaatcgtga    30240
gtgagccaat tgccagaaac tgagggtgct tcatttggcc aggcaagctt ctcaacagaa    30300
tgtctaagta cttgttaatg ctgagaagct ctccaagcta ctgcactcca gcctgggtga    30360
```

-continued

```
cagagcacga ccttgtctga aaacaattaa ttaatcaatt aattaatata atgaaatcat    30420
actgaactca ggagaccatt ggggtgggca ggctggggt tggaaaggaa cataaaatat    30480
ggtgcaatgg actttgctcc agtctccctc cccatctctt ctcgccaaga gtctctggag    30540
ggagcatggg gaagatgctt tgggaatctg taacttcttg tcttgtaaac agaatatcta    30600
agtaattgtt aatgctgaga agttatagat ttccaaagcc tttctccagg ctacggacaa    30660
gggtcatggg ttactcagtg ttacagaaag aatgacatgg agatgtttgt tacatcttaa    30720
ggaaccatga ggggccagag tattttactc taagtgtaga tggtacattg gccacgcctg    30780
tcccaacacc accaatggtg gcacctaact tttgtgtttg tgccccacat ttcttcttct    30840
tttctgacgt aaatgcaagt gatattcctt ggaaaccatg ctgcagcaag aggccatctg    30900
actactagta taccctgta gctcacctac agcagctcac ttgaagcagc tcacccatag    30960
ctcaggtata gctcacctgc agcggctcac ctgtagctca cgtgtagctc acttgtagca    31020
gctcactggt agctcacctg cagcagctca cctgtacctc acctgtacct cacctgcagc    31080
agctcacctg tagctcacct gtacgtgagc caccgtaccc ggccagcaag accccatttc    31140
taaaataaat acacaaaaat tagccggacg cggtggcgcg tgtctgtagt tgtagctact    31200
caggaggctg aggtgggagg attgctggag gctgggaggt agaggctgca gtgaaccgtg    31260
atccagccac tgtactctag cctggatgac atagcaaaac cttgtctcaa aaacaaaaa    31320
caaaaacaa aacaaagaaa caaacaaaaa acccacacac accggaaaac aaaacaaaaa    31380
gcaaaaagga aagaaaagag agccaggtcc caaatatata ttttccttgga gaaccatttg    31440
caaagagcac acttaaggcc gggcgcggtg gctcacgcct gtcatcccgg cactttggga    31500
ggccgaggtg ggtggatcac gaggttggga gatcgagacc atcctggcca acatggcgaa    31560
accccatctc tactaaaaat acaaaaaatc agccaggtgc tgaggcaggt gcctgtagtc    31620
ccagccactc aggaggctga ggcaggagaa tggcatgaac ctgggaggtg gaggttgcag    31680
tgagccgaga tcgcgcccct gcactccagc ctgggcgaca gagcgagact ccttctcaaa    31740
taaataaata aataaataac aaagagcaaa cttaaaattg tctcagaaat cccacgggat    31800
attggatctc cctcatgcct atctgatgac actttgagtg tctggggccc cgtgcctatt    31860
ttctggggtt cccagaagct gccgttctga aagtgtggct ctcggggacg tggcacaggt    31920
gtggatgtct gttttaaatg tcaggcgttt ggacgttgag gaacgtgagg ctgaaggtcg    31980
ccttcgccga cccctgagt ttagggtcct gccttttaaa atcttcccag cactctgttg    32040
ttcacgcaag cgtcccatct gtttgggtgg ccgtgccgtc tgcatctgtc tcgaaccttc    32100
acagctttgc agaatatcct gtttctcaat acggatggag aaacacgaga cgcgttttct    32160
gggttatttt agccgtcacg gagaacccca gactcatgtg tgctaatgac ctcattaatg    32220
atactctgag gcagacagcc ctgcctgatc ttaacaacat ttttttaaatt tcttttttttg    32280
ttgttgttgt tacagcatca ttcatataac gtaggaaacc gtgatcagta gcttttagga    32340
tatttgcaac agggtgtaac adaaabd                                        32367
```

<210> SEQ ID NO 15
<211> LENGTH: 806
<212> TYPE: DNA
<213> ORGANISM: Homo sapiens
<220> FEATURE:
<221> NAME/KEY: CDS
<222> LOCATION: (43)..(612)
<220> FEATURE:
<221> NAME/KEY: misc_feature
<222> LOCATION: (667)

```
<223> OTHER INFORMATION: a, c, t, g, other or unknown
<220> FEATURE:
<221> NAME/KEY: misc_feature
<222> LOCATION: (672)
<223> OTHER INFORMATION: a, c, t, g, other or unknown
<220> FEATURE:
<221> NAME/KEY: misc_feature
<222> LOCATION: (677)
<223> OTHER INFORMATION: a, c, t, g, other or unknown
<220> FEATURE:
<221> NAME/KEY: misc_feature
<222> LOCATION: (723)..(724)
<223> OTHER INFORMATION: a, c, t, g, other or unknown

<400> SEQUENCE: 15
gtgtccccgg agctgaaaga tcgcaaagag gatgcgaaag gg atg gag gac gaa         54
                                             Met Glu Asp Glu
                                              1 ggc cag acc aaa atc aag cag agg cga agt cgg acc aat ttc acc ctg       102
Gly Gln Thr Lys Ile Lys Gln Arg Arg Ser Arg Thr Asn Phe Thr Leu
  5                  10                  15                  20 gaa caa ctc aat gag ctg gag agg ctt ttt gac gag acc cac tat ccc       150
Glu Gln Leu Asn Glu Leu Glu Arg Leu Phe Asp Glu Thr His Tyr Pro
                 25                  30                  35 gac gcc ttc atg cga gag gaa ctg agc cag cga ctg gcc ctg tcg gag       198
Asp Ala Phe Met Arg Glu Glu Leu Ser Gln Arg Leu Gly Leu Ser Glu
             40                  45                  50 gcc cga gtg cag gtt tgg ttt caa aat cga aga gct aaa tgt aga aaa       246
Ala Arg Val Gln Val Trp Phe Gln Asn Arg Arg Ala Lys Cys Arg Lys
         55                  60                  65 caa gaa aat caa ctc cat aaa ggt gtt ctc ata ggg gcc gcc agc cag       294
Gln Glu Asn Gln Leu His Lys Gly Val Leu Ile Gly Ala Ala Ser Gln
     70                  75                  80 ttt gaa gct tgt aga gtc gca cct tat gtc aac gta ggt gct tta agg       342
Phe Glu Ala Cys Arg Val Ala Pro Tyr Val Asn Val Gly Ala Leu Arg
 85                  90                  95                 100 atg cca ttt cag cag gtt cag gcg cag ctg cag ctg gac agc gct gtg       390
Met Pro Phe Gln Gln Val Gln Ala Gln Leu Gln Leu Asp Ser Ala Val
                105                 110                 115 gcg cac gcg cac cac cac ctg cat ccg cac ctg gcc gcg cac gcg ccc       438
Ala His Ala His His His Leu His Pro His Leu Ala Ala His Ala Pro
            120                 125                 130 tac atg atg ttc cca gca ccg ccc ttc gga ctg ccg ctc gcc acg ctg       486
Tyr Met Met Phe Pro Ala Pro Pro Phe Gly Leu Pro Leu Ala Thr Leu
        135                 140                 145 gcc gcg gat tcg gct tcc gcc gcc tcg gta gtg gcg gcc gca gca gcc       534
Ala Ala Asp Ser Ala Ser Ala Ala Ser Val Val Ala Ala Ala Ala Ala
150                 155                 160 gcc aag acc acc agc aag gac tcc agc atc gcc gat ctc aga ctg aaa       582
Ala Lys Thr Thr Ser Lys Asp Ser Ser Ile Ala Asp Leu Arg Leu Lys
165                 170                 175                 180 gcc aaa aag cac gcc gca gcc ctg ggt ctg tgacvccaac gccagcacca        632
Ala Lys Lys His Ala Ala Ala Leu Gly Leu
                185                 190 atgtcgcgcc tgtcccgcgg cactcagcct gcasnccctn ddkanmcgtt rctyhtcmat   692
tacactttgg gaccycgggd bagvcctttt nnagacttyv atkggscwcs ctggbccctb   752
rkgavvactt gsghycgrga accgakhtgc ccabaygagg accrgtttgg akdg         806

<210> SEQ ID NO 16
<211> LENGTH: 190
<212> TYPE: PRT
<213> ORGANISM: Homo sapiens
```

<400> SEQUENCE: 16

Met Glu Asp Glu Gly Gln Thr Lys Ile Lys Gln Arg Arg Ser Arg Thr
1               5                   10                  15

Asn Phe Thr Leu Glu Gln Leu Asn Glu Leu Glu Arg Leu Phe Asp Glu
            20                  25                  30

Thr His Tyr Pro Asp Ala Phe Met Arg Glu Glu Leu Ser Gln Arg Leu
        35                  40                  45

Gly Leu Ser Glu Ala Arg Val Gln Val Trp Phe Gln Asn Arg Arg Ala
    50                  55                  60

Lys Cys Arg Lys Gln Glu Asn Gln Leu His Lys Gly Val Leu Ile Gly
65                  70                  75                  80

Ala Ala Ser Gln Phe Glu Ala Cys Arg Val Ala Pro Tyr Val Asn Val
                85                  90                  95

Gly Ala Leu Arg Met Pro Phe Gln Gln Val Gln Ala Gln Leu Gln Leu
            100                 105                 110

Asp Ser Ala Val Ala His Ala His His Leu His Pro His Leu Ala
        115                 120                 125

Ala His Ala Pro Tyr Met Met Phe Pro Ala Pro Pro Phe Gly Leu Pro
    130                 135                 140

Leu Ala Thr Leu Ala Ala Asp Ser Ala Ser Ala Ala Ser Val Val Ala
145                 150                 155                 160

Ala Ala Ala Ala Ala Lys Thr Thr Ser Lys Asp Ser Ser Ile Ala Asp
                165                 170                 175

Leu Arg Leu Lys Ala Lys Lys His Ala Ala Leu Gly Leu
            180                 185                 190

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 17
gcacagccaa ccacctag                                                    18

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: synthetic
      primer

<400> SEQUENCE: 18
tggaaaggca tcatccgtaa g                                                21

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 19
atttccaatg gaaaggcgta aataac                                           26

```
<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 20
acggcttttg tatccaagtc ttttg                                          25

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 21
gccctgtgcc ctccgctccc                                                20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 22
ggctcttcac atctctctct gcttc                                          25

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 23
ccacactgac acctgctccc tttg                                           24

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 24
cccgcaggtc caggctcagc tg                                             22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: synthetic
      primer

<400> SEQUENCE: 25
cgcctccgcc gttaccgtcc ttg                                            23

<210> SEQ ID NO 26
```

```
<211> LENGTH: 21
<212> TYPE: DNA
<213> ORGANISM: Artificial Sequence
<220> FEATURE:
<223> OTHER INFORMATION: Description of Artificial Sequence: synthetic
      primer

<400> SEQUENCE: 26
ccctggagcc ggcgcgcaaa g                                              21

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 27
ccccgccccc gccccgg                                                   18

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: synthetic
      primer

<400> SEQUENCE: 28
cttcaggtcc ccccagtccc g                                              21

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 29
ctagggatct tcagaggaag aaaaag                                         26

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 30
gctgcgcggc gggtcagagc cccag                                          25

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: synthetic
      primer
<220> FEATURE:
<221> NAME/KEY: misc_feature
<222> LOCATION: (21)..(40)
<223> OTHER INFORMATION: thymine nucleotide is a dideoxyribonucleic acid
<220> FEATURE:
<221> NAME/KEY: misc_feature
<222> LOCATION: (41)
<223> OTHER INFORMATION: a, c, t, g, other or unknown
```

```
<400> SEQUENCE: 31
ggccacgcgt cgactagtac tttttttttt tttttttttt n                 41

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 32
gaaaggcatc cgtaaggctc cc                                      22

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 33
gacgccttta tgcatctgat tctc                                    24

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 34
gaatcagatg cataaaggcg tc                                      22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 35
gggagcctta cggatgcctt tc                                      22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 36
agccccggct gctcgccagc                                         20

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: synthetic
      primer
```

-continued

```
<400> SEQUENCE: 37
ctgcgcggcg ggtcagagcc ccag                                              24

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 38
agccccggct gctcgccagc                                                   20

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 39
gcctcagcag caaagcaaga tccc                                              24

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 40
gctgagcctg gacctgttgg aaagg                                             25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 41
gctgagcctg gacctgttgg aaagg                                             25

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Ser Lys Ser Phe Asp Gln Lys Ser Lys Asp Gly Asn Gly Gly
  1               5                  10                  15

<210> SEQ ID NO 43
<211> LENGTH: 1541
<212> TYPE: DNA
<213> ORGANISM: Homo sapiens
<220> FEATURE:
<221> NAME/KEY: CDS
<222> LOCATION: (43)..(612)
```

<400> SEQUENCE: 43

```
gtgtccccgg agctgaaaga tcgcaaagag gatgcgaaag gg atg gag gac gaa              54
                                              Met Glu Asp Glu
                                                1 ggc cag acc aaa atc aag cag agg cga agt cgg acc aat ttc acc ctg           102
Gly Gln Thr Lys Ile Lys Gln Arg Arg Ser Arg Thr Asn Phe Thr Leu
  5              10                  15                  20 gaa caa ctc aat gag ctg gag agg ctt ttt gac gag acc cac tat ccc           150
Glu Gln Leu Asn Glu Leu Glu Arg Leu Phe Asp Glu Thr His Tyr Pro
              25                  30                  35 gac gcc ttc atg cga gag gaa ctg agc cag cga ctg ggc ctg tcg gag           198
Asp Ala Phe Met Arg Glu Glu Leu Ser Gln Arg Leu Gly Leu Ser Glu
         40                  45                  50 gcc cga gtg cag gtt tgg ttt caa aat cga aga gct aaa tgt aga aaa           246
Ala Arg Val Gln Val Trp Phe Gln Asn Arg Arg Ala Lys Cys Arg Lys
     55                  60                  65 caa gaa aat caa ctc cat aaa ggt gtt ctc ata ggg gcc gcc agc cag           294
Gln Glu Asn Gln Leu His Lys Gly Val Leu Ile Gly Ala Ala Ser Gln
 70                  75                  80 ttt gaa gct tgt aga gtc gca cct tat gtc aac gta ggt gct tta agg           342
Phe Glu Ala Cys Arg Val Ala Pro Tyr Val Asn Val Gly Ala Leu Arg
 85                  90                  95                 100 atg cca ttt cag cag gtt cag gcg cag ctg cag ctg gac agc gct gtg           390
Met Pro Phe Gln Gln Val Gln Ala Gln Leu Gln Leu Asp Ser Ala Val
                105                 110                 115 gcg cac gcg cac cac cac ctg cat ccg cac ctg gcc gcg cac gcg ccc           438
Ala His Ala His His His Leu His Pro His Leu Ala Ala His Ala Pro
                120                 125                 130 tac atg atg ttc cca gca ccg ccc ttc gga ctg ccg ctc gcc acg ctg           486
Tyr Met Met Phe Pro Ala Pro Pro Phe Gly Leu Pro Leu Ala Thr Leu
            135                 140                 145 gcc gcg gat tcg gct tcc gcc gcc tcg gta gtg gcg gcc gca gca gcc           534
Ala Ala Asp Ser Ala Ser Ala Ala Ser Val Val Ala Ala Ala Ala Ala
        150                 155                 160 gcc aag acc acc agc aag gac tcc agc atc gcc gat ctc aga ctg aaa           582
Ala Lys Thr Thr Ser Lys Asp Ser Ser Ile Ala Asp Leu Arg Leu Lys
165                 170                 175                 180 gcc aaa aag cac gcc gca gcc ctg ggt ctg tgacgccaac gccagcacca            632
Ala Lys Lys His Ala Ala Ala Leu Gly Leu
                185                 190 atgtcgcgcc tgtcccgcgg cactcagcct gcacgccctc cgcgccccgc tgcttctccg         692
ttaccccttt gagacctcgg gagccggccc tcttcccgcc tcactgacca tccctcgtcc         752
cctatcgcat cttggactcg gaaagccaga ctccacgcag gaccagggat ctcacgaggc         812
acgcaggctc cgtggctcct gcccgttttc ctactcgagg gcctagaatt gggttttgta         872
ggagcgggtt tgggggagtc tggagagaga ctggacaggg tagtgctgga accgcggagt         932
ttggctcacc gcaaagctac aacgatggac tcttgcatag aaaaaaaaaa tcttgttaac         992
aatgaaaaaa tgagcaaaca aaaaaatcga agacaaacg ggagagaaaa agaggaaggc        1052
aacttatttc ttaactgcta tttggcagaa gctgaaattg agaaccaag gagcaaaaac        1112
aaattttaaa attaaagtat tttatacatt taaaaatatg gaaaacaac ccagacgatt        1172
ctcgagagac tgggggagt taccaactta aatgtgtgtt ttaaaaatg cgctaagaag        1232
gcaaagcaga aagaagaggt atacttattt aaaaaactaa gatgaaaaaa gtgcgcaggt        1292
gggaagttca caggttttga aactgacctt tttctgcgaa gttcacgtta atacgagaaa        1352
tttgatgaga gaggcgggcc tccttttacg ttgaatcaga tgctttgagt ttaaacccac        1412
```

-continued

```
catgtatgga agagcaagaa aagagaaaat attaaaacga ggagagagaa aaataatggc    1472
aaaactgtct ggactgctga cagtaaattc cggtttgcat ggaaaaaaaa aaaaaaaaaa    1532
aaaaaaaaa                                                            1541

<210> SEQ ID NO 44
<211> LENGTH: 10
<212> TYPE: DNA
<213> ORGANISM: Homo sapiens

<400> SEQUENCE: 44
gtgatccacc                                                            10

<210> SEQ ID NO 45
<211> LENGTH: 20
<212> TYPE: DNA
<213> ORGANISM: Homo sapiens

<400> SEQUENCE: 45
ccccacgcag ggatttatga                                                 20

<210> SEQ ID NO 46
<211> LENGTH: 20
<212> TYPE: DNA
<213> ORGANISM: Homo sapiens

<400> SEQUENCE: 46
tctccccaag gtttggttcc                                                 20

<210> SEQ ID NO 47
<211> LENGTH: 20
<212> TYPE: DNA
<213> ORGANISM: Homo sapiens

<400> SEQUENCE: 47
ttggacacag gcgtcatctt                                                 20

<210> SEQ ID NO 48
<211> LENGTH: 20
<212> TYPE: DNA
<213> ORGANISM: Homo sapiens

<400> SEQUENCE: 48
gctcccgcag gtccaggctc                                                 20

<210> SEQ ID NO 49
<211> LENGTH: 20
<212> TYPE: DNA
<213> ORGANISM: Homo sapiens

<400> SEQUENCE: 49 tttttttag atggagtttt                                                  20

<210> SEQ ID NO 50
<211> LENGTH: 20
<212> TYPE: DNA
<213> ORGANISM: Homo sapiens

<400> SEQUENCE: 50
gtggcagaag gtaagttcct                                                 20

<210> SEQ ID NO 51
```

```
<211> LENGTH: 20
<212> TYPE: DNA
<213> ORGANISM: Homo sapiens

<400> SEQUENCE: 51
gcgcgtgcag gtaggaaccc                                              20

<210> SEQ ID NO 52
<211> LENGTH: 20
<212> TYPE: DNA
<213> ORGANISM: Homo sapiens

<400> SEQUENCE: 52
atgcataaag gtgggtgtcg                                              20

<210> SEQ ID NO 53
<211> LENGTH: 20
<212> TYPE: DNA
<213> ORGANISM: Homo sapiens

<400> SEQUENCE: 53
tttccaacag gtagctcact                                              20

<210> SEQ ID NO 54
<211> LENGTH: 10
<212> TYPE: DNA
<213> ORGANISM: Homo sapiens

<400> SEQUENCE: 54
aaaaaatagc                                                         10

<210> SEQ ID NO 55
<211> LENGTH: 10
<212> TYPE: DNA
<213> ORGANISM: Homo sapiens

<400> SEQUENCE: 55
tgttacgtgg                                                         10
```

HUMAN GROWTH GENE AND SHORT STATURE GENE REGION

This application is a continuation of case Ser. No. 09/147,699, filed on Jun. 24, 1999, now abandoned, which is a 371 case of PCT/EP97/05355, filed on Sep. 29, 1997 which claims benefit of U.S. provisional application 60/027,633, filed on Oct. 1, 1996.

The present invention relates to the isolation, identification and characterization of newly identified human genes responsible for disorders relating to human growth, especially for short stature or Turner syndrome, as well as the diagnosis and therapy of such disorders.

The isolated genomic DNA or fragments thereof can be used for pharmaceutical purposes or as diagnostic tools or reagents for identification or characterization of the genetic defect involved in such disorders. Subject of the present invention are further human growth proteins (transcription factors A, B and C) which are expressed after transcription of said DNA into RNA or mRNA and which can be used in the therapeutic treatment of disorders related to mutations in said genes. The invention further relates to appropriate cDNA sequences which can be used for the preparation of recombinant proteins suitable for the treatment of such disorders. Subject of the invention are further plasmid vectors for the expression of the DNA of these genes and appropriate cells containing such DNAs. It is a further subject of the present invention to provide means and methods for the genetic treatment of such disorders in the area of molecular medicine using an expression plasmid prepared by incorporating the DNA of this invention downstream from an expression promotor which effects expression in a mammalian host cell.

Growth is one of the fundamental aspects in the development of an organism, regulated by a highly organised and complex system. Height is a multifactorial trait, influenced by both environmental and genetic factors. Developmental malformations concerning body height are common phenomena among humans of all races. With an incidence of 3 in 100, growth retardation resulting in short stature account for the large majority of inborn deficiencies seen in humans.

With an incidence of 1:2500 life-born phenotypic females, Turner syndrome is a common chromosomal disorder (Rosenfeld et al., 1996). It has been estimated that 1-2% of all human conceptions are 45,X and that as many as 99% of such fetuses do not come to term (Hall and Gilchrist, 1990; Robins, 1990). Significant clinical variability exists in the phenotype of persons with Turner syndrome (or Ullrich-Turner syndrome) (Ullrich, 1930; Turner, 1938). Short stature, however, is a consistent finding and together with gonadal dysgenesis considered as the lead symptoms of this disorder. Turner syndrome is a true multifactorial disorder. Both the embryonic lethality, the short stature, gonadal dysgenesis and the characteristic somatic features are thought to be due to monosomy of genes common to the X and Y chromosomes. The diploid dosis of those X-Y homologous genes are suggested to be requested for normal human development. Turner genes (or anti-Turner genes) are expected to be expressed in females from both the active and inactive X chromosomes or Y chromosome to ensure correct dosage of gene product. Haploinsufficiency (deficiency due to only one active copy), consequently would be the suggested genetic mechanism underlying the disease.

A variety of mechanisms underlying short stature have been elucidated so far. Growth hormone and growth hormone receptor deficiencies as well as skeletal disorders have been described as causes for the short stature phenotype (Martial et al., 1979; Phillips et al., 1981; Leung et al., 1987; Goddard et al., 1995). Recently, mutations in three human fibroblast growth factor receptor-encoding genes (FGFR 1-3) were identified as the cause of various skeletal disorders, including the most common form of dwarfism, achondroplasia (Shiang et al., 1994; Rousseau et al., 1994; Muenke and Schell, 1995). A well-known and frequent (1:2500 females) chromosomal disorder, Turner Syndrome (45,X), is also consistently associated with short stature. Taken together, however, all these different known causes account for only a small fraction of all short patients, leaving the vast majority of short stature cases unexplained to date.

The sex chromosomes X and Y are believed to harbor genes influencing height (Ogata and Matsuo, 1993). This could be deduced from genotype-phenotype correlations in patients with sex chromosome abnormalities. Cytogenetic studies have provided evidence that terminal deletions of the short arms of either the X or the Y chromosome consistently lead to short stature in the respective individuals (Zuffardi et al., 1982; Curry et al., 1984). More than 20 chromosomal rearrangements associated with terminal deletions of chromosome Xp and Yp have been reported that localize the gene(s) responsible for short stature to the pseudoautosomal region (PAR1) (Ballabio et al., 1989, Schaefer et al., 1993). This localisation has been narrowed down to the most distal 700 kb of DNA of the PAR1 region, with DXYS15 as the flanking marker (Ogata et al., 1992; 1995).

Mammalian growth regulation is organized as a complex system. It is conceivable that multiple growth promoting genes (proteins) interact with one another in a highly organized way. One of those genes controlling height has tentatively been mapped to the pseudoautosomal region PAR1 (Ballabio et al., 1989), a region known to be freely exchanged between the X and Y chromosomes (for a review see Rappold, 1993). The entire PAR1 region is approximately 2,700 kb.

The critical region for short stature has been defined with deletion patients. Short stature is the consequence when an entire 700 kb region is deleted or when a specific gene within this critical region is present in haploid state, is interrupted or mutated (as is the case with idiotypic short stature or Turner sydrome). The frequency of Turner's syndrome is 1 in 2500 females worldwide; the frequency of this kind of idiopathic short stature can be estimated to be 1 in 4.000-5.000 persons. Turner females and some short stature individuals usually receive an unspecific treatment with growth hormone (GH) for many years to over a decade although it is well known that they have normal GH levels and GH deficiency is not the problem. The treatment of such patients is very expensive (estimated costs approximately 30.000 USD p.a.). Therefore, the problem existed to provide a method and means for distinguishing short stature patients on the one side who have a genetic defect in the respective gene and on the other side patients who do not have any genetic defect in this gene. Patients with a genetic defect in the respective gene—either a complete gene deletion (as in Turner syndrome) or a point mutation (as in idiopathic short stature)—should be susceptible for an alternative treatment without human GH, which now can be devised.

Genotype/phenotype correlations have supported the existence of a growth gene in the proximal part of Yq and in the distal part of Yp. Short stature is also consistently found in individuals with terminal deletions of Xp. Recently, an extensive search for male and female patients with partial monosomies of the pseudoautosomal region has been undertaken. On the basis of genotype-phenotype correlations, a minimal common region of deletion of 700 kb DNA adjacent to the telomere was determined (Ogata et al., 1992; Ogata et al., 1995). The region of interest was shown to lie between genetic markers DXYS20 (3cosPP) and DXYS15 (113D) and all candidate genes for growth control from within the PAR1 region (e.g., the hemopoietic growth factor receptor a; CSF2RA) (Gough et al., 1990) were excluded based on their physical location (Rappold et al., 1992). That is, the genes were within the 700 kb deletion region of the 2.700 kb PAR1 region.

Deletions of the pseudoautosomal region (PAR1) of the sex chromosomes were recently discovered in individuals with short stature and subsequently a minimal common deletion region of 700 kb within PAR1 was defined. Southern blot analysis on DNA of patients AK and SS using different pseudoautosomal markers has identified an Xp terminal deletion of about 700 kb distal to DXYS15 (113D) (Ogata et al, 1992; Ogata et al, 1995).

The gene region corresponding to short stature has been identified as a region of approximately 500 kb, preferably approximately 170 kb in the PAR1 region of the X and Y chromosomes. Three genes in this region have been identified as candidates for the short stature gene. These genes were designated SHOX (also referred to as SHOX93 or HOX93), (SHOX=short stature homeobox-containing gene), pET92 and SHOT (SHOX-like homeobox gene on chromosome three). The gene SHOX which has two separate splicing sites resulting in two variations (SHOX a and b) is of particular importance. In preliminary investigations, essential parts of the nucleotide sequence of the short stature gene could be analysed (SEQ ID No. 8). Respective exons or parts thereof could be predicted and identified (e.g. exon I [G310]; exon II [ET93]; exon IV [G108]; pET92). The obtained sequence information could then be used for designing appropriate primers or nucleotide probes which hybridize to parts of the SHOX gene or fragments thereof. By conventional methods, the SHOX gene can then be isolated. By further analysis of the DNA sequence of the genes responsible for short stature, the nucleotide sequence of exons I-V could be refined (v. FIGS. 1-3). The gene SHOX contains a homeobox sequence (SEQ ID NO: 1) of approximately 180 bp (v. FIG. 2 and FIG. 3), starting from the nucleotide coding for amino acid position 117 (Q) to the nucleotide coding for amino acid position 176 (E), i.e. from CAG (440) to GAG (619). The homeobox sequence is identified as the homeobox-pET93 (SHOX) sequence and two point mutations have been found in individuals with short stature in a German (A1) and a Japanese patient by screening up to date 250 individuals with idiopahtic short stature. Both point mutations were found at the identical position and leading to a protein truncation at amino acid position 195, suggesting that there may exist a hot spot of mutation. Due to the fact that both mutations found, which lead to a protein truncation, are at the identical position, it is possible that a putative hot spot of recombination exisits with exon 4 (GI 08). Exon specific primers can therefore be used as indicated below, e.g. GCA CAG CCA ACC ACC TAG (for) (SEQ ID NO: 17) or TGG AAA GGC ATC ATC CGT AAG (rev) (SEQ ID NO: 18).

The above-mentioned novel homeobox-containing gene, SHOX, which is located within the 170 kb interval, is alternatively spliced generating two proteins with diverse function. Mutation analysis and DNA sequencing were used to demonstrate that short stature can be caused by mutations in SHOX.

The identification and cloning of the short stature critical region according to the present invention was performed as follows: Extensive physical mapping studies on 15 individuals with partial monosomy in the pseudoautosomal region (PAR1) were performed. By correlating the height of those individuals with their deletion breakpoints a short stature (SS) critical region of approximately 700 kb was defined. This region was subsequently cloned as an overlapping cosmid contig using yeast artificial chromosomes (YACs) from PAR 1 (Ried et al., 1996) and by cosmid walking. To search for candidate genes for SS within this interval, a variety of techniques were applied to an approximately 600 kb region between the distal end of cosmid 56G10 and the proximal end of 51D11. Using cDNA selection, exon trapping, and CpG island cloning, the two novel genes were identified.

The position of the short stature critical interval could be refined to a smaller interval of 170 kb of DNA by characterizing three further specific individuals (GA, AT and RY), who were consistently short. To precisely localize the rearrangement breakpoints of those individuals, fluorescence in situ hybridization (FISH) on metaphase chromosomes was carried out using cosmids from the contig. Patient GA, with a terminal deletion and normal height, defined the distal boundary of the critical region (with the breakpoint on cosmid 110E3), and patient AT, with an X chromosome inversion and normal height, the proximal boundary (with the breakpoint on cosmid 34F5). The Y-chromosomal breakpoint of patient RY, with a terminal deletion and short stature, was also found to be contained on cosmid 34F5, suggesting that this region contains sequences predisposing to chromosome rearrangements.

The entire region, bounded by the Xp/Yp telomere, has been cloned as a set of overlapping cosmids. Fluorescence in situ hybridization (FISH) with cosmids from this region was used to study six patients with X chromosomal rearrangements, three with normal height and three with short stature. Genotype-phenotype correlations narrowed down the critical short stature interval to 270 kb of DNA or even less as 170 kb, containing the gene or genes with an important role in human growth. A minimal tiling path of six to eight cosmids bridging this interval is now available for interphase and metaphase FISH providing a valuable tool for diagnostic investigations on patients with idiopathic short stature.

BRIEF DESCRIPTION OF THE DRAWINGS

FIGS. 2 and 3 are the nucleotide and predicted amino acid sequences of SHOXa (SEQ ID NO: 10) and SHOXb (SEQ ID NO:12).

Figure 1:
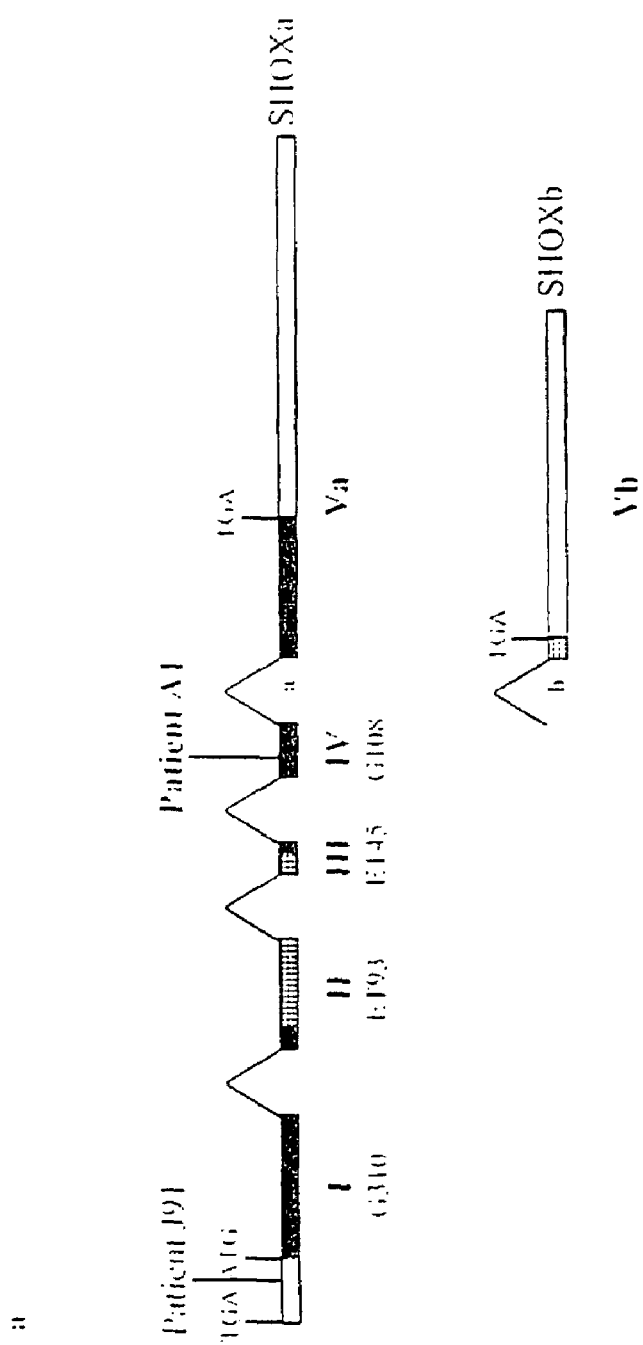
FIG. 1 is a gene map of the SHOX gene including five exons which are identified as follows: exon I: G310, exon II: ET93, exon III: ET45, exon IV: G108 and exons Va and Vb, whereby exons Va and Vb result from two different splicing sites of the SHOX gene. Exon II and III contain the homeobox sequence of 180 nucleotides.

SHOX a: The predicted start of translation begins at nucleotide 92 with the first in-frame stop codon (TGA) at nucleotides 968-970, yielding an open reading frame of 876 bp that encodes a predicted protein of 292 amino acids (designated as transcription factor A or SHOXa protein, respectively). An in-frame, 5'stop codon at nucleotide 4, the start codon and the predicted termination stop codon are in bold. The homeobox is boxed (starting from amino acid position 117 (Q) to 176 (E), i.e. CAG thru GAG in the nucleotide sequence). The locations of introns are indicated with arrows. Two putative polyadenylation signals in the 3'untranslated region are underlined.

SHOX b: An open reading frame of 876 bp exists from A in the first methionin at nucleotide 92 to the in-frame stop codon at nucleotide 767-769, yielding an open reading frame of 675 bp that encodes a predicted protein of 225 amino acids (transcription factor B or SHOXb protein, respectively). The locations of introns are indicated with arrows. Exons I-IV are identical with SHOXa, exon V is specific for SHOX b. A putative polyadenylation signal in the 3' untranslated region is underlined.

FIG. 4 are the nucleotide (SEQ ID NO: 43) and predicted amino acid (SEQ ID NO: 16) sequence of SHOT. The predicted start of translation begins at nucleotide 43 with the first in-frame stop codon (TGA) at nucleotides 613-615, yielding an open reading frame of 573 bp that encodes a predicted protein of 190 amino acids (designated as transcription factor C or SHOT protein, respectively). The homeobox is boxed (starting from amino acid position 11 (Q) to 70 (E), i.e. CAG thru GAG in the nucleotide sequence). The locations of introns are indicated with arrows. Two putative polyadenylation signals in the 3' untranslated region are underlined FIG. 5 gives the exon/intron organization of the human SHOX gene and the respective positions in the nucleotide sequence (Intron/Exon sequences (SEQ ID NOS 44-49, respectively in order of appearance) and Exon/Intron sequences (SEQ ID NOS 50-55, respectively in order of appearance)).

BRIEF DESCRIPTION OF THE SEQ ID

SEQ ID NO. 1: translated amino acid sequence of the homeobox domain (180 bp)
SEQ ID NO. 2: exon II (ET93) of the SHOX gene
SEQ ID NO. 3: exon I (G310) of the SHOX gene
SEQ ID NO. 4: exon III (ET45) of the SHOX gene
SEQ ID NO. 5: exon IV (G108) of the SHOX gene
SEQ ID NO. 6: exon Va of the SHOX gene
SEQ ID NO. 7: exon Vb of the SHOX gene
SEQ ID NO. 8: preliminary nucleotide sequence of the SHOX gene
SEQ ID NO. 9: ET92 gene
SEQ ID NO. 10: SHOXa sequence (see also FIG. 2)
SEQ ID NO. 11: transcription factor A (see also FIG. 2)
SEQ ID NO. 12: SHOXb sequence (see also FIG. 3)
SEQ ID NO. 13: transcription factor B (see also FIG. 3)
SEQ ID NO. 14: SHOX gene
SEQ ID NO: 15: SHOT sequence
SEQ ID NO. 16: transcription factor C (see also FIG. 4)

Since the target gene leading to disorders in human growth (e.g. short stature region) was unknown prior to the present invention, the biological and clinical association of patients with this deletion could give insights to the function of this gene. In the present study, fluorescence in situ hybridization (FISH) was used to examine metaphase and interphase lymphocyte nuclei of six patients. The aim was to test all cosmids of the overlapping set for their utility as FISH probes and to determine the breakpoint regions in all four cases, thereby determining the minimal critical region for the short stature gene.

Duplication and deletion of genomic DNA can be technically assessed by carefully controlled quantitative PCR or dose estimation on Southern blots or by using RFLPs. However, a particularly reliable method for the accurate distinction between single and double dose of markers is FISH, the clinical application of is presently routine. Whereas in interphase FISH, the pure absence or presence of a molecular marker can be evaluated, FISH on metaphase chromosomes may provide a semi-quantitative measurement of inter-cosmid deletions. The present inventor has determined that deletions of about 10 kb (25% of signal reduction) can still be detected. This is of importance, as practically all disease genes on the human X chromosome have been associated with smaller and larger deletions in the range from a few kilobases to several megabases of DNA (Nelson et al., 1995).

Subject of the present invention are therefore DNA sequences or fragments thereof which are part of the genes responsible for human growth (or for short stature, respectively, in case of genetic defects in these genes). Three genes responsible for human growth were identified: SHOX, pET92 and SHOT. DNA sequences or fragments of these genes, as well as the respective full length DNA sequences of these genes can be transformed in an appropriate vector and transfected into cells. When such vectors are introduced into cells in an appropriate way as they are present in healthy humans, it is devisable to treat diseases involved with short stature, i.e. Turners syndrome, by modern means of gene therapy. For example, short stature can be treated by removing the respective mutated growth genes responsible for short stature. It is also possible to stimulate the respective genes which compensate the action of the genes responsible for short stature, i.e. by inserting DNA sequences before, after or within the growth/short stature genes in order to increase the expression of the healthy allels. By such modifications of the genes, the growth/short stature genes become activated or silent, respectively. This can be accomplished by inserting DNA sequences at appropriate sites within or adjacent to the gene, so that these inserted DNA sequences interfere with the growth/short stature genes and thereby activate or prevent their transcription. It is also devisable to insert a regulatory element (e.g. a promotor sequence) before said growth genes to stimulate the genes to become active. It is further devisable to stimulate the respective promotor sequence in order to overexpress—in the case of Turner syndrome—the healthy functional allele and to compensate for the missing allele. The modification of genes can be generally achieved by inserting exogenous DNA sequences into the growth gene/short stature gene via homologous recombination.

The DNA sequences according to the present invention can also be used for transformation of said sequences into animals, such as mammals, via an appropriate vector system. These transgenic animals can then be used for in vivo investigations for screening or identifying pharamceutical agents which are useful in the treatment of diseases involved with short stature. If the animals positively respond to the administration of a candidate compound or agent, such agent or compound or derivatives thereof would be devisable as pharmaceutical agents. By appropriate means, the DNA sequences of the present invention can also be used in genetic experiments aiming at finding methods in order to compensate for the loss of genes responsible for short stature (knock-out animals).

In a further object of this invention, the DNA sequences can also be used to be transformed into cells. These cells can be used for identifying pharmaceutical agents useful for the treatment of diseases involved with short stature, or for screening of such compounds or library of compounds. In an appropriate test system, variations in the phenotype or in the expression pattern of these cells can be determined, thereby allowing the identification of interesting candidate agents in the development of pharmaceutical drugs.

The DNA sequences of the present invention can also be used for the design of appropriate primers which hybridize with segments of the short stature genes or fragments thereof under stringent conditions. Appropriate primer sequences can be constructed which are useful in the diagnosis of people who have a genetic defect causing short stature. In this respect it is noteworthy that the two mutations found occur at the identical position, suggesting that a mutational hot spot exists.

In general, DNA sequences according to the present invention are understood to embrace also such DNA sequences which are degenerate to the specific sequences shown, based on the degeneracy of the genetic code, or which hybridize under stringent conditions with the specifically shown DNA sequences.

The present invention encompasses especially the following aspects:
a) An isolated human nucleic acid molecule encoding polypeptides containing a homeobox domain of sixty amino acids having the amino acid sequence of SEQ ID NO: 1 and having regulating activity on human growth.
b) An isolated DNA molecule comprising the nucleotide sequence essentially as indicated in FIG. 2, FIG. 3 or FIG. 4, and especially as shown in SEQ ID NO: 10, SEQ ID NO: 12 or SEQ ID NO: 15.
c) DNA molecules capable of hybridizing to the DNA molecules of item b).
d) DNA molecules of item c) above which are capable of hybridization with the DNA molecules of item 2. under a temperature of 60-70° C. and in the presence of a standard buffer solution.
e) DNA molecules comprising a nucleotide sequence having a homology of seventy percent or higher with the nucleotide sequence of SEQ ID NO: 10, SEQ ID NO: 12 or SEQ ID NO: 15 and encoding a polypeptide having regulating activity on human growth.
f) Human growth proteins having the amino acid sequence of SEQ ID NO: 11, 13 or 16 or a functional fragment thereof.
g) Antibodies obtained from immunization of animals with human growth proteins of item f) or antigenic variants thereof.
h) Pharmaceutical compositions comprising human growth proteins or functional fragments thereof for treating disorders caused by genetic mutations of the human growth gene.
i) A method of screening for a substance effective for the treatment of disorders mentioned above under item h) comprising detecting messenger RNA hybridizing to any of the DNA molecules described in a)-e) so as to measure any enhancement in the expression levels of the DNA molecule in response to treatment of the host cell with that substance.
j) An expression vector or plasmid containing any of the nucleic acid molecules described in a)-e) above which enables the DNA molecules to be expressed in mammalian cells.
k) A method for the determination of the gene or genes responsible for short stature in a biological sample of body tissues or body fluids.

In the method k) above, preferably nucleotide amplification techniques, e.g. PCR, are used for detecting specific nucleotide sequences known to persons skilled in the art, and described, for example, by Mullis et al. 1986, Cold Spring Harbor Symposium Quant. Biol. 51, 263-273, and Saiki et al., 1988, Science 239, 487-491, which are incorporated herein by reference. The short stature nucleotide sequences to be determined are mainly those represented by sequences SEQ ID No. 2 to SEQ ID No. 7.

In principle, all oligonucleotide primers and probes for amplifying and detecting a genetic defect responsible for diminished human growth in a biological sample are suitable for amplifying a target short stature associated sequence. Especially, suitable exon specific primer pairs according to the invention are provided by table 1. Subsequently, a suitable detection, e.g. a radioactive or non-radioactive label is carried out.

TABLE 1

| Exon | Sense primer | Antisense primer | Product (bp) | Ta (° C.) |
|---|---|---|---|---|
| 5'-I (G310) | SP 1 | ASP 1 | 194 | 58 |
| 3'-I (G310) | SP 2 | ASP 2 | 295 | 58 |
| II (ET93) | SP 3 | ASP 3 | 262 | 76/72/68 |
| III (ET45) | SP 4 | ASP 4 | 120 | 65 |
| IV (G108) | SP 5 | ASP 5 | 154 | 62 |
| Va (SHOXa) | SP 6 | ASP 6 | 265 | 61 | explanation of the abbreviations for the primers:

```
SP 1:    ATTTCCAATGGAAAGGCGTAAATAAC
         (SEQ ID NO.19)

SP2:     ACGGCTTTTGTATCCAAGTCTTTTG
         (SEQ ID NO.20)

SP3:     GCCCTGTGCCCTCCGCTCCC
         (SEQ ID NO.21)

SP4:     GGCTCTTCACATCTCTCTCTGCTTC
         (SEQ ID NO.22)

SP5:     CCACACTGACACCTGCTCCCTTTG
         (SEQ ID NO.23)

SP6:     CCCGCAGGTCCAGGCTCAGCTG
         (SEQ ID NO.24)

ASP1:    CGCCTCCGCCGTTACCGTCCTTG
         (SEQ ID NO.25)

ASP 2:   CCCTGGAGCCGGCGCGCAAAG
         (SEQ ID NO.26)

ASP 3:   CCCCGCCCCCGCCCCCGG
         (SEQ ID NO.27)

ASP 4:   CTTCAGGTCCCCCCAGTCCCG
         (SEQ ID NO.28)

ASP 5:   CTAGGGATCTTCAGAGGAAGAAAAAG
         (SEQ ID NO.29)

ASP 6:   GCTGCGCGGCGGGTCAGAGCCCCAG
         (SEQ ID NO.30)
```

Also, a single stranded RNA can be used as target. Methods for reversed transcribing RNA into cDNA are also well known and described in Sambrook et al., Molecular Cloning: A Laboratory Manual, New York, Cold Spring Harbor Laboratory 1989. Alternatively, preferred methods for reversed transcription utilize thermostable DNA polymerases having RT activity.

Further, the technique described before can be used for selecting those person from a group of persons being of short stature characterized by a genetic defect and which allows as a consequence a more specific medical treatment.

In another subject of the present invention, the transcription factors A, B and C can be used as pharmaceutical agents. These transcription factors initiate a still unknown cascade of biological effects on a molecular level involved with human growth. These proteins or functional fragments thereof have a mitogenic effect on various cells. Especially, they have an osteogenic effect. They can be used in the treatment of bone diseases, such as e.g. osteoporosis, and especially all those diseases involved with disturbance in the bone calcium regulation.

As used herein, the term "isolated" refers to the original derivation of the DNA molecule by cloning. It is to be understood however, that this term is not intended to be so limiting and, in fact, the present invention relates to both naturally occurring and synthetically prepared sequences, as will be understood by the skilled person in the art.

The DNA molecules of this invention may be used in forms of gene therapy involving the use of an expression plasmid prepared by incorporating an appropriate DNA sequence of this invention downstream from an expression promotor that effects expression in a mammalian host cell. Suitable host cells are procaryotic or eucaryotic cells. Procaryotic host cells are, for example, E. coli, Bacillus subtilis, and the like. By transfecting host cells with replicons originating from species adaptable to the host, that is, plasmid vectors containing replication starting point and regulator sequences, these host cells can be transfected with the desired gene or cDNA. Such vectors are preferably those having a sequence that provides the transfected cells with a property (phenotype) by which they can be selected. For example, for E. coli hosts the strain E. coli K12 is typically used, and for the vector either pBR322 or pUC plasmids can be generally employed. Examples for suitable promotors for E. coli hosts are trp promotor, lac promotor or lpp promotor. If desired, secretion of the expression product through the cell membrane can be effected by connecting a DNA sequence coding for a signal peptide sequence at the 5' upstream side of the gene. Eucaryotic host cells include cells derived from vertebrates or yeast etc. As a vertebrate host cell, COS cells can be used (Cell, 1981, 23: 175-182), or CHO cells. Preferably, promotors can be used which are positioned 5' upstream of the gene to be expressed and having RNA splicing positions, polyadenylation and transcription termination seqences.

The transcription factors A, B and C of the present invention can be used to treat disorders caused by mutations in the human growth genes and can be used as growth promoting agents. Due to the polymorphism known in the case of eukaryotic genes, one or more amino acids may be substituted. Also, one or more amino acids in the polypeptides can be deleted or inserted at one or more sites in the amino acid sequence of the polypeptides of SEQ ID NO: 11, 13 or 16. Such polypeptides are generally referred to equivalent polypeptides as long as the underlying biological acitivity of the unmodified polypeptide remains essentially unchanged.

The present invention is illustrated by the following examples.

EXAMPLE 1

Patients

All six patients studied had de novo sex chromosome aberrations.

CC is a girl with a karyotype 45,X/46,X psu dic (X) (Xqter→Xp22.3::Xp22.3→Xqter). At the last examination at 6½ years of age, her height was 114 cm (25-50 the % percentile). Her mother's height was 155 cm, the father was not available for analysis. For details, see Henke et al., 1991.

GA is a girl with a karyotype 46,X der X (3pter→3p23::Xp22.3→Xqter). At the last examination at 17 years, normal stature (159 cm) was observed. Her mother's height is 160 cm and her father's height 182 cm. For details, see Kulharya et al, 1995.

SS is a girl with a karyotype 46,X rea (X) (Xqter→Xq26::Xp22.3→Xq26:). At 11 years her height remained below the 3rd percentile growth curve for Japanese girls; her predicted adult height (148.5 cm) was below her target height (163 cm) and target range (155 to 191 em). For details, see Ogata et alt, 1992.

AK is a girl with a karyotype 46,X rea (X) (Xqter→Xp22.3::Xp22.3→Xp21.3:). At 13 years her height remained below the 2nd percentile growth curve for Japanese girls; her predicted adult height (142.8 cm) was below her target height (155.5 cm) and target range (147.5-163.5 em). For details, see Ogata et alt, 1995.

RY: the karyotype of the ring Y patient is 46,X,r(Y)/46, Xdic r(Y)/45,X[95:3:2], as examined on 100 lymphocytes; at 16 years of age his final height was 148; the heights of his three brothers are all in the normal range with 170 cm (16 years, brother 1), 164 cm (14 years, brother 2) and 128 cm (9 years, brother 3), respectively. Growth retardation of this patient is so severe that it would also be compatible with an additional deletion of the GCY locus on Yq.

AT: boy with ataxia and inv(X); normal height of 116 cm at age 7, parents' heights are 156 cm and 190 cm, respectively.

Patients for Mutation Analysis:

250 individuals with idiopathic short stature were tested for mutations in SHOXa. The patients were selected on the following criteria: height for chronological age was below the 3rd centile of national height standards, minus 2 standard deviations (SDS); no causative disease was known, in particular: normal weight (length) for gestational age, normal body proportions, no chronic organic disorder, normal food intake, no psychiatric disorder, no skeletal dysplasia disorder, no thyroid or growth hormone deficiency.

Family A:

Cases 1 and 2 are short statured children of a German non-consanguineous family. The boy (case 1) was born at the 38th week of gestation by cesarian section. Birth weight was 2660 g, birth length 47 cm. He developed normally except for subnormal growth. On examination at the age of 6.4 years, he was proportionate small (106.8 cm, −2.6 SDS) and obese (22.7 kg), but otherwise normal. His bone age was not retarded (6 yrs) and bone dysplasia was excluded by X-ray analysis. IGF-I and IGFBP-3 levels as well as thyroid parameters in serum rendered GH or thyroid hormone deficiency unlikely. The girl (case 2) was born at term by cesarian section. Birth weight was 2920 g, birth length 47 cm. Her developmental milestones were normal, but by the age of 12 months poor growth was apparent (length: 67 cm, −3.0 SDS). At 4 years she was 89.6 cm of height (−3.6 SDS). No dysmorphic features or dysproportions were apparent. She was not obese (13 kg). Her bone age was 3.5 years and bone dysplasia was excluded. Hormone parameters were normal. It is interesting to note that both the girl and the boy grow on the 50 percentile growth curve for females with Turner syndrome. The mother is the smallest of the family and has a mild rhizomelic dysproportion (142.3 cm, −3.8 SDS). One of her two sisters (150 cm, −2.5 SDS) and the maternal grandmother (153 cm, −2.0 SDS) are all short without any dysproportion. One sister has normal stature (167 cm, +0.4 SDS). The father's height is 166 cm (−1.8 SDS) and the maternal grandfather' height is 165 cm (−1.9 SDS). The other patient was of Japanese origin and showed the identical mutation.

EXAMPLE 2

Identification of the Short Stature Gene

A. In Situ Hybridization a) Florescence In Situ Hybridization (FISH)

Florescence in situ hybridization (FISH) using cosmids residing in the Xp/Yp pseudoautosomal region (PAR1) was carried out. FISH studies using cosmids 64/75cos (LLNLc110H032), E22cos (2e2), F1/14cos (110A7), M1/70cos (110E3), P99F2cos (43C11), P99cos (LLNLc110P2410), B6cosb (1CRFc104H0425), F20cos (34F5), F21cos (ICRFc104G0411), F3cos2 (9E3), F3cos1 (11E6), P117cos (29B11), P6cos1 (ICRFc104P0117), P6cos2 (LLNLc110E0625) and E4cos (15G7) was carried out according to published methods (Lichter and Cremer, 1992). In short, one microgram of the respective cosmid clone was labeled with biotin and hybridized to human metaphase chromosomes under conditions that suppress signals from repetitive DNA sequences. Detection of the hybridization signal was via FITC-conjugated avidin. Images of FITC were taken by using a cooled charge coupled device camera system (Photometrics, Tucson, Ariz.).

b) Physical Mapping

Cosmids were derived from Lawrence Livermore National Laboratory X- and Y-chromosome libraries and the Imperial Cancer Research Fund London (now Max Planck Institute for Molecular Genetics Berlin) X chromosome library. Using cosmids distal to DXYS15, namely E4cos, P6cos2, P6cos1, P117cos and F3cos1 one can determine that two copies are still present of E4cos, P6cos2, P6cos1 and one copy of P117cos and F3cos1. Breakpoints of both patients AK and SS map on cosmid P6cos1, with a maximum physical distance of 10 kb from each other. It was concluded that the abnormal X chromosomes of AK and SS have deleted about 630 kb of DNA.

Further cosmids were derived from the ICRF X chromosome specific cosmid library (ICRFc104), the Lawrence Livermore X chromosome specific cosmid library (LLNLc110) and the Y chromosome specific library (LLCO3'M'), as well as from a self-made cosmid library covering the entire genome. Cosmids were identified by hybridisation with all known probes mapping to this region and by using entire YACs as probes. To verify overlaps, end probes from several cosmids were used in cases in which overlaps could not be proven using known probes.

c) Southern Blot Hybridisation

Southern blot analysis using different pseudoautosomal markers has provided evidence that the breakpoint on the X chromosome of patient CC resides between DXYS20 (3cosPP) and DXYS60 (U7A) (Henke et al, 1991). In order to confirm this finding and to refine the breakpoint location, cosmids 64/75cos, E22cos, F1/14cos, M1/70cos, F2cos, P99F2cos and P99cos were used as FISH probes. The breakpoint location on the abnormal X of patient CC between cosmids 64/75cos (one copy) and F1/14cos (two copies) on the E22PAC could be determined. Patient CC with normal stature consequently has lost approximately 260-290 kb of DNA.

Southern blot hybridisations were carried out at high stringency conditions in Church buffer (0.5 M NaPi pH 7.2, 7% SDS, 1 mM EDTA) at 65° C. and washed in 40 mM NaPi, 1% SDS at 65° C.

d) FISH Analysis

Biotinylated cosmid DNA (insert size 32-45 kb) or cosmid fragments (10-16 kb) were hybridised to metaphase chromosomes from stimulated lymphocytes of patients under conditions as described previously (Lichter and Cremer, 1992). The hybridised probe was detected via avidin-conjugated FITC.

e) PCR Amplification

All PCRs were performed in 50 µl volumes containing 100 pg-200 ng template, 20 pmol of each primer, 200 µM dNTP's (Pharmacia), 1.5 mM $MgCl_2$, 75 mMTris/HCl pH9, 20 mM $(NH_4)_2SO_4$ 0.01% (w/v) Tween20 and 2 U of Goldstar DNA Polymerase (Eurogentec). Thermal cycling was carried out in a Thermocycler GeneE (Techne).

f) Exon Amplification

Four cosmid pools consisting of each four to five clones from the cosmid contigs were used for exon amplification experiments. The cosmids in each cosmid pool were partially digested with Sau3A. Gel purified fractions in the size range of 4-10 kb were cloned in the BamHI digested pSPL3B vector (Burn et al, 1995) and used for the exon amplification experiments as previously described (Church et al., 1994).

g) Genomic Sequencing

Sonificated fragments of the two cosmids LLOYNCO3'M'15D10 and LLOYNCO3'M'34F5 were subcloned separately into M13 mp18 vectors. From each cosmid library at least 1000 plaques were picked, M13 DNA prepared and sequenced using dye-terminators, ThermoSequenase (Amersham) and universal M13-primer (MWG-BioTech). The gels were run on ABI-377 sequencers and data were assembled and edited with the GAP4 program (Staden).

Of all six patients, GA had the least well characterized chromosomal breakpoint. The most distal markers previously tested for their presence or absence on the X were DXS1060 and DXS996, which map approximately 6 Mb from the telomere (Nelson et al., 1995). Several cosmids containing different gene sequences from within PAR1 (MIC2, ANT3, CSF2RA, and XE7) were tested and all were present on the translocation chromosome. Cosmids from within the short stature critical region e.g., chromosome, thereby placing the translocation breakpoint on cosmid M1/70cos. A quantitative comparison of the signal intensities of M1/70cos between the normal and the rearranged X indicates that approximately 70% of this cosmid is deleted.

TABLE 2

|  | CC | GA | AK | SS |
|---|---|---|---|---|
| 64/75cos | − | − |  |  |
| E22cos | − | − |  |  |
| F1/14cos | + | − |  |  |
| M1/70cos | + | (+) |  |  |
| F2cos | + | + |  |  |
| P99F2cos | + | + |  |  |
| P99cos | + | + |  |  |
| B6cos |  | + |  |  |
| F20cos |  |  |  |  |
| F21cos |  |  |  |  |
| F3cos2 |  |  |  |  |
| F3cos1 |  |  | − | − |
| P117cos |  |  | − | − |
| P6cos1 |  |  | + | + |
| P6cos2 |  |  | + | + |
| E4cos |  |  | + | + |

Table 2: This table summarizes the FISH data for the 16 cosmids tested on four patients.

[−] one copy; indicates that the respective cosmid was deleted on the rearranged X, but present on the normal X chromosome

[+] two copies; indicates that the respective cosmid is present on the rearranged and on the normal X chromosome

[(+)] breakpoint region; indicates that the breakpoint occurs within the cosmid as shown by FISH In summary, the molecular analysis on six patients with X chromosomal rearrangements using florescence-labeled cosmid probes and in situ hybridization indicates that the short stature critical region can be narrowed down to a 270 kb interval, bounded by the breakpoint of patient GA from its centromere distal side and by patients AK and SS on its centromere proximal side.

Genotype-phenotype correlations may be informative and have been chosen to delineate the short stature critical interval on the human X and Y chromosome. In the present study FISH analysis was used to study metaphase spreads and interphase nuclei of lymphocytes from patients carrying deletions and translocations on the X chromosome and breakpoints within Xp22.3. These breakpoints appear to be clustered in two of the four patients (AK and SS) presumably due to the presence of sequences predisposing to chromosome rearrangements. One additional patient Ring Y has been found with an interruption in the 270 kb critical region, thereby reducing the critical interval to a 170 kb region.

By correlating the height of all six individuals with their deletion breakpoint, an interval of 170 kb was mapped to within the pseudoautosomal region, presence or absence of which has a significant effect on stature. This interval is bounded by the X chromosomal breakpoint of patient GA at 340 kb from the telomere (Xptel) distally and by the breakpoints of patients AT and RY at 510/520 kb Xptel proximally. This assignment constitutes a considerable reduction of the critical interval to almost one fourth of its previous size (Ogata et al., 1992; Ogata et al., 1995). A small set of six to eight cosmids are now available for FISH experiments to test for the prevalence and significance of this genomic locus on a large series of patients with idiopathic short stature.

B. Identification of the Candidate Short Stature Gene

To search for transcription units within the smallest 170 kb critical region, exon trapping and cDNA selection on six cosmids (110E3, F2cos, 43C11, P2410, 15D10, 34F5) was carried out. Three different positive clones (ET93, ET45 and G108) were isolated by exon trapping, all of which mapped back to cosmid 34F5. Previous studies using cDNA selection protocols and an excess of 25 different cDNA libraries had proven unsuccessful, suggesting that genes in this interval are expressed at very low abundancy.

To find out whether any gene in this interval was missed, the nucleotide sequence of about 140 kb from this region of the PAR1 was determined, using the random M13 method and dye terminator chemistry. The cosmids for sequence analysis were chosen to minimally overlap with each other and to collectively span the critical interval. DNA sequence analysis and subsequent protein prediction by the "X Grail" program, version 1.3c as well as by the exon-trapping program FEXHB were carried out and confirmed all 3 previously cloned exons. No protein-coding genes other than the previously isolated one could be detected.

C. Isolation of the Short Stature Candidate Gene SHOX

Assuming that all three exon clones ET93, ET45 and G108 are part of the same gene, they were used collectively as probes to screen 14 different cDNA libraries from 12 different fetal (lung, liver, brain 1 and 2) and adult tissues (ovary, placenta 1 and 2, fibroblast, skeletal muscle, bone marrow, brain, brain stem, hypothalamus, pituitary). Not a single clone among approximately 14 million plated clones was detected. To isolate the full-length transcript, 3' and 5'RACE were carried out. For 3'RACE, primers from exon G108 were used on RNA from placenta, skeletal muscle and bone marrow fibroblasts, tissues where G108 was shown to be expressed in. Two different 3'RACE clones of 1173 and 652 bp were derived from all three tissues, suggesting that two different 3'exons a and b exist. The two different forms were termed SHOXa and SHOXb.

To increase chances to isolate the complete 5'portion of a gene known to be expressed at low abundancy, a Hela cell line was treated with retinoic acid and phorbol ester PMA. RNA from such an induced cell line and RNA from placenta and skeletal muscle were used for the construction of a 'Marathon cDNA library'. Identical 5'RACE cDNA clones were isolated from all three tissues.

Experimental Procedure:

RT-PCR and cDNA Library Construction

Human polyA+RNA of heart, pancreas, placenta, skeletal muscle, fetal kidney and liver was purchased from Clontech. Total RNA was isolated from a bone marrow fibroblast cell line with TRIZOL reagent (Gibco-BRL) as described by the manufacturer. First strand cDNA synthesis was performed with the Superscript first strand cDNA synthesis kit (Gibco-BRL) starting with 100 ng polyA+RNA or 10 µg total RNA using oligo(dt)-adapter primer (GGCCACGCGTCGAC-TAGTAC[dT]$_{20}$N (SEQ ID NO.31). After first strand cDNA synthesis the reaction mix was diluted 1/10. For further PCR experiments 5 µl of this dilutions were used.

A 'Marathon cDNA library' was constructed from skeletal muscle and placenta polyA+RNA with the marathon cDNA amplification kit (Clontech) as described by the manufacturer.

Fetal brain (catalog #HL5015b), fetal lung (HL3022a), ovary (HL1098a), pituitary gland (HL1097v) and hypothalamus (HL1172b) cDNA libraries were purchased from Clontech. Brain, kidney, liver and lung cDNA libraries were part of the quick screen human cDNA library panel (Clontech). Fetal muscle cDNA library was obtained from the UK Human Genome Mapping Project Resource Center.

D. Sequence Analysis and Structure of SHOX Gene

A consensus sequence of SHOXa and SHOXb (1349 and 1870 bp) was assembled by analysis of sequences from the 5' and 3'RACE derived clones. A single open reading frame of 1870 bp (SHOXa) and 1349 bp (SHOXb) was identified, resulting in two proteins of 292 (SHOXa) and 225 amino acids (SHOXb). Both transcripts a and b share a common 5'end, but have a different last 3'exon, a finding suggestive of the use of alternative splicing signals. A complete alignment between the two cDNAs and the sequenced genomic DNA from cosmids LL0YNCO3"M"15D10 and LL0YNC3"M"34F5 was achieved, allowing establishment of the exon-intron structure (FIG. 4). The gene is composed of 6 exons ranging in size from 58 bp (exon III) to 1146 bp (exon Va). Exon I contains a CpG-island, the start codon and the 5' region. A stop codon as well as the 3'-noncoding region is located in each of the alternatively spliced exons Va and Vb.

EXAMPLE 3

Two cDNAs have been identified which map to the 160 kb region identified as critical for short stature. These cDNAs correspond to the genes SHOX and pET92. The cDNAs were identified by the hybridization of subclones of the cosmids to cDNA libraries. Employing the set of cosmid clones with complete coverage of the critical region has now provided the genetic material to identify the causative gene. Positional cloning projects aimed at the isolation of the genes from this region are done by exon trapping and cDNA selection techniques. By virtue of their location within the pseudoautosomal region, these genes can be assumed to escape X-inactivation and to exert a dosage effect.

The cloning of the gene leading to short stature when absent (haploid) or deficient, represents a further step forward in diagnostic accuracy, providing the basis for mutational analysis within the gene by e.g. single strand conformation polymorphism (SSCP). In addition, cloning of this gene and its subsequent biochemical characterization has opened the way to a deeper understanding of biological processes involved in growth control.

The DNA sequences of the present invention provide a first molecular test to identify individuals with a specific genetic disorder within the complex heterogeneous group of patients with idiopathic short stature.

EXAMPLE 4

Expression Pattern of SHOXa and SHOXb

Northern blot analysis using single exons as hybridisation probes reveiled a different expression profile for every exon, strongly suggesting that the bands of different size and intensities represent cross-hybridisation products to other G,C rich gene sequences. To achieve a more realistic expression profile of both genes SHOXa and b, RT-PCR experiments on RNA from different tissues were carried out. Whereas expression of SHOXa was observed in skeletal muscle, placenta, pancreas, heart and bone marrow fibroblasts, expression of SHOXb was restricted to fetal kidney, skeletal muscle and bone marrow fibroblasts, with the far highest expression in bone marrow fibroblasts.

The expression of SHOXa in several cDNA libraries made of fetal brain, lung and muscle, of adult brain, lung and pituitary and of SHOXb in none of the tested libraries gives additional evidence that one spliced form (SHOXa) is more broadly expressed and the other (SHOXb) expressed in a predominantly tissue-specific manner.

To assess the transcriptional activity of SHOXa and SHOXb on the X and Y chromosome we used RT-PCR of RNA extracted from various cell lines containing the active X, the inactive X or the Y chromosome as the only human chromosomes. All cell lines revealed an amplification product of the expected length of 119 bp (SHOXa) and 541 bp (SHOXb), providing clear evidence that both SHOXa and b escape X-inactivation.

SHOXa and SHOXb encode novel homeodomain proteins. SHOX is highly conserved across species from mammalian to fish and flies. The very 5' end and the very 3' end—besides the homeodomain—are likely conserved regions between man and mouse, indicating a functional significance. Differences in those amino acid regions have not been allowed to accumulate during evolution between man and mouse.

Experimental Procedures:

a) 5' and 3'RACE

To clone the 5' end of the SHOXa and b transcripts, 5'RACE was performed using the constructed 'Marathon cDNA libraries'. The following oligonucleotide primers were used: SHOX B rev, GAAAGGCATCCGTAAG-GCTCCC (position 697-718 (SEQ ID NO.32)), reverse strand [r]) and the adaptor primer API. PCR was carried out using touchdown parameters: 94° C. for 2 min, 94° C. for 30 sec, 70° C. for 30 sec, 72° C. for 2 min for 5 cycles. 94° C. for 30 sec, 66° C. for 30 sec, 72° C. for 2 min for 5 cycles. 94° C. for 30 sec, 62° C. for 30 sec, 72° C. for 2 min for 25 cycles. A second round of amplification was performed using $\frac{1}{100}$ of the PCR product and the following nested oligonucleotide primers: SHOX A rev, GACGCCTTTATG-CATCTGATTCTC (position 617-640 r (SEQ ID NO.33)) and the adaptor primer AP2. PCR was carried out for 35 cycles with an annealing temperature of 60° C.

To clone the 3' end of the SHOXa and b transcripts, 3'RACE was performed as previously described (Frohman et al., 1988) using oligo(dT)adaptor primed first strand cDNA. The following oligonucleotide primers were used: SHOX A for, GAATCAGATGCATAAAGGCGTC (position 619-640 (SEQ ID NO. 34)) and the oligo(dT)adaptor. PCR was carried out using following parameters: 94° C. for 2 min, 94° C. for 30 sec, 62° C. for 30 sec, 72° C. for 2 min for 35 cycles. A second round of amplification was performed using $\frac{1}{100}$ of the PCR product and the following nested oligonucleotide primers: SHOX B for, GGGAGC-CTTACGGATGCCTTTC (position 697-718 (SEQ ID NO. 35)) and the oligo(dT)adaptor. PCR was carried out for 35 cycles with annealing temperature of 62° C.

To validate the sequences of SHOXa and SHOXb transcripts, PCR was performed with a 5' oligonucleotide primer and a 3' oligonucleotide primer. For SHOXa the following primers were used: G310 for, AGCCCCGGCTGCTCGC-CAGC (position 59-78 (SEQ ID NO. 36)) and SHOX D rev, CTGCGCGGCGGGTCAGAGCCCCAG (position 959-982 r (SEQ ID NO. 37)). For SHOXb the following primers were used: G310 for, AGCCCCGGCTGCTCGCCAGC and SHOX2A rev (SEQ ID NO. 38), GCCTCAGCAGCAAAG-CAAGATCCC (position 1215-1238 r (SEQ ID NO. 39)). Both PCRs were carried out using touchdown parameters: 94° C. for 2 min, 94° C. for 30 sec, 70° C. for 30 sec, 72° C. for 2 min for 5 cycles. 94° C. for 30 sec, 68° C. for 30 sec, 72° C. for 2 min for 5 cycles. 94° C. for 30 sec, 65° C. for 30 sec, 72° C. for 2 min for 35 cycles. Products were gel-purified and cloned for sequencing analysis.

b) SSCP Analysis

SSCP analysis was performed on genomic amplified DNA from patients according to a previously described method (Orita et al., 1989). One to five µl of the PCR products were mixed with 5 µl of denaturation solution containing 95% Formamid and 10 mM EDTA pH8 and denaturated at 95° C. for 10 min. Samples were immediately chilled on ice and loaded on a 10% Polyacryamidgel (Acrylamide:Bisacryamide=37.5:1 and 29:1; Multislotgel, TGGE base, Qiagen) containing 2% glycerol and 1×TBE. Gels were run at 15° C. with 500V for 3 to 5 hours and silver stained as described in TGGE handbook (Qiagen, 1993).

c) Cloning and Sequencing of PCR Products

PCR products were cloned into pMOSBlue using the pMOSBlueT-Vector Kit from Amersham. Overnight cultures of single colonies were lysed in 100 µl $H_2O$ by boiling for 10 min. The lysates were used as templates for PCRs with specific primers for the cloned PCR product. SSCP of PCR products allowed the identification of clones containing different alleles. The clones were sequenced with CY5 labelled vector primers Uni and T7 by the cycle sequencing method described by the manufacturer (ThermoSequenase Kit (Amersham)) on an ALF express automated sequencer (Pharmacia).

d) PCR Screening of cDNA Libraries

To detect expression of SHOXa and b, a PCR screening of several cDNA libraries and first strand cDNAs was carried out with SHOXa and b specific primers. For the EDNA libraries a DNA equivalent of $5 \times 10^8$ pfu was used.

For SHOXa, primers SHOX E rev, GCTGAGCCTGGAC-CTGTTGGAAAGG (position 713-737 r (SEQ ID NO.40)) and SHOX a for were used. For SHOXb, the following primers were used: SHOX B for and SHOX2A rev. Both PCRs were carried out using touchdown parameters: 94° C. for 2 min; 94° C. for 30 sec, 68° C. for 30 sec, 72° C. for 40 sec for 5 cycles. 94° C. for 30 sec, 65° C. for 30 sec, 72° C. for 40 sec for 5 cycles. 94° C. for 30 sec, 62° C. for 30 sec, 72° C. for 40 seq for 35 cycles.

e) PCR Screening of cDNA Libraries

To detect expression of SHOXa and b, a PCR screening of several cDNA libraries and first strand cDNAs was carried out with SHOXa and b specific primers. For the cDNA libraries a DNA equivalent of $5 \times 10^8$ pfu was used. For SHOXa, primers SHOX E rev, GCTGAGCCTGGAC-CTGTTGGAAAGG (position 713-737 r (SEQ ID NO.41)) and SHOX a for were used. For SHOXb, the following primers were used: SHOX B for and SHOX2A rev. Both PCRs were carried out using touchdown parameters: 94° C. for 2 min; 94° C. for 30 sec, 68° C. for 30 sec, 72° C. for 40 sec for 5 cycles. 94° C. for 30 sec, 65° C. for 30 sec, 72° C. for 40 sec for 5 cycles. 94° C. for 30 sec, 62° C. for 30 sec, 72° C. for 40 sec for 35 cycles.

EXAMPLE 5

Expression Pattern of OG12, the Putative Mouse Homolog of Both SHOX and SHOT

In situ hybridisation on mouse embryos ranging from day 5 p.c. and day 18,5 p.c., as well as on fetal and newborn animals was carried out to establish the expression pattern. Expression was seen in the developing limb buds, in the mesoderm of nasal processes which contribute to the formation of the nose and palate, in the eyelid, in the aorta, in the developing female gonads, in the developing spinal cord (restricted to differentiating motor neurons) and brain. Based on this expression pattern and on the mapping position of its human homolog SHOT, SHOT represents a likely candidate for the Comelia de_Lange syndrome which includes short stature.

EXAMPLE 6

Isolation of a Novel SHOX-Like Homeobox Gene on Chromosome Three, Shot, being Related to Human Growth/Short Stature A new gene called SHOT (for SHOX-homolog on chromosome three) was isolated in human, sharing the most homology with the murine OG12 gene and the human SHOX gene. The human SHOT gene and the murine OG12 genes are highly homologous, with 99% identity at the protein level. Although not yet proven, due to the striking homology between SHOT and SHOX (identity within the homeodomain only), it is likely that SHOT is also a gene likely involved in short stature or human growth.

SHOT was isolated using primers from two new human ESTs (HS 1224703 and HS 126759) from the EMBL database, to amplify a reverse-transcribed RNA from a bone marrow fibroblast line (Rao et al, 1997). The 5' and 3' ends of SHOT were generated by RACE-PCR from a bone marrow fibroblast library that was constructed according to Rao et al., 1997. SHOT was mapped by FISH analysis to chromosome 3q25/q26 and the murine homolog to the syntenic region on mouse chromosome 3. Based on the expression pattern of OG12, its mouse homolog, SHOT represents a candidate for the Cornelia Lange syndrome (which shows short stature and other features, including craniofacial abnormalities) mapped to this chromosomal interval on 3q25/26.

EXAMPLE 7

Searching for Mutations in Patients with Idiopathic Short Stature

The DNA sequences of the present invention are used in PCR, LCR, and other known technologies to determine if such individuals with short stature have small deletions or point mutations in the short stature gene.

A total of initially 91 (in total 250 individuals) unrelated male and female patients with idiopathic short stature (idiopathic short stature has an estimated incidence of 2-2,5% in the general population) were tested for small rearrangements or point mutations in the SHOXa gene. Six sets of PCR primers were designed not only to amplify single exons but also sequences flanking the exon and a small part of the 5'UTR. For the largest exon, exon one, two additional internal-exon primers were generated. Primers used for PCR are shown in table 2.

Single strand conformation polymorphism (SSCP) of all amplified exons ranging from 120 to 295 bp in size was carried out. Band mobility shifts were identified in only 2 individuals with short stature (Y91 and A1). Fragments that gave altered SSCP patterns (unique SSCP conformers) were cloned and sequenced. To avoid PCR and sequencing artifacts, sequencing was performed on two strands using two independent PCR reactions. The mutation in patient Y91 resides 28 bp 5'of the start codon in the 5'UTR and involves a cytidine-to-guanine substitution. To find out if this mutation represents a rare polymorphism or is responsible for the phenotype by regulating gene expression e.g. though a weaker binding of translation initiation factors, his parents and a sister were tested. As both the sister and father with normal height also show the same SSCP variant (data not shown), this base substitution represents a rare polymorphism unrelated to the phenotype.

Cloning and sequencing of a unique SSCP conformer for patient A1 revealed a cytidine-to-thymidine base transition (nucleotide 674) which introduces a termination codon at amino-acid position 195 of the predicted 225 and 292 amino-acid sequences, respectively. To determine whether this nonsense mutation is genetically associated with the short stature in the family, pedigree analysis was carried out. It was found that all six short individuals (defined as height below 2 standard deviations) showed an aberrant SSCP shift and the cytidine-to-thymidine transition. Neither the father, nor one aunt and maternal grandfather with normal height showed this mutation, indicating that the grandmother has transferred the mutated allele onto two of her daughters and her two grandchildren. Thus, there is concordance between the presence of the mutant allele and the short stature phenotype in this family.

The identical situation as indicated above was found in another short stature patient of Japanese origin.

EXAMPLE 8

The DNA sequences of the present invention are used to characterize the function of the gene or genes. The DNA sequences can be used as search queries for data base searching of nucleic acid or amino acid databases to identify related genes or gene products. The partial amino acid sequence of SHOX93 has been used as a search query of amino acid databases. The search showed very high homology to many known homeobox proteins. The cDNA sequences of the present invention can be used to recombinantly produce the peptide. Various expression systems known to those skilled in the art can be used for recombinant protein production.

By conventional peptide synthesis (protein synthesis according to the Merrifield method), a peptide having the sequence CSKSFDQKSKDGNGG (SEQ ID NO: 42) was synthesized and polyclonal antibodies were derived in both rabbits and chicken according to standard protocols.

REFERENCES

The following references are herein incorporated by reference.

Ashworth A, Rastan S, Lovell-Badge R, Kay G (1991): X-chromosome inactivation may explain the difference in viability of X0 humans and mice. Nature 351: 406-408.

Ballabio A, Bardoni A, Carrozzo R, Andria G, Bick D, Campbell L, Hamel B, Ferguson-Smith M A, Gimelli G, Fraccaro M, Maraschio P, Zuffardi O, Guilo S, Camerino G (1989): Contiguous gene syndromes due to deletions in the distal short arm of the human X chromosome. Proc Natl Acad Sci USA 86:10001-10005.

Blagowidow N, Page D C, Huff D, Mennuti M T (1989): Ullrich-Turner syndrome in an XY female fetus with deletion of the sex-determining portion of the Y chromosome. Am. J. med. Genet. 34:159-162.

Cantrell M A, Bicknell J N, Pagon R A et al. (1989): Molecular analysis of 46,XY females and regional assignment of a new Y-chromosome-specific probe. Hum. Genet. 83: 88-92.

Connor J M, Loughlin S A R (1989): Molecular genetics of Turner's syndrome. Acta Pediatr. Scand. (Suppl.) 356: 77-80.

Disteche C M, Casanova M, Saal H, Friedmen C, Sybert V, Graham J, Thuline H, Page D C, Fellous M (1986): Small deletions of the short arm of the Y-chromosome in 46,XY females. Proc Natl Acad Sci USA 83:7841-7844.

Ferguson-Smith M A (1965): Karyotype-phenotype correlations in gonadal dysgenesis and their bearing on the pathogenesis of malformations. J. med. Genet. 2: 142-155.

Ferrari D, Kosher R A, Dealy C N (1994): Limb mesenchymal cells inhibited from undergoing cartilage differentiation by a tumor promoting phorbol ester maintain expression of the homeobox-containing gene MSX1 and fail to exhibit gap junctional communication. Biochemical and Biophysical Research Communications. 205(1): 429-434.

Fischer M, Bur-Romero P, Brown L G et al. (1990): Homologous ribosomal protein genes in the human X- and Y-chromosomes escape from X-inactivation and possible implementation for Turner syndrome. Cell 63: 1205-1218.

Freund C, Horsford D J, McInnes R R (1996): Transcription factor genes and the developing eye: a genetic perspective. Hum Mol Genet 5: 1471-1488.

Gehring W J, Qian Y Q, Billeter M, Furukubo-Tokunaga K, Schier A F, Resendez-Perez D, Affolter M, Otting G, Wüthrich K (1994): Homeodomain-DNA recognition. Cell 78: 211-223.

Gough N M, Gearing D P, Nicola N A, Baker E, Pritchard M, Callen D F, Sutherland G R (1990). Localization of the human GM-C SF receptor gene to the X-Y pseudoautosomal region. Nature 345: 734736

Grumbach M M, Conte F A (1992): Disorders of sexual differentiation. In: Williams textbook of endocrinology, 8th edn., edited by Wilson J D, Foster D W, pp. 853-952, Philadelphia, WB Saunders.

Hall J G, Gilchrist D M (1990): Turner syndrome and its variants. Pediatr. Clin. North Am. 37: 1421-1436.

Henke A, Wapenaar M, van Ommen G-J, Maraschio P, Camerino 0, Rappold G A (1991): Deletions within the pseudoautosomal region help map three new markers and indicate a possible role of this region in linear growth. Am J Hum Genet 49:811-819.

Hernandez D, Fisher E M C (1996): Down syndrome genetics: unravelling a multifactorial disorder. Hum Mol Genet 5:1411-1416.

Kenyon C (1994): If birds can fly, why can't we? Homeotic genes and evolution. Cell 78: 175-180.

Krumlauf R (1994): Hox genes in vertebrate development. Cell 78: 191-201.

Kulharya A S, Roop H, Kukolich M K, Nachtman R G, Belmont J W, Garcia-Heras J (1995): Mild phenotypic effects of a de novo deletion Xpter→Xp22.3 and duplication 3pter→3p23. Am J Med Genet 56:16-21.

Lawrence P A, Morata G (1994): Homeobox genes: their function in *Drosophila* segmentation and pattern formation. Cell 78: 181-189.

Lehrach H, Drmnac R, Hoheisel J D, Larin Z, Lemon G, Monaco A P, Nizetic D, et a,. Hybridization finger printing in genome mapping and sequencing. In Davies K E, Tilghman S, Eds. Genome Analysis 1990: 39-81 Cold Spring Harbor, N.Y.

Levilliers J, Quack B, Weissenbach J, Petit C (1989): Exchange of terminal portions of X- and Y-chromosomal short arms in human XY females. Proc Natl Acad Sci USA 86:2296-2300.

Lichter P, Cremer T, Human Cytogenetics: A practical Approach, IRL Press 1992, Oxford, New York, Tokyo Lippe B M (1991): Turner Syndrome. Endocrinol Metab Clin North Am 20: 121-152. Magenis R E, Tochen M L Holahan K P, Carey T, Allen L, Brown M G (1984): Turner syndrome resulting from partial deletion of Y-chromosome short arm: localization of male determinants. J Pediatr 105: 916-919.

Nelson D L, Ballabio A, Cremers F, Monaco A P, Schlessinger D (1995).—Report of the sixth international workshop on the X chromosome mapping. Cytogenet. Cell Genet. 71: 308-342

Ogata T, Goodfellow P, Petit C, Aya M, Matsuo N (1992): Short stature in a girl with a terminal Xp deletion distal to DXYS15: localization of a growth gene(s) in the pseudoautosomal region. J Med Genet 29:455-459.

Ogata T, Tyler-Smith C, Purvis-Smith S, Turner G (1993): Chromosomal localisation of a gene(s) for Turner stigmata on Yp. J. Med. Genet. 30: 918-922.

Ogata T, Yoshizawa. A, Muroya K, Matsuo N, Fukushima Y, Rappold G A, Yokoya S (1995): Short stature in a girl with partial monosomy of the pseudoautosomal region distal to DXYS15: further evidence for the assignment of the critical region for a pseudoautosomal growth gene(s). J Med Genet 32:831-834.

Ogata T, Matsuo N (1995): Turner syndrome and female sex chromosome aberrations: deduction of the principle factors involved in the development of clinical features. Hum. Genet. 95: 607-629.

Orita M, Suzuki Y, Sekiya T and Hayashi K (1989): Rapid and sensitive detection of point mutations and polymorphisms using the polymerase chain reaction. Genomics 5:874-879.

Pohlschmidt M, Rappold G A, Krause M, Ahlert D, Hosenfeld D, Weissenbach J, Gal A (1991): Ring Y chromosome: Molecular characterization by DNA probes. Cytogenet Cell Genet 56:65-68.

Qiagen (1993) TGGE Handbook, Diagen GmbH, TGMA 4112 3/93.

Rao E, Weiss B, Mertz A et al. (1995): Construction of a cosmid contig spanning the short stature candidate region in the pseudoautosomal region PAR 1. in: Turner syndrome in a life span perspective: Research and clinical aspects. Proceedings of the 4th International Symposium on Turner Syndrome, Gothenburg, Sweden, 18-21 May, 1995., edited by Albertsson-Wikland K, Ranke M B, pp. 19-24, Elsevier.

Rao E, Weiss B, Fukami M, Rump A, Niesler B, Mertz A, Muroya K, Binder G, Kirsch S, Winkelmann M, Nordsiek G, Heinrich U, Breuning M H, Ranke M B, Rosenthal A, Ogata T, Rappold G A (1997): Pseudoautosomal deletions encompassing a novel homeobox gene cause growth failure in idiopathic short stature and Turner syndrome. Nature Genet 15:54-62

Rappold G A (1993): The pseudoautosomal region of the human sex chromosomes. Hum Genet 92:315-324.

Rappold G A, Willson T A, Henke A, Gough N M (1992): Arrangement and localization of the human GM-CSF receptor α chain gene CSF2RA within the X-Y pseudoautosomal region. Genomics 14:455-461.

Ried K, Mertz A, Nagaraja R, Trusnich M, Riley J, Anand R, Page D, Lehrach H., Elliso J, Rappold G A (1995): Characterization of a yeast artificial chromosome contig spanning the pseudoautosomal region. Genomics 29:787-792.

Robinson A (1990): Demography and prevalence of Turner syndrome. In: Turner Syndrome., edited by Rosenfeld R G, Grumbach M M, pp. 93-100, New York, Marcel Dekker.

Rosenfeld R G (1992): Turner syndrome: a guide for physicians. Second edition. The Turner's Syndrome Society.

Rosenfeld R G, Tesch L-G, Rodriguez-Rigau L J, McCauley E, Albertsson-Wikland K, Asch R, Cara J, Conte F, Hall J G, Lippe B, Nagel T C, Neely E K, Page D C, Ranke M, Saenger P, Watkins J M, Wilson D M (1994): Recommendations for diagnosis, treatment, and management of individuals with Turner syndrome. The Endocrinologist 4(5): 351-358.

Rovescalli A C, Asoh S, Nirenberg M (1996): Cloning and characterization of four murine homeobox genes. Proc Natl Acad Sci USA 93:10691-10696.

Schaefer L, Ferrero G B, Grillo A, Bassi M T, Roth E J, Wapenaar M C, van Ommen G-J B, Mohandas T K, Rocchi M, Zoghbi H Y, Ballabio A (1993): A high resolution deletion map of human chromosome Xp22. Nature genetics 4: 272-279.

Shalet S M (1993): Leukemia in children treated with growth hormone. Journal of Pediatric Endocrinology 6: 109-11

Vimpani G V, Vimpani A F, Lidgard G P, Cameron E H D, Farquhar J W (1977) Prevalence of severe growth hormone deficiency. Br Med J. 2: 427-430

Zinn A R, Page D C, Fisher E M C (1993): Turner syndrome: the case of the missing sex chromosome. TIG 9 (3): 90-93.

The invention claimed is:

1. A kit for identification of a human subject having a genetic mutation in the a SHOX gene, wherein said SHOX gene consists of SEQ ID No:14, and said SHOX gene is responsible for diminished human growth, comprising
   a) an exon-flanking, oligonucleotide primer for an exon nucleotide sequence of SEQ ID NO: 14, wherein the oligonucleotide primer is 18 or 20-26 nucleotides, the oligonucleiotide primer only specifically hybridizes to the fully complementary strand of the SHOX gene, and the full length of said primer is completely identical to a partial sequence of an exon-flanking nucleotide sequence of SEQ ID NO: 14; or
   b) an oligonucleotide primer for an exon nucleotide sequence of SEQ ID NO: 14, wherein the oligonucleotide primer is 18 or 20-26 nucleotides and only specifically hybridizes to the fully complementary strand of the SHOX gene, and the full length of said primer is completely identical to a partial sequence of an exon nucleotide sequence of SEQ ID NO:14, and a hybridization buffer.

2. The kit according to claim 1, wherein said exon nucleotide sequence is a polynucleotide sequence of comprising SEQ ID NO: 2.

3. The kit according to claim 1, further comprising a detection label.

4. The kit according to claim 1, further comprising a polynucleotide of the SHOX gene as a positive control.

5. A method for identification of a human subject suspected of having a genetic mutation in a SHOX gene, wherein said SHOX gene consists of SEQ ID NO:14, comprising
   a) obtaining a biological sample containing a polynucleotide from a human subject;
   b) amplifying the polynucleotide of a) in the presence of a primer, wherein said primer is an exon flanking primer for an exon nucleotide sequence of SEQ ID NO: 14, said primer only specifically hybridizes to the fully complementary strand of the SHOX gene, and wherein the oligonucleotide primer is 18 or 20-26 nucleotides and the full length of said primer is completely identical to a partial sequence of an exon-flanking nucleotide sequence of SEQ ID NO: 14 and
   c) sequencing amplification products from step b) and determining whether a genetic mutation occurs in the SHOX gene of the subject.

6. The method according to claim 5, wherein said exon nucleotide sequence is a polynucleotide sequence selected from the group consisting of SEQ ID NO: 2, SEQ ID NO:3, SEQ ID NO:4, SEQ ID NO:5, SEQ ID NO:6 and SEQ ID NO:7.

7. A purified polypeptide comprising SEQ ID NO: 11.

* * * * *